US012655158B2

(12) United States Patent
Monchaud et al.

(10) Patent No.: US 12,655,158 B2
(45) Date of Patent: Jun. 16, 2026

(54) BIOMIMETIC G-QUARTET COMPOUNDS

(71) Applicants: CENTRE NATIONAL DE LA RECHERCHE SCIENTIFIQUE, Paris (FR); UNIVERSITE DE BOURGOGNE, Dijon Cedex (FR)

(72) Inventors: David Monchaud, Dijon (FR); Ibai Valverde, Marsannay-la-Côte (FR); Pauline Lejault, Neuilly les Dijon (FR); Francesco Rota Sperti, Dijon (FR)

(73) Assignees: CENTRE NATIONAL DE LA RECHERCHE SCIENTIFIQUE, Paris (FR); UNIVERSITE DE BOURGOGNE, Dijon (FR)

( * ) Notice: Subject to any disclaimer, the term of this patent is extended or adjusted under 35 U.S.C. 154(b) by 812 days.

(21) Appl. No.: 17/915,713

(22) PCT Filed: Mar. 30, 2021

(86) PCT No.: PCT/EP2021/058268
§ 371 (c)(1),
(2) Date: Sep. 29, 2022

(87) PCT Pub. No.: WO2021/198239
PCT Pub. Date: Oct. 7, 2021

(65) Prior Publication Data

US 2023/0135545 A1 May 4, 2023

(30) Foreign Application Priority Data

Mar. 31, 2020 (EP) .................................... 20315084

(51) Int. Cl.
*C07D 519/00* (2006.01)

(52) U.S. Cl.
CPC .................................. *C07D 519/00* (2013.01)

(58) Field of Classification Search
CPC .................................................... C07D 519/00
USPC ......................................................... 540/145
See application file for complete search history.

(56) References Cited

PUBLICATIONS

Renard et al., "Small-molecule affinity capture of DNA/RNA quadruplexes and their identification in vitro and in vivo through the G4RP protocol"; Nucleic Acids Research; Jun. 20, 2019; vol. 47, No. 11, pp. 5502-5510.
Yang et al., "Transcriptome-wide identification of transient RNA G-quadruplexes in human cells"; Nature Communications; Nov. 9, 2018 ; vol. 9, No. 1, pp. 1-11.
Aguerre et al., "Synthetic G-Quartets as Versatile Nanotools for the Luminescent Detection of G-Quadruplexes"; Chimia International Journal for Chemistry; Sep. 30, 2015; vol. 69, No. 9, pp. 530-536.
Vanasschen et al., "Gadolinium DOTA Chelates Featuring Alkyne Groups Directly Grafted on the Tetraaza Macrocyclic Ring: Synthesis, Relaxation Properties, "Click" Reaction, and High-Relaxivity Micelles"; Inorganic Chemistry; Sep. 19, 2011; vol. 50, No. 18, pp. 8946-8958.
Chambers et al., "High-throughput sequencing of DNA G-quadruplex structures in the human genome"; Nature Biotechnology; Jul. 20, 2015; vol. 33, No. 8, pp. 877-883.
Hansel-Hertsch et al., "DNA G-quadruplexes in the human genome: detection, functions and therapeutic potential"; Nature Reviews Molecular Cell Biology; Feb. 22, 2017; vol. 18, No. 5, pp. 279-284.
International Search Report and Written Opinion issued on May 11, 2021 in corresponding International Patent Application No. PCT/EP2021/058268; 13 pages.

*Primary Examiner* — Kahsay Habte
(74) *Attorney, Agent, or Firm* — Maier & Maier, PLLC

(57) ABSTRACT

A compound of formula I:

(I)

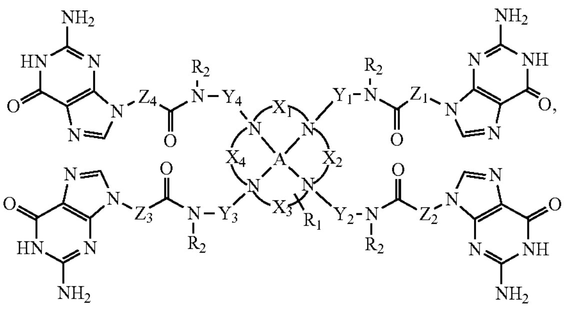

wherein A is present or absent; X1, X2, X3 and X4 are, independently from each other, an alkyl;
Y1, Y2, Y3 and Y4 are independently from each other a C1-C10 alkyl, —Z1, Z2, Z3 and Z4 are independently from each other a C1-C5 linear alkyl; R1 is a group allowing to carry out bioorthogonal reactions; and R2 is group including a N.

10 Claims, 5 Drawing Sheets

Specification includes a Sequence Listing.

[Fig. 1]
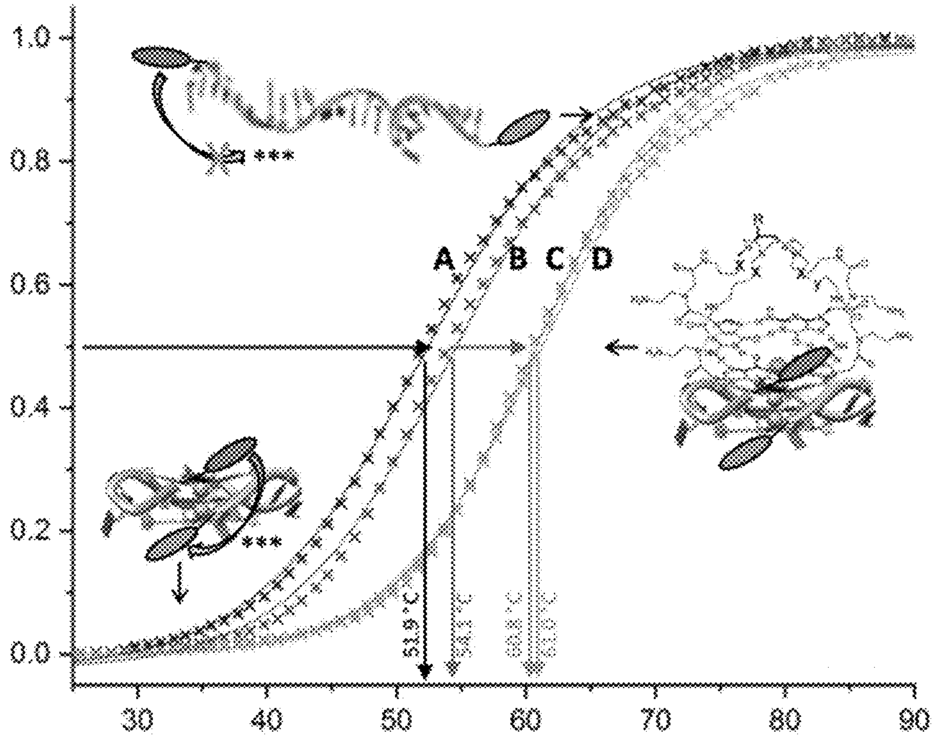

[Fig. 2]
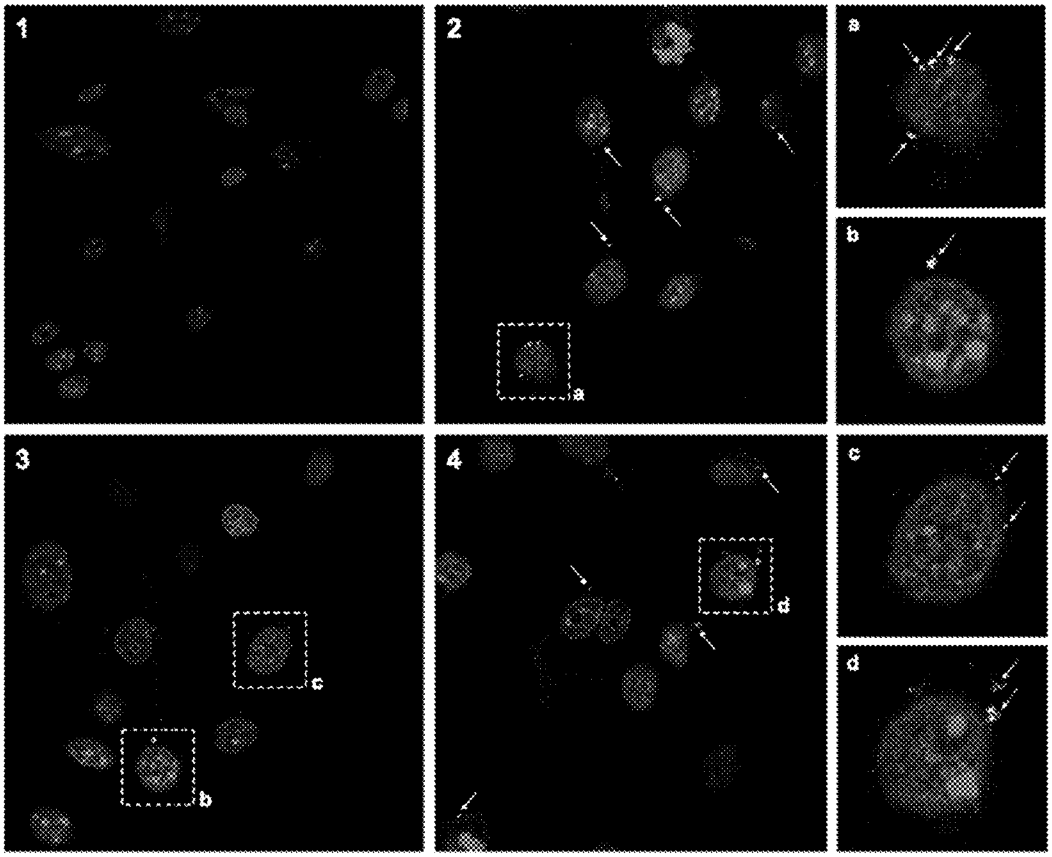

[Fig. 3]
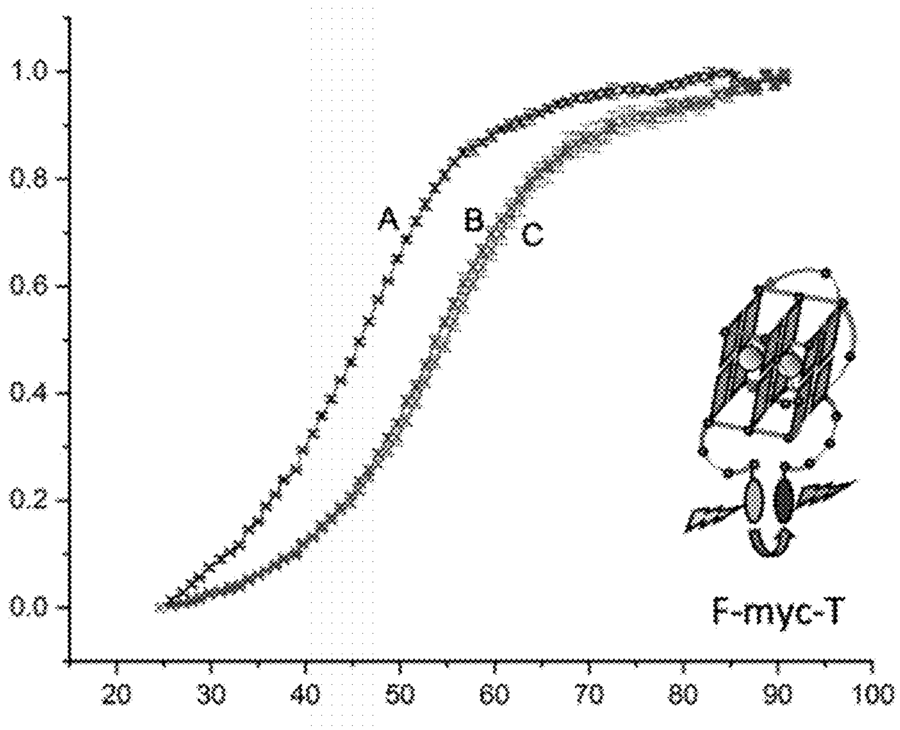
[Fig. 4]
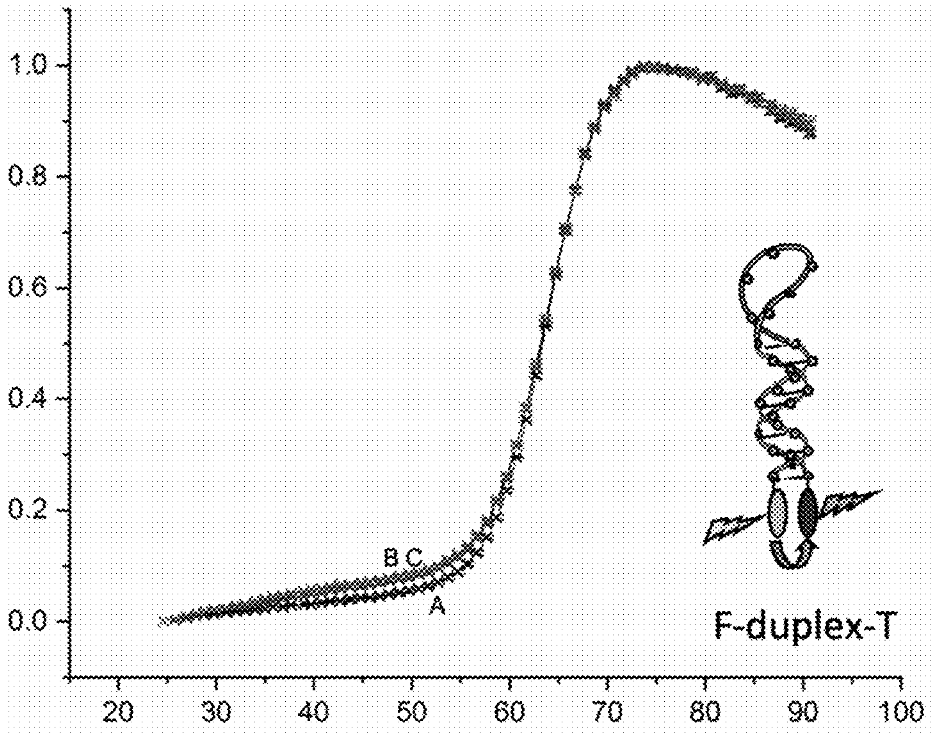

[Fig. 5]
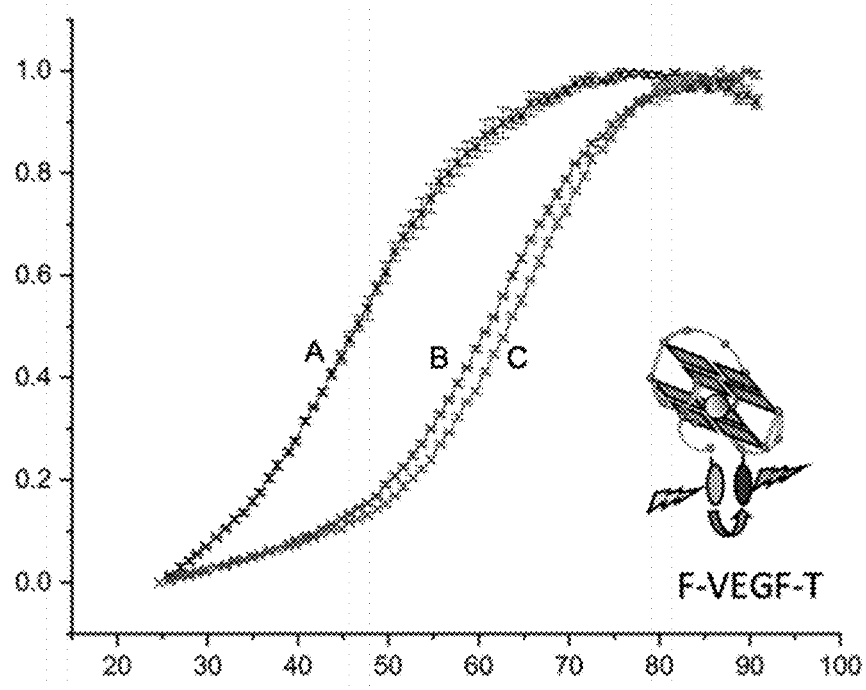

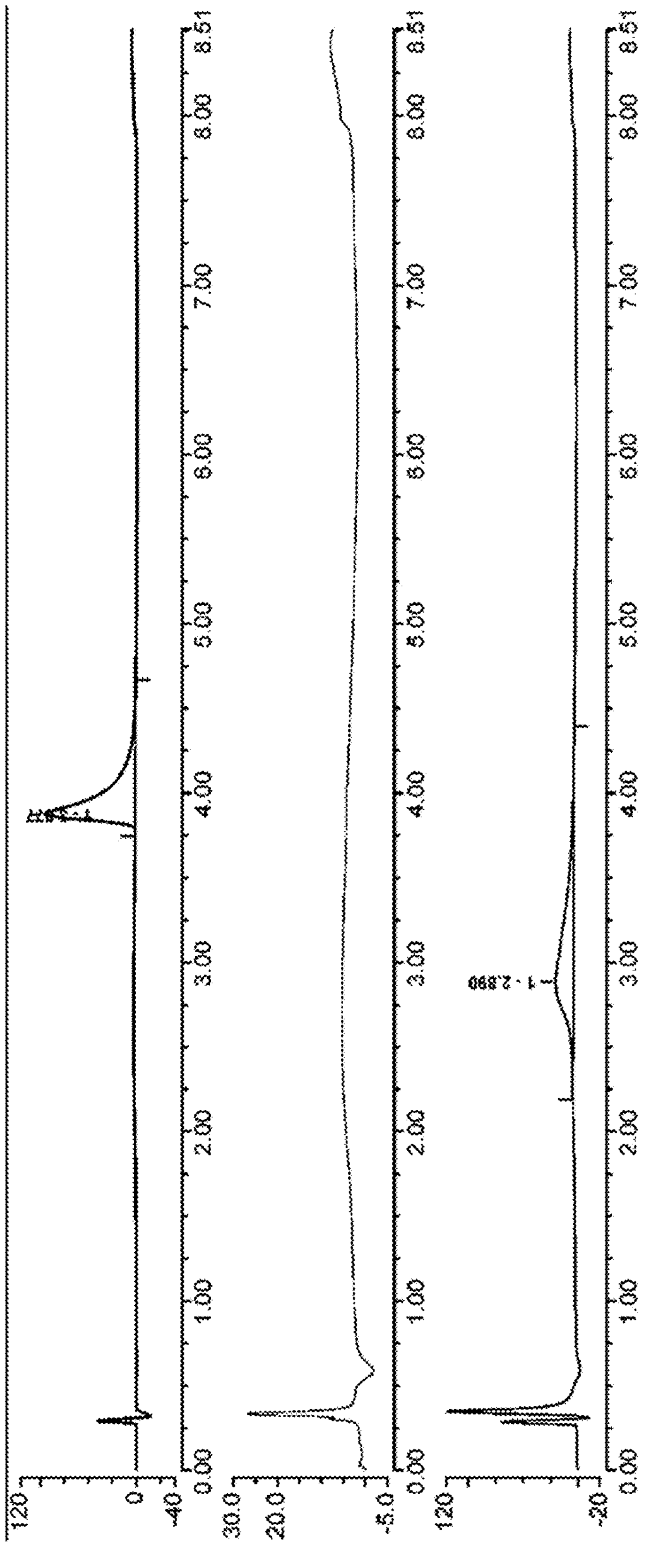
[Fig. 6]

BIOMIMETIC G-QUARTET COMPOUNDS

FIELD

The invention relates to biomimetic G-quartet compounds.

BACKGROUND

Although DNA and proteins have evolved to carry out many functions in complex cellular organisms, it has been recently identified that RNA molecules are more than simple messengers between DNA and proteins and exhibit rich regulatory functions in development and disease.

In 1986, Walter Gilbert promoted the idea of an 'RNA world' of early life forms that use only RNA molecules to carry genetic information and catalyze their own synthesis (Nature 319, 618 (1986)).

Aside from the classical coding RNA mRNA, noncoding RNA such as tRNA and rRNA act between DNA and proteins as central components for translation for instance.

Formation of G4-DNA is associated with key cellular processes including transcription and replication (Nat. Rev. Mol. Cell Biol. 18, 279 (2017)). To better understand their roles in cell biology, two methods are available G4-seq (Nat. Biotechnol. 33, 877 (2015)) and G4 ChIP-seq (Nat. Genet. 48, 1267 (2016)).

Formation of G4-RNA is implicated in key RNA metabolism events, including the regulation of RNA processing and translation. To better understand their roles in cell biology, two methods are available, rG4-seq (Nat. Meth. 13, 841 (2016)) and G4RP-seq (Nat. Commun. 9, 4730 (2018)).

Of interest, the method developed by Yang et al. (Yang et al. Nat Commun 9, 4730 (2018)) uniquely allows for studying the mammalian G4-RNA landscape in in vivo-like conditions via a method referred to as G4RP-seq (G4-RNA precipitation and sequencing) that relies on a molecular tool called BioTASQ (for biotinylated TASQ). G4RP-seq was also useful for evaluating the mechanisms underlying the biological activity of G4 ligands when used as therapeutics.

BioTASQ ligand is the biotinylated version of a previously described compound $^{PNA}$DOTASQ, a TASQ compound of formula:

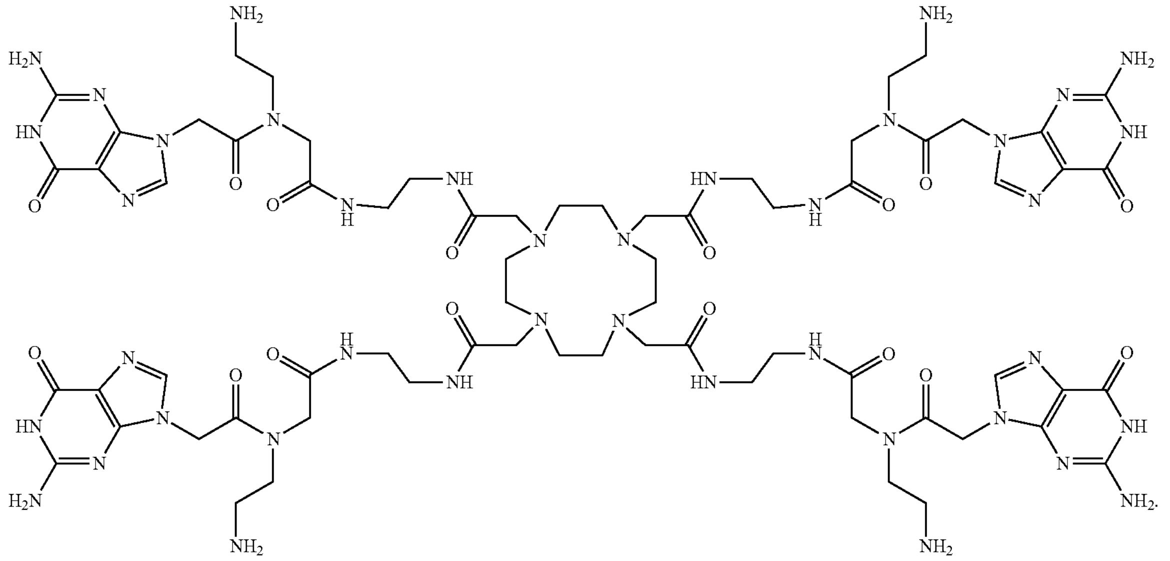 [SMILES: NCCN(CC(=O)NCCNC(=O)CN1CCN(CC(=O)NCCNC(=O)CN(CCN)C(=O)Cn2cnc3c(=O)[nH]c(N)nc32)CCN(CC(=O)NCCNC(=O)CN(CCN)C(=O)Cn2cnc3c(=O)[nH]c(N)nc32)CCN(CC(=O)NCCNC(=O)CN(CCN)C(=O)Cn2cnc3c(=O)[nH]c(N)nc32)CC1)C(=O)Cn1cnc2c(=O)[nH]c(N)nc21]

Globally, 74% of the human genome is thought to give rise to RNA transcripts, with less than 2% of this corresponding to protein-coding mRNAs numerous (Curr. Gene Ther. 16, 220 (2016)).

The biological functions and cellular regulations of RNAs are dependent on their secondary and tertiary structures. RNAs can adopt intricate bulged, stem-loop structures involving duplex-, triplex-, and quadruplex-RNA motifs.

G-quadruplexes (G4s) are structures formed by Hoogsteen bonding of four guanines to form planar guanine quartet (G-quartet) units, which π-stack on each other, to assemble into columnar four-stranded structures with the central cavity stabilized by monovalent cations (i.e., $K^+$, $Na^+$). G4 folding is spontaneous in vitro and results in a highly stable structure. Both single-stranded DNA and RNA can fold into G4s: G4 formation in DNA molecules is thought to be transient and dependent on DNA transactions (replication, transcription) as a result of the local separation of the two strands of the genomic DNA; G4 formation in RNA molecules is more likely due to their predominant single-stranded nature in vivo.

While BioTASQ is efficient to purify the G4RNA, its quadruplex-affinity is decreased as compared to the parent compound $^{PNA}$DOTASQ, likely due to an intramolecular interaction between the biotin tag and a guanine. This pitfall is partly circumvented in vitro (target engagement).

So, to date, there is a need to obviate this drawback along with some pitfalls identified during the studies of this first generation of multivalent TASQ.

SUMMARY

One aim of the invention is to provide new and efficient compounds allowing to identify and to purify both G4-DNA and G4-RNA, with an increased affinity for their targets.

Another aim of the invention is to provide more versatile compounds having enhanced bioavailability properties, which makes them readily usable in vivo, for both identification and purification purposes.

To this end, the invention relates to a compound of formula I:

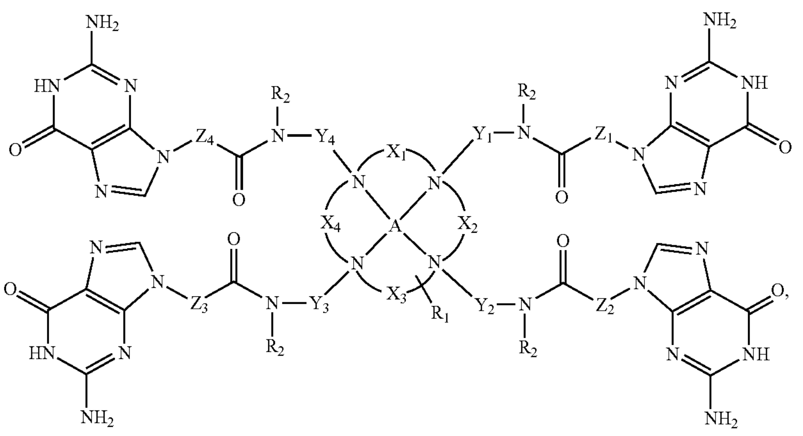

(I)

wherein

A is absent or is a metallic cation, in particular a lanthanide used for optical imaging, in particular $Eu^{3+}$, $Tb^{3+}$, $Dy^{3+}$, or $Yb^{3+}$;

X1, X2 and X4 are, independently from each other a C1-C3 linear alkyl;

X3 is a C2-C3 alkyl, substituted by R1;

Y1, Y2, Y3 and Y4 are independently from each other a C1-C10 alkyl, preferably a C5-C10 alkyl, saturated or not, substituted or not by an acid group, possibly with a substitution of at least one carbon atom by N, P, a phenyl, a C═O group, phosphonate group, or a triazole group;

Z1, Z2, Z3 and Z4 are independently from each other a C1-C5 linear alkyl;

R1 is $(CH_2)$p-L-T, wherein p varies from 0 to 5; and

L is a linear or branched, saturated or not, C1-C12 alkyl, possibly with a substitution of at least one carbon by: a C═O group or an heteroatom, an aryl group possibly substituted, a triazole group, or a diazirin group;

T is a group allowing to carry out bioorthogonal reactions, in particular the following groups: azide, tetrazine substituted or not, alkyne, constrained alkyne such as cyclooctyne or cyclononyne, and in particular dibenzocyclooctyne, bicyclononyne, constrained cycloalkenes, such as trans-cyclooctene, norbornene, cycloproprene, R2 is $(CH_2)_m$—NHRx, wherein m varies from 1 to 4 and Rx is H or a protecting group such as Boc, Fmoc, Carboxybenzyl, or a guanidinium group, or a salt or a solvate thereof.

The inventors have unexpectedly identified new generations of TASQ compounds having high affinity for G-quadruplex structures, in vitro and in vivo, and which are very versatile and can be substituted easily by functional residues.

In the above formula the central X1-N-X2-N-X3-N-X4-N ring can be complexed with a metallic cation or not. When the compound of formula I is not complexed with a metallic cation, its formula is the following formula Ia:

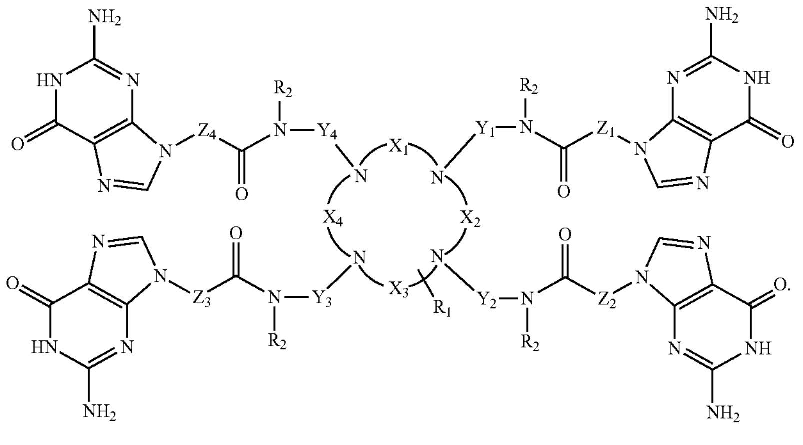

(Ia)

The metallic action is advantageously a lanthanide cation chosen from: $Sm^{3+}$, $Eu^{3+}$, $Tb^{3+}$, $Dy^{3+}$, $Lu^{3+}$, $Yb^{3+}$ and $Nd^{3+}$. Lanthanide lumiphores have emission lifetimes in the millisecond range, whereas those of biological fluorophores are typically less than 10 nanoseconds. Consequently, lanthanide-emitted photons can be differentiated from biological autofluorescence using pulsed excitation and time-delayed signal acquisition. It is therefore advantageous to use a lanthanide metal cation in the compound according to the invention.

In the compound of formula I, or Ia, X1, X2 and X4, independently from each other can be a C1, a C2 or a C3 linear alkyl, namely a methyl, an ethyl or a propyl group. X3 is a C2 or a C3 alkyl, i.e. a methyl or an ethyl group.

Y1-Y4 can be independently from each other a C1-C10 alkyl, which means that Y can be a C1, a C2, a C3, a C4, a C5, a C6, a C7, a C8, a C9 or a C10 alkyl, namely a methyl, an ethyl, a propyl, a butyl, a pentyl, an hexyl, an heptyl, an octyl, a nonyl or a decyl group. At least one carbon atom of Y can be substituted by at least a N, at least a P, a phenyl, a C═O group, phosphonate group, a triazole group For instance, Y1-Y4 can be one of the followings:

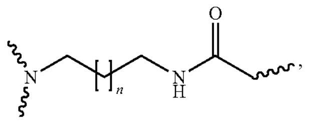

wherein n varies from 0 to 5;

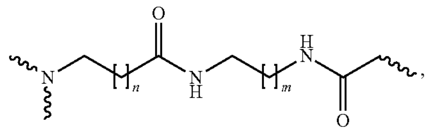

wherein n varies from 0 to 5 and m varies from 1 to 3;

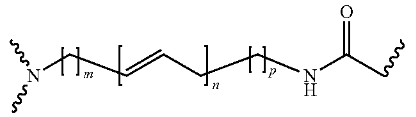

wherein n and m vary from 1 to 5, and wherein p varies from 0 to 5;

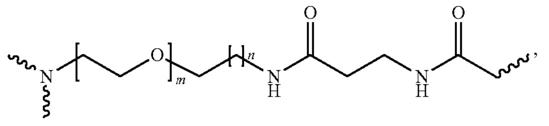

wherein n varies from 0 to 5 and m varies from 1 to 3;

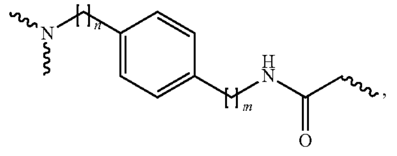

wherein n varies from 0 to 5 and m varies from 1 to 3;

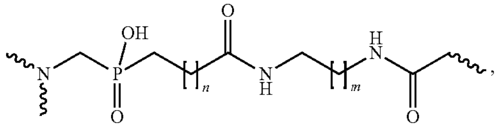

wherein n varies from 0 to 5 and m varies from 1 to 3;

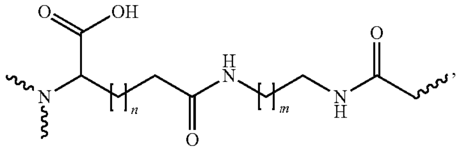

wherein n varies from 0 to 5 and m varies from 1 to 3;

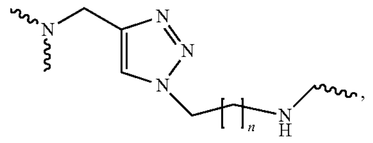

wherein n varies from 0 to 5;

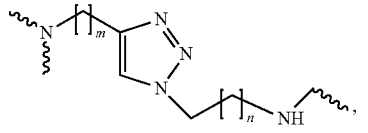

wherein n varies from 0 to 5 and m varies from 1 to 4;

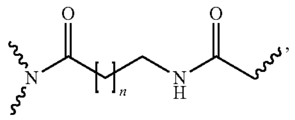

wherein n varies from 0 to 5; and

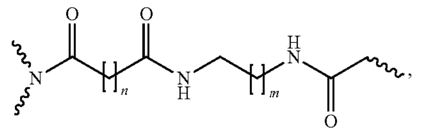

wherein n varies from 0 to 5 and m varies from 1 to 3.

Advantageously, Y1, Y2, Y3 and Y4 are the same.

In the above-mentioned formula, Z1, Z2, Z3 and Z4 are independently from each other a C1-C5 linear alkyl, i.e. Z1, Z2, Z3 and Z4 are independently from each other are a methyl group, an ethyl group, a propyl group, a butyl group or a pentyl group.

Advantageously, Z1, Z2, Z3 and Z4 are the same.

The above mentioned formula differ from the compounds known in the art, in particular from BioTASQ and $^{PNA}$DOT-ASQ by R1.

R1 is $(CH_2)_p$-L-T, wherein p varies from 0 to 5, which means that R1 equals to -L-T, $CH_2$-L-T, $CH_2$—$CH_2$-L-T, $CH_2$—$CH_2$—$CH_2$-L-T, $CH_2$—$CH_2$—$CH_2$—$CH_2$-L-T and $CH_2$—$CH_2$—$CH_2$—$CH_2$—$CH_2$-L-T.

L is a linear or branched, saturated or not, C1-C12 alkyl, i.e. C1, C2, C3, C4, C5, C6, C7, C8, C9, C10, C11, C12 alkyl, aliphatic or aromatic, or PEG.

T is a group allowing to carry out bioorthogonal reactions which refers to any chemical reaction that can occur inside of living systems without interfering with native biochemical processes.

The bioorthogonal chemistry typically proceeds in two steps. First, a cellular substrate is modified with a bioorthogonal functional group (a chemical tag) and introduced to the cell; substrates include metabolites, enzyme inhibitors, small molecules, etc. The chemical tag must not alter the structure of the substrate dramatically to avoid affecting its bioactivity. Secondly, a probe containing the complementary functional group is introduced to react with the tag and label the substrate once in its binding site in cella.

Although effective bioorthogonal reactions such as copper-assisted and copper-free click chemistry have been developed, new reactions are still under development to allow multiple methods of labeling to be used in the same biosystems.

According to the invention, T is preferably an alkyne —C≡CH or an azide and possibly a bicyclononyne (BCN CAS No 1263166-90-0) or a Dibenzocyclooctyne (DBCO CAS No 1255942-06-3) or one of their derivatives.

The compounds of Formula I are isomeric forms including isomers, diastereoisomers and salts thereof. The term "salts" embraces salts prepared from an inorganic acid or from an organic acid. Examples of such inorganic acids are hydrochloric, hydrobromic, hydroiodic, nitric, carbonic, sulfuric, and phosphoric acid.

Appropriate organic acids may be selected from aliphatic, cycloaliphatic, aromatic, araliphatic, heterocyclic, carboxylic and sulfonic classes of organic acids, example of which are formic, acetic, including trifluoraocetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, p-hydroxybutyric, malonic, galactaric and galacturonic acid. All of these salts may be prepared by conventional means from the corresponding compound of Formula I by reacting, for example, the appropriate acid with the compound of Formula I.

Certain compounds of the present invention including salts thereof can exist as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

The compounds according to the invention may be enantiomerically pure, such as a single enantiomer or a single diastereomer, or be stereoisomeric mixtures, such as a mixture of enantiomers, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include chiral synthesis from a suitable optically pure precursor or resolution of the racemate using, for example, chiral chromatography, recrystallization, resolution, diastereomeric salt formation, or derivatization into diastereomeric adducts followed by separation.

Advantageously, the invention relates to the compound as defined above, said compound being of formula II:

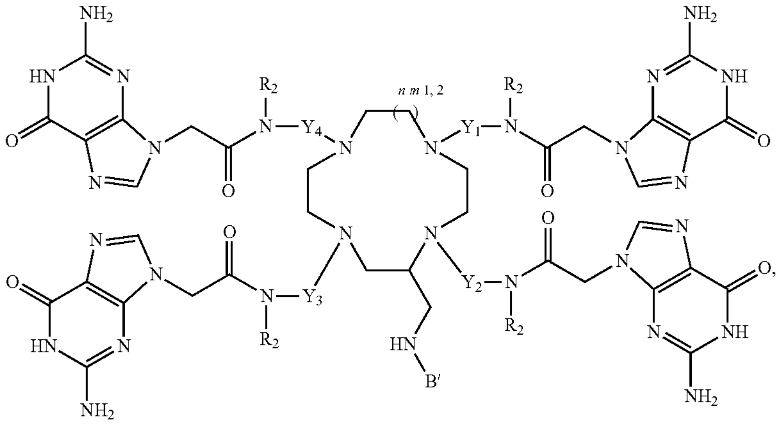

(II)

wherein B' is —(CO)—(CH2)m-T, m varying from 1 to 6, and Y1, Y2, Y3, Y4, T and R2 are as defined above.

Advantageous compounds, wherein Y1, Y2, Y3 and Y4 are the same are the following ones:
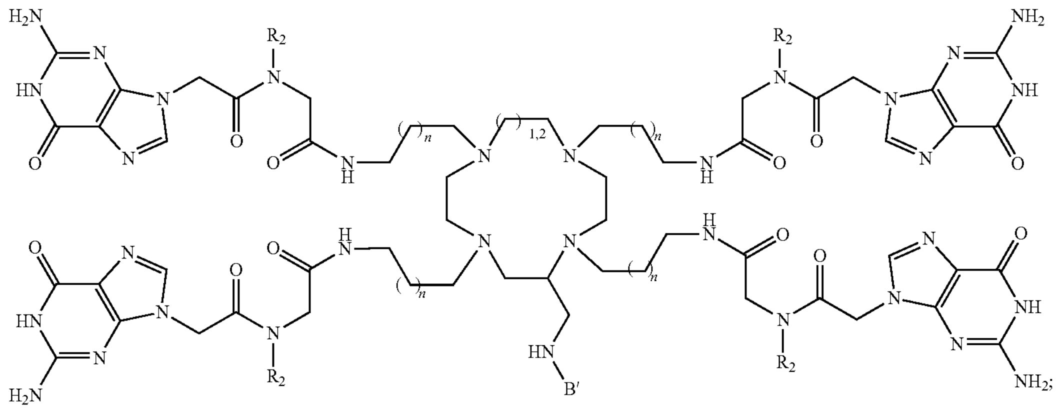
wherein n varies from 0 to 5;
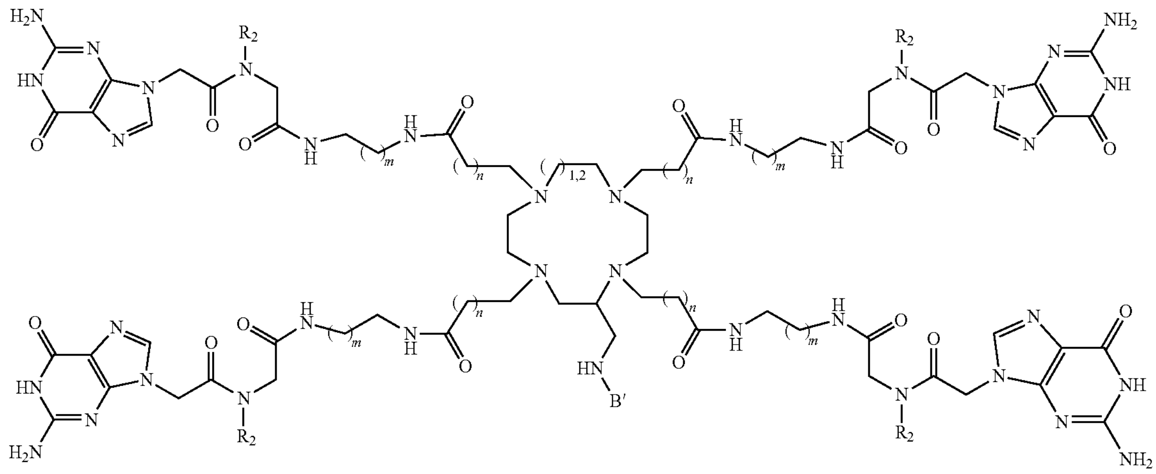
wherein n varies from 0 to 5 and m varies from 1 to 3;
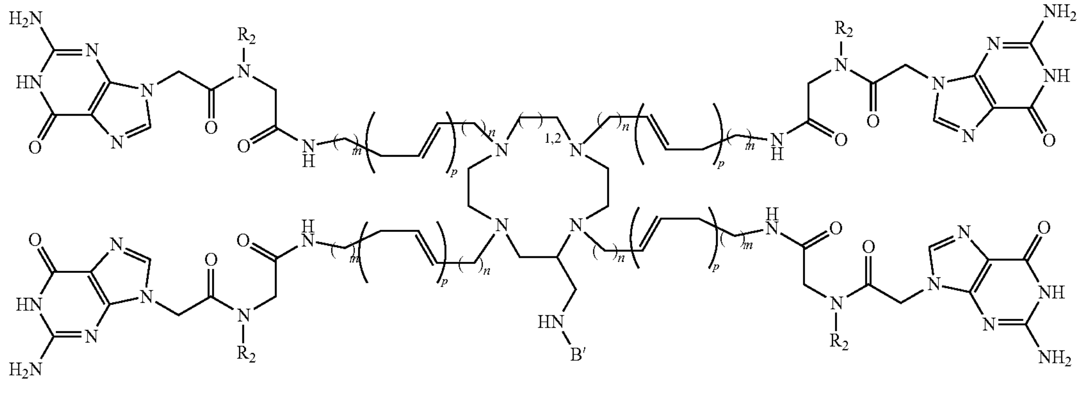

wherein n and m vary from 1 to 5, and wherein p varies from 0 to 5;
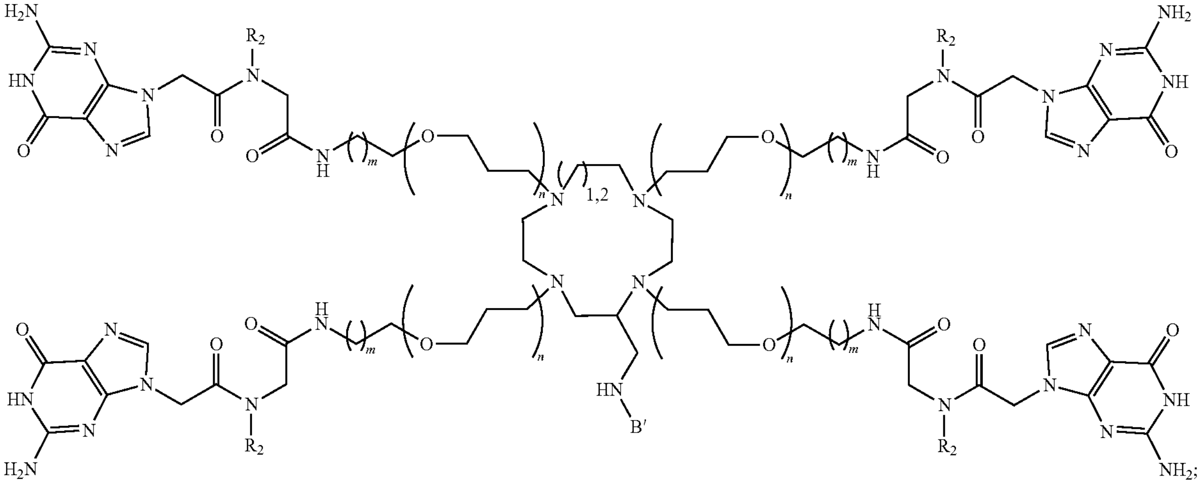
wherein n varies from 0 to 5 and m varies from 1 to 3;
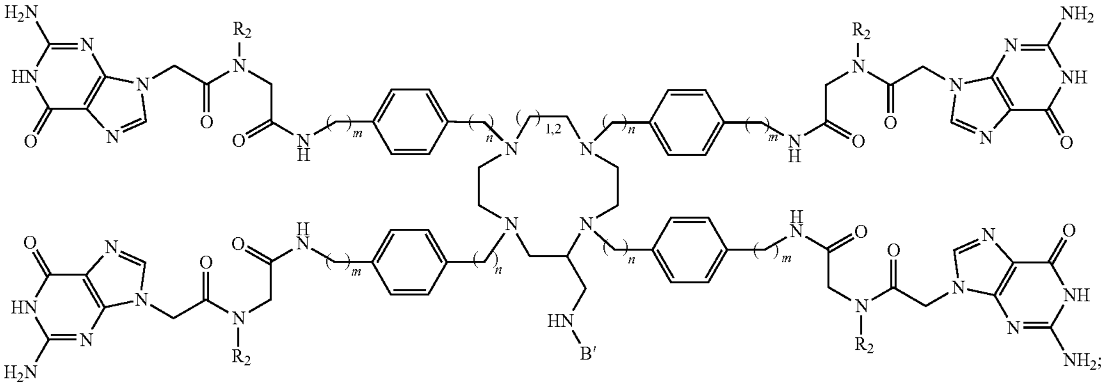
wherein n varies from 0 to 5 and m varies from 1 to 3;
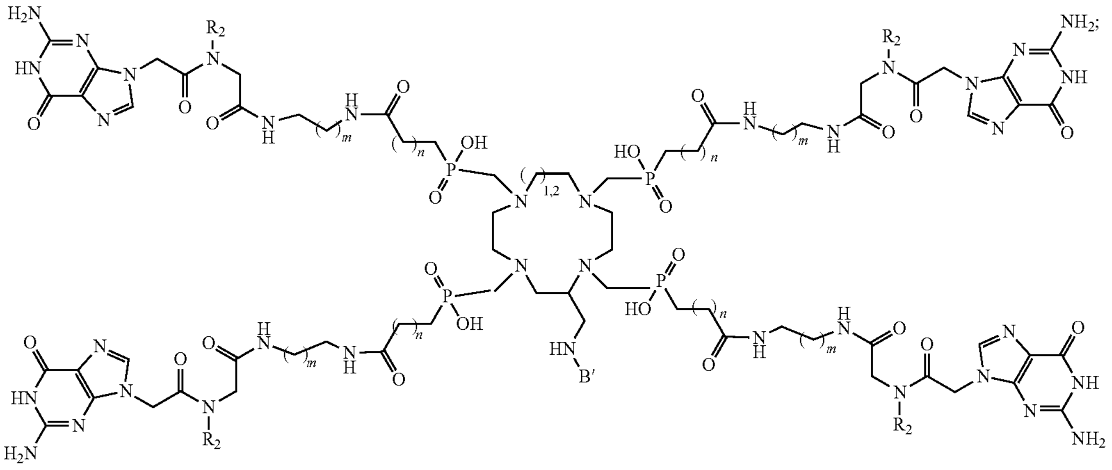

wherein n varies from 0 to 5 and m varies from 1 to 3;
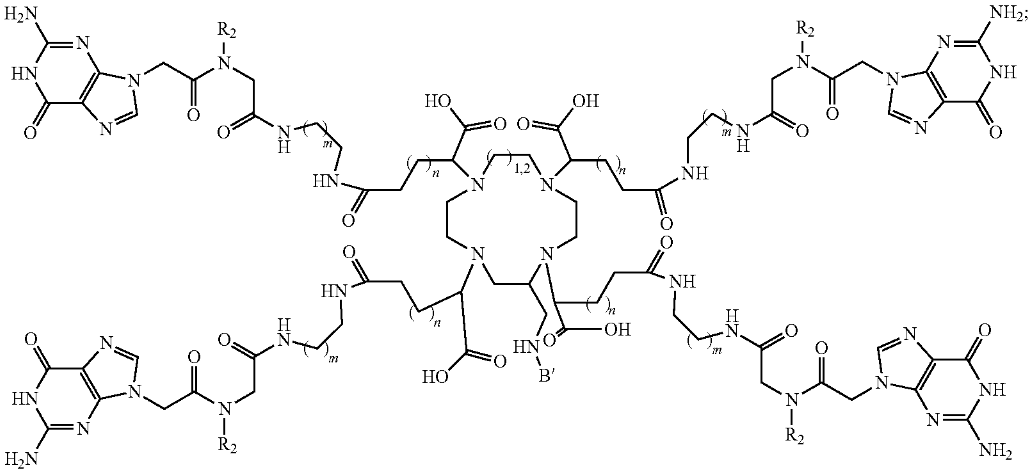
wherein n varies from 0 to 5 and m varies from 1 to 3;
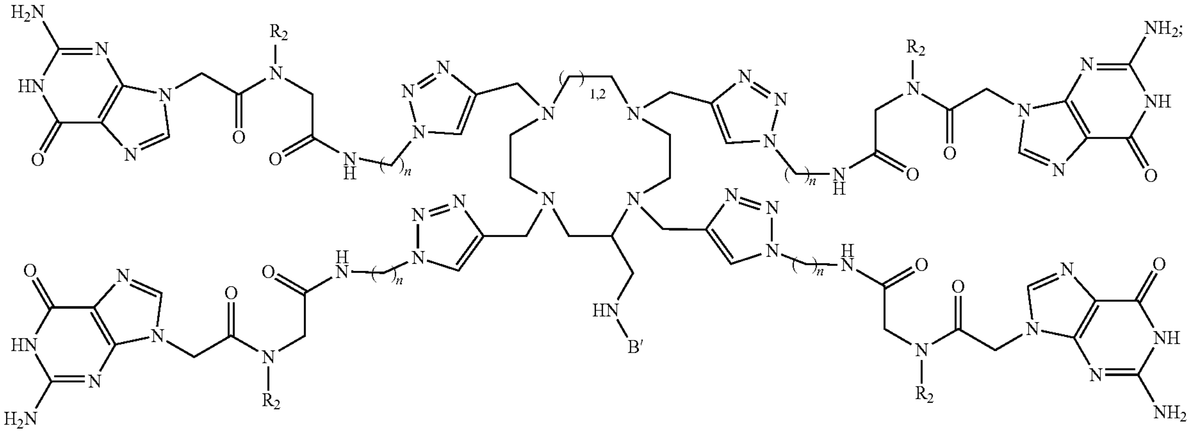
wherein n varies from 0 to 5;
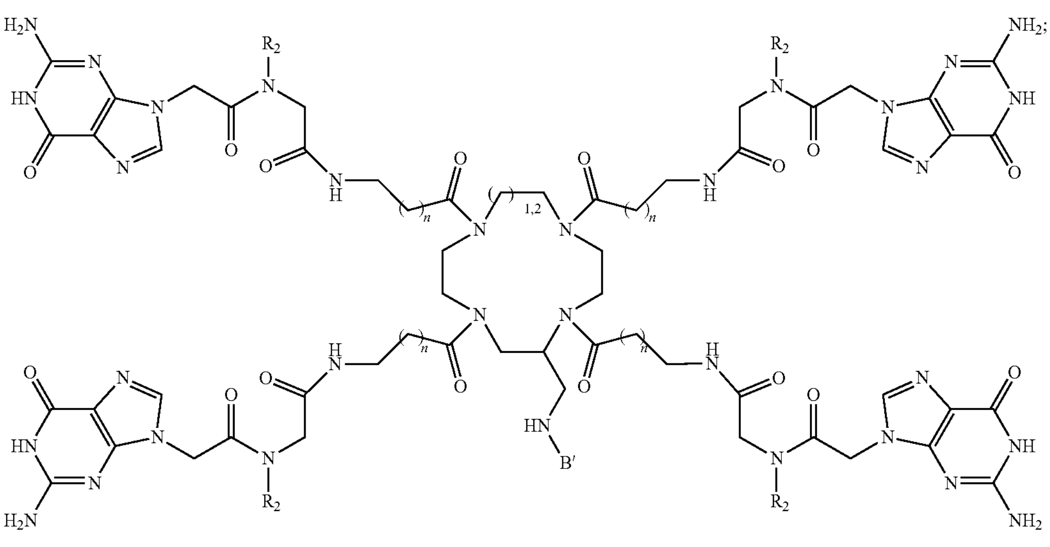

wherein n varies from 0 to 5; and
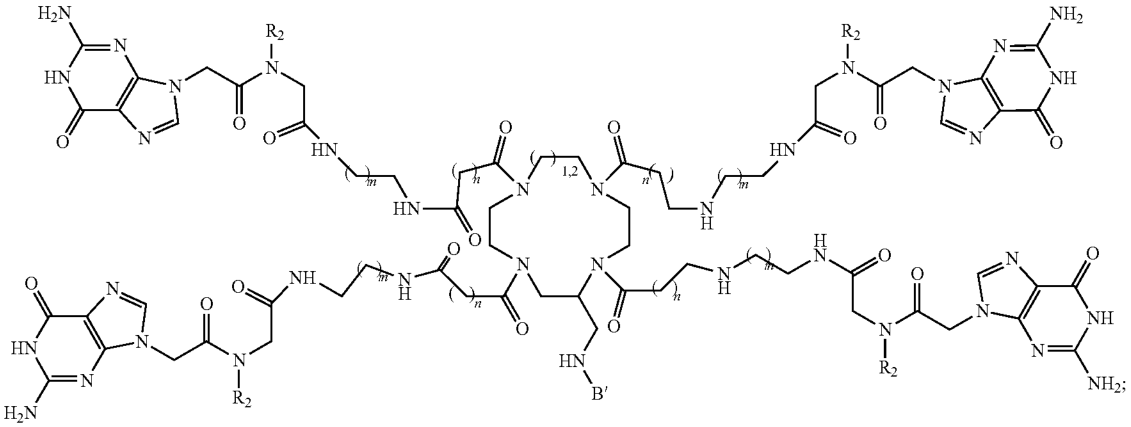
wherein n varies from 0 to 5 and m varies from 1 to 3.
Advantageously, the invention relates to the compound as defined above, said compound being of formula III:
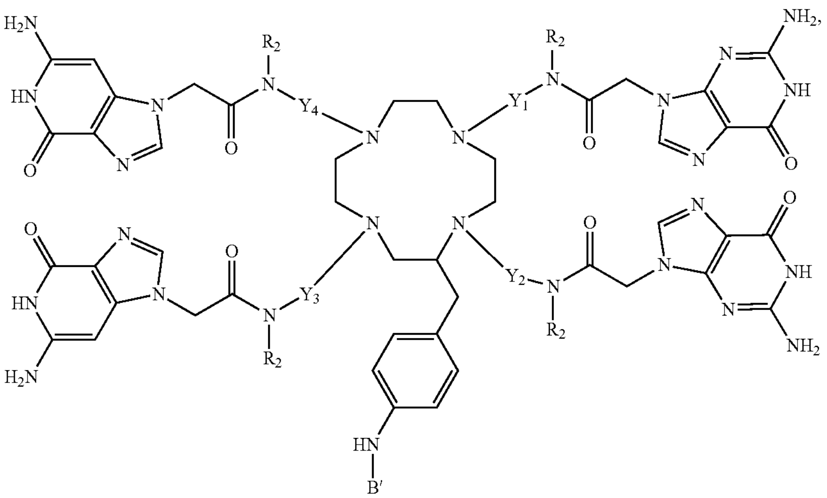

wherein B' is —W—$(CH_2)_m$-T, m varying from 1 to 6, and, W═CO, C(═O)—NH, C(═S)—NH, or a squaraine group, i.e. B' is —CO—$(CH_2)_m$-T, CO—NH—$(CH_2)_m$-T, CS—NH—$(CH_2)_m$-T,
preferably W is CO,
more preferably a compound of formula IIIa
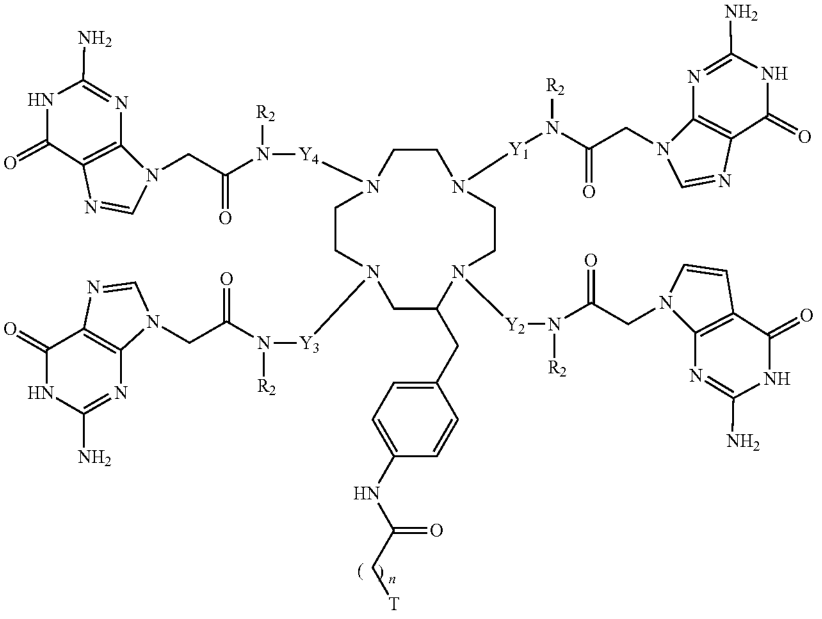
and Y1, Y2, Y3, Y4, T and R2 are as defined above.
Advantageous compounds, wherein Y1, Y2, Y3 and Y4 are the same are the following ones:
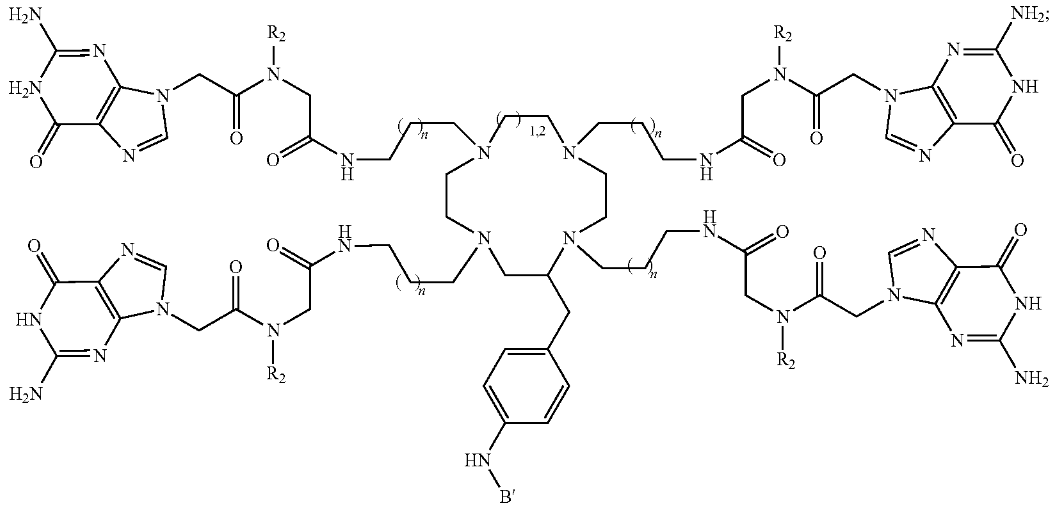

wherein n varies from 0 to 5;
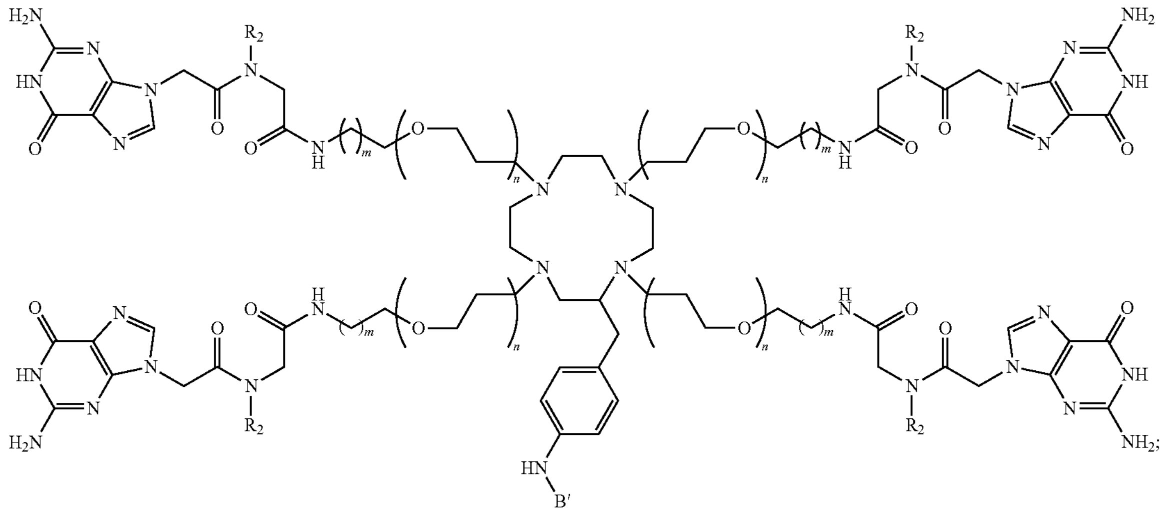
wherein n varies from 0 to 5 and m varies from 1 to 3;
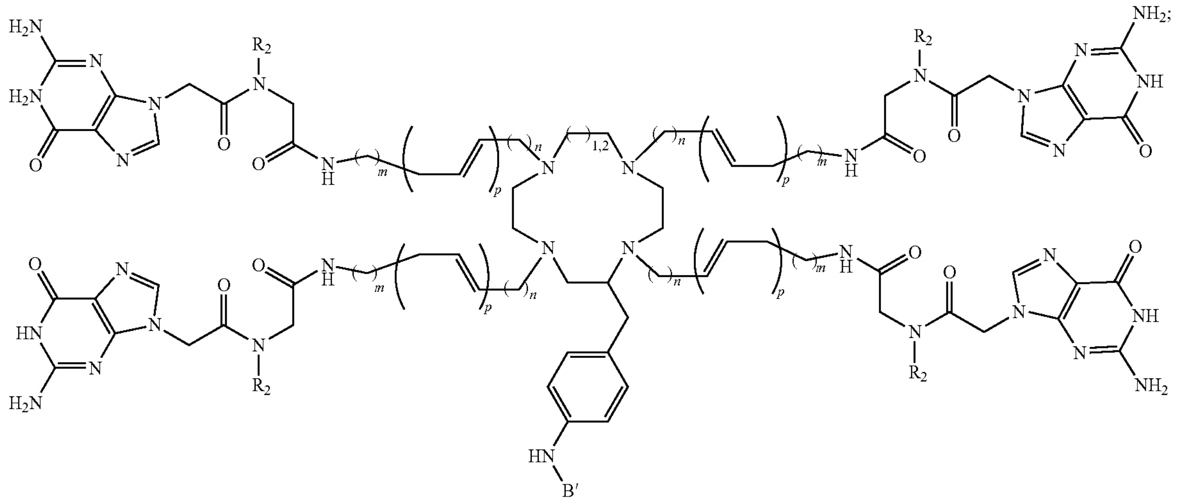

wherein n and m vary from 1 to 5, and wherein p varies from 0 to 5;
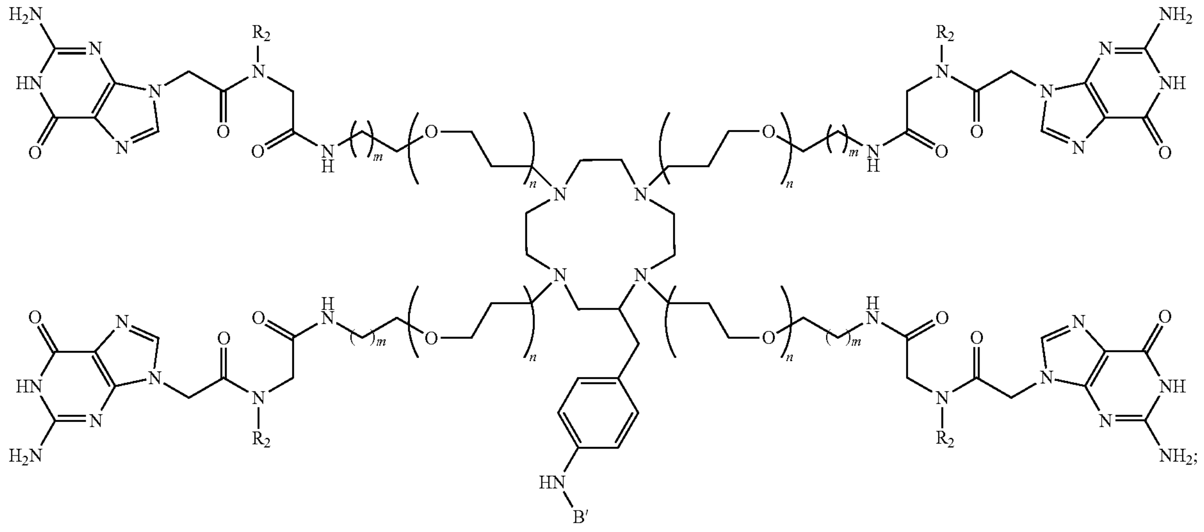
wherein n varies from 0 to 5 and m varies from 1 to 3;
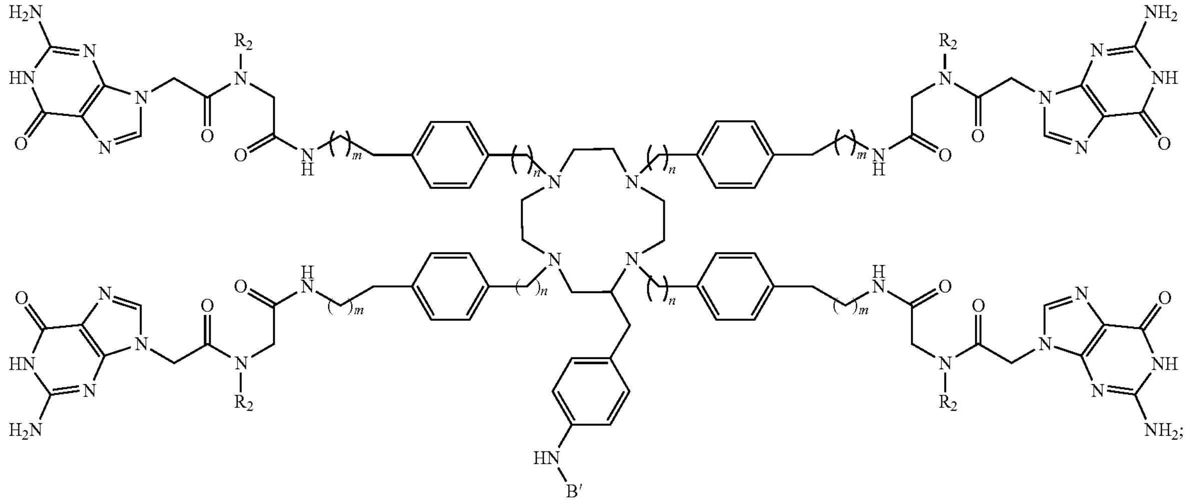

wherein n varies from 0 to 5 and m varies from 1 to 3;
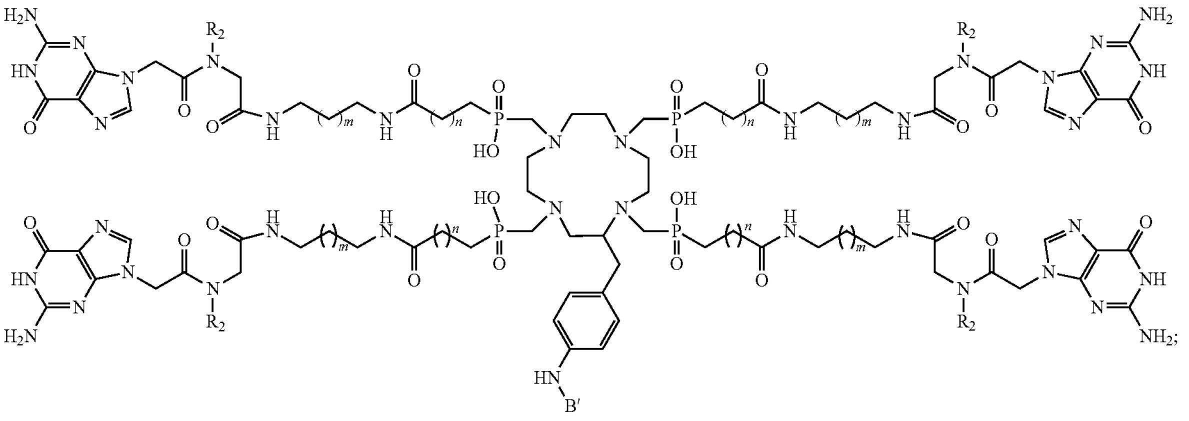
wherein n varies from 0 to 5 and m varies from 1 to 3;
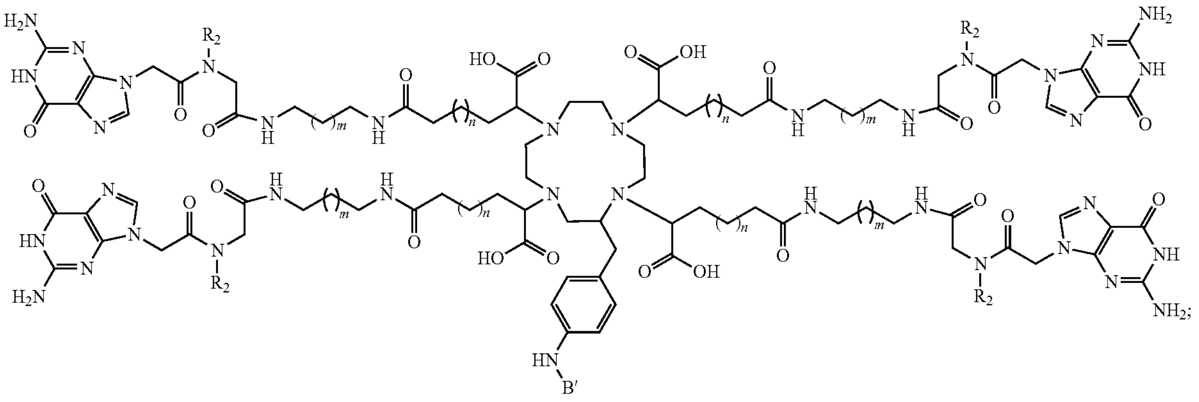
wherein n varies from 0 to 5 and m varies from 1 to 3;
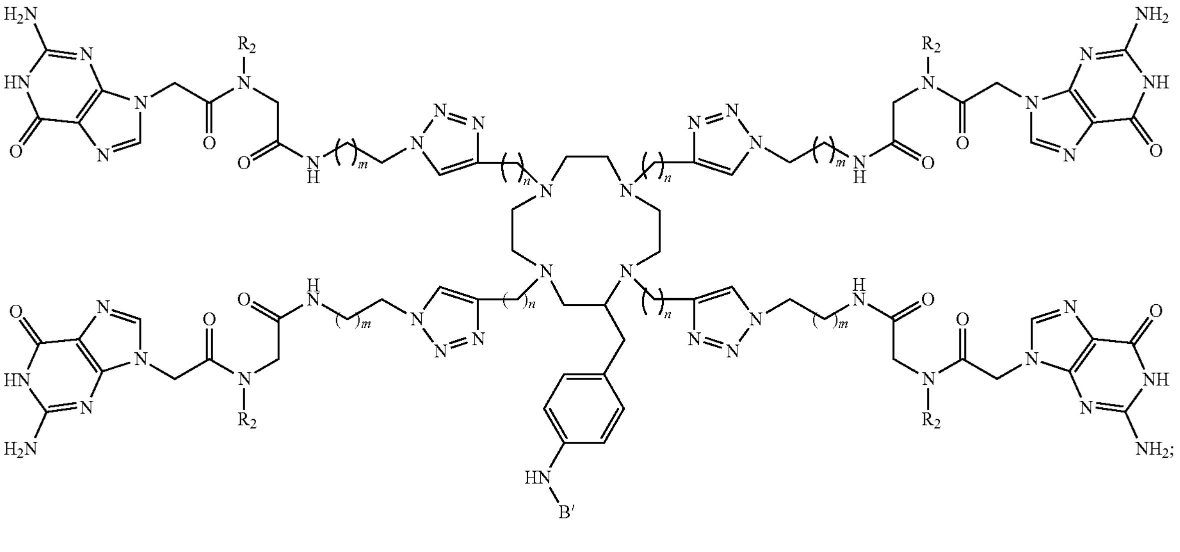

wherein n varies from 0 to 5;
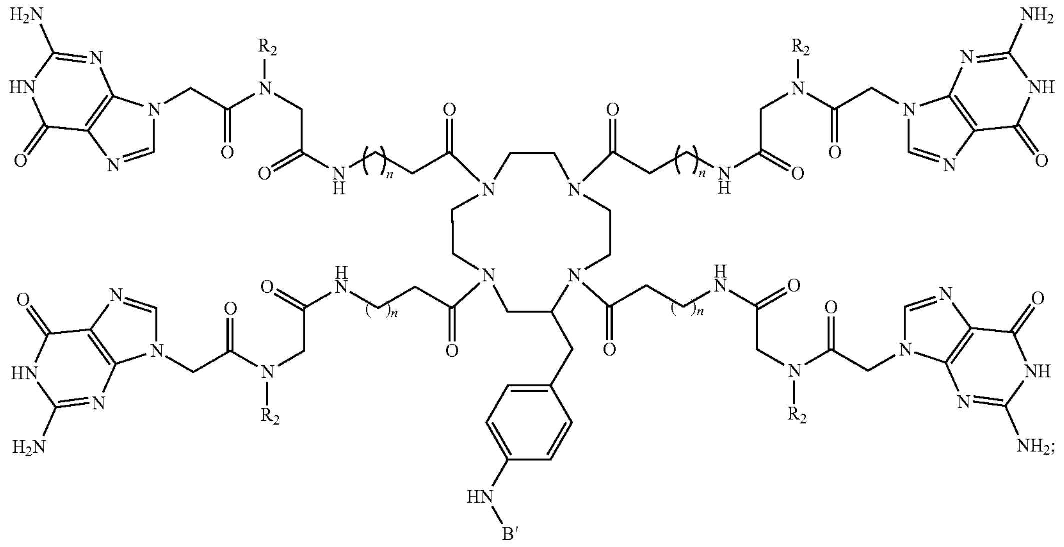
wherein n varies from 0 to 5; and
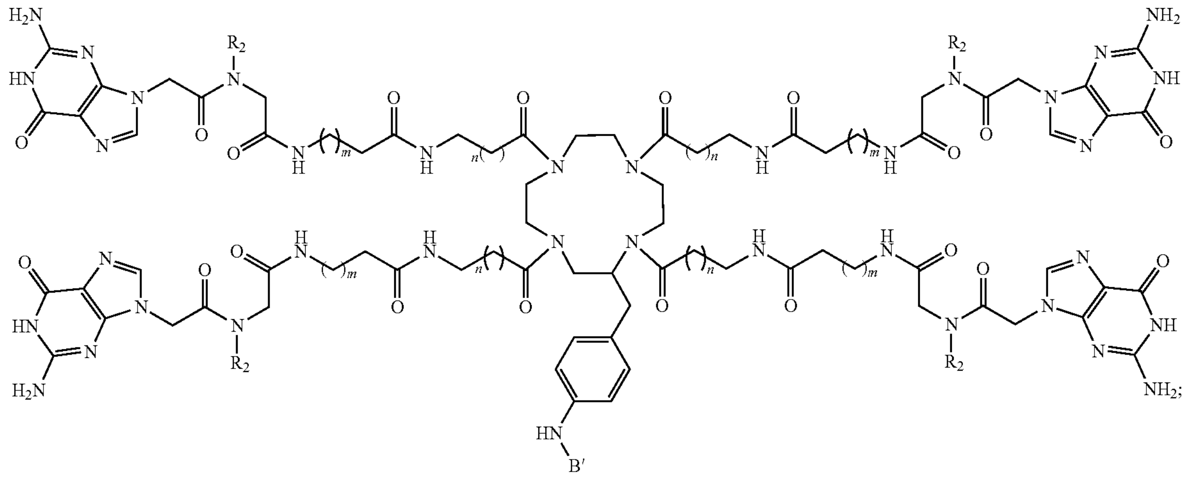
wherein n varies from 0 to 5 and m varies from 1 to 3.

More advantageously, the invention relates to the compound as defined above, of formula IV:
(IV)
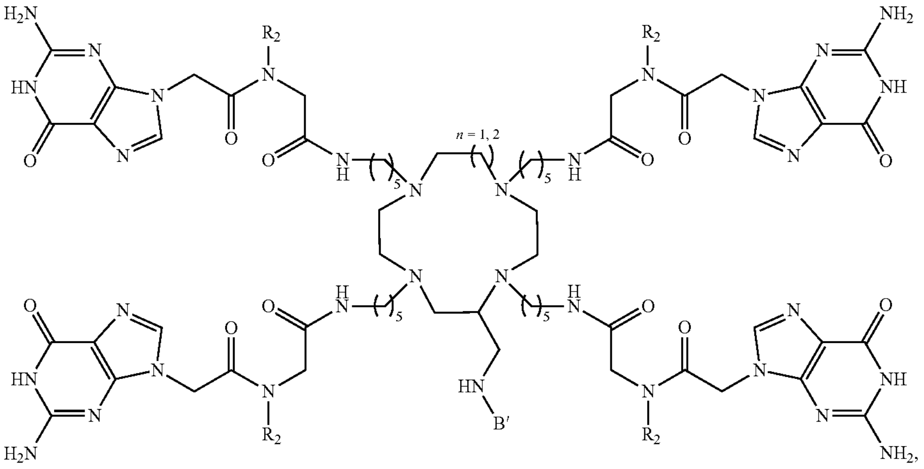
wherein B' is —(CO)—$(CH_2)_m$-T, m varying from 1 to 6, and R2 is as defined above,
preferably a compound of formula IVa
(IVa)
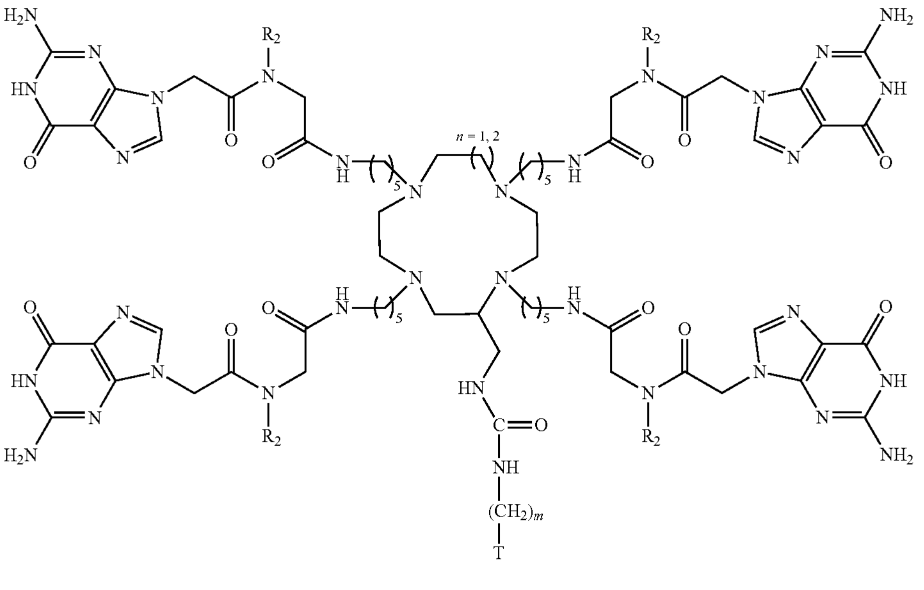

in particular the compound of formula IVb:
(IVb)
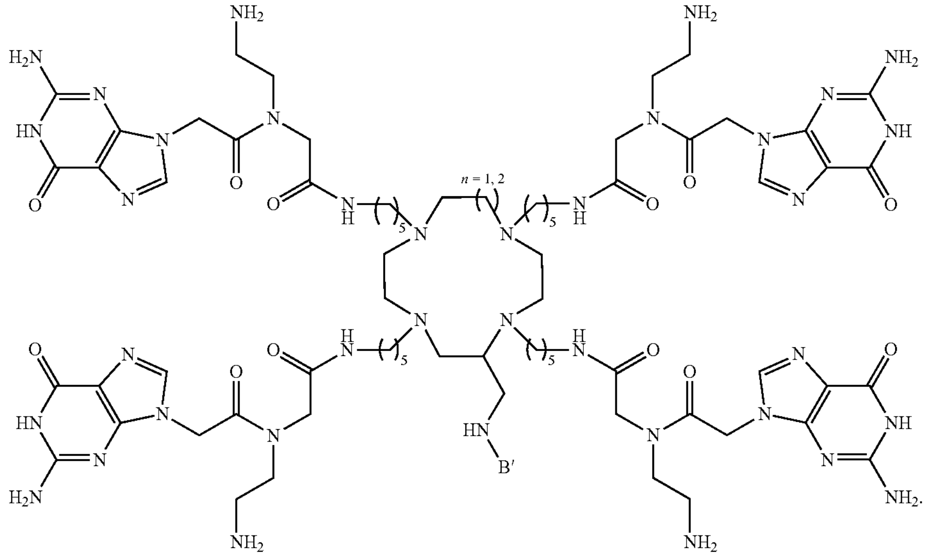
More advantageously, the invention relates to the compound as defined above, of formula V:
(V)
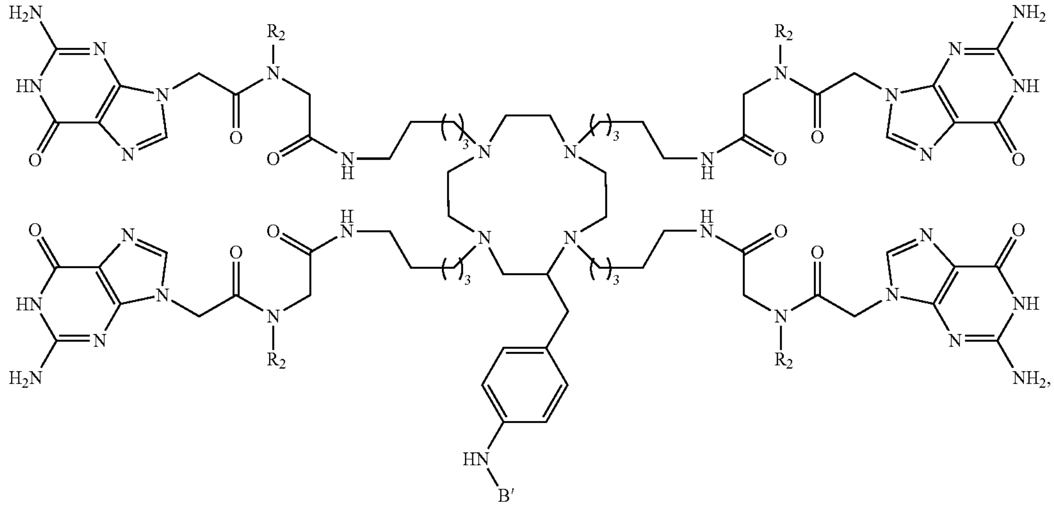

wherein B' is —(CO)—$(CH_2)_m$-T, m varying from 1 to 6, and R2 are as defined above,
in particular the compound of formula Va:
(Va)
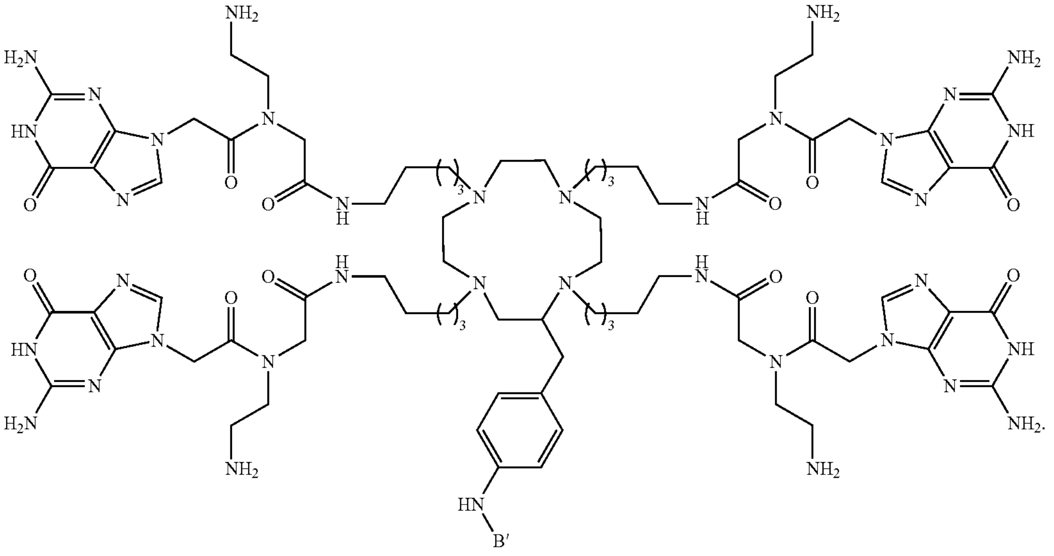
The invention relates advantageously to the compound as defined above, having one of the following formula
(VI)
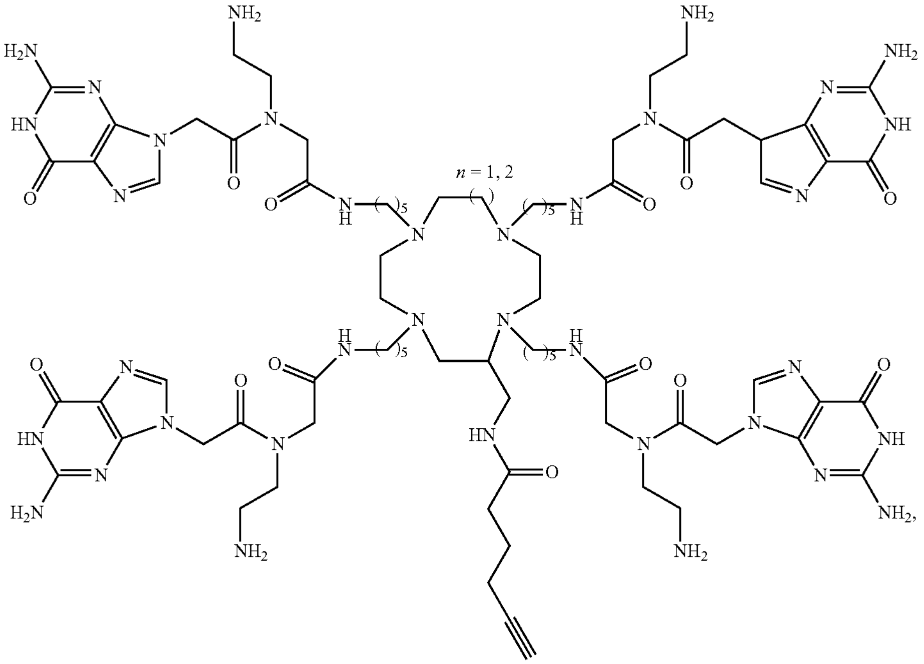

-continued
(VII)
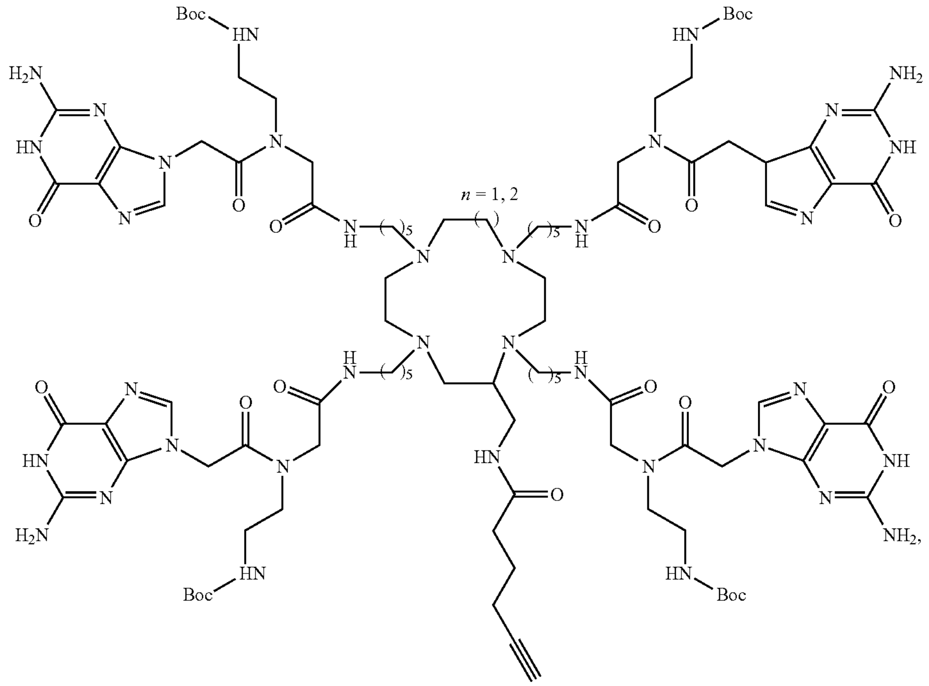
(VIII)
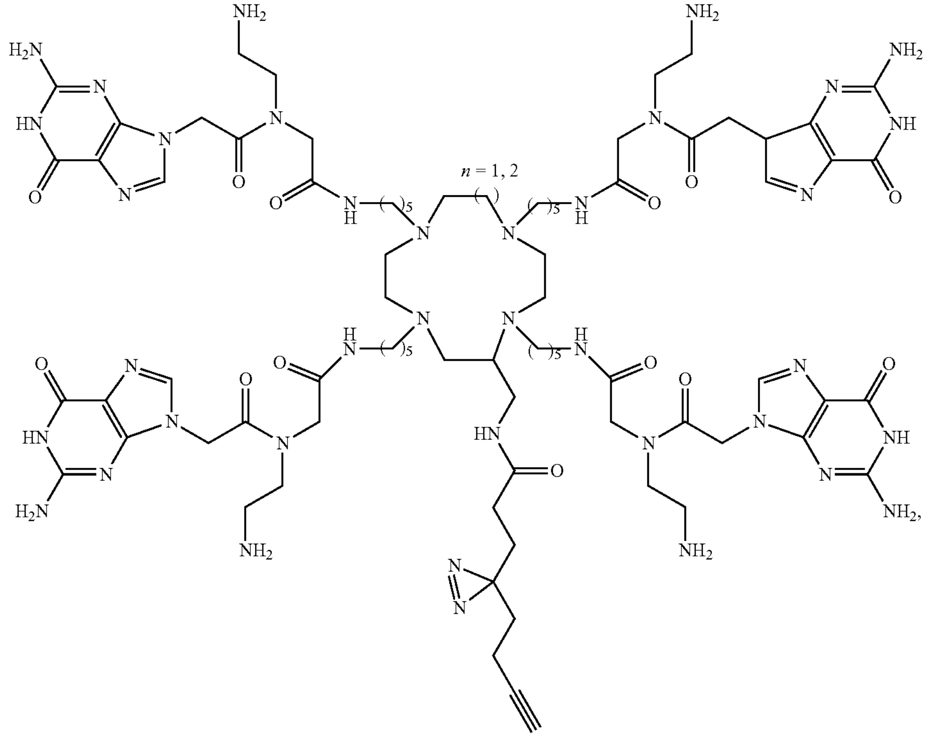

-continued
(IX)
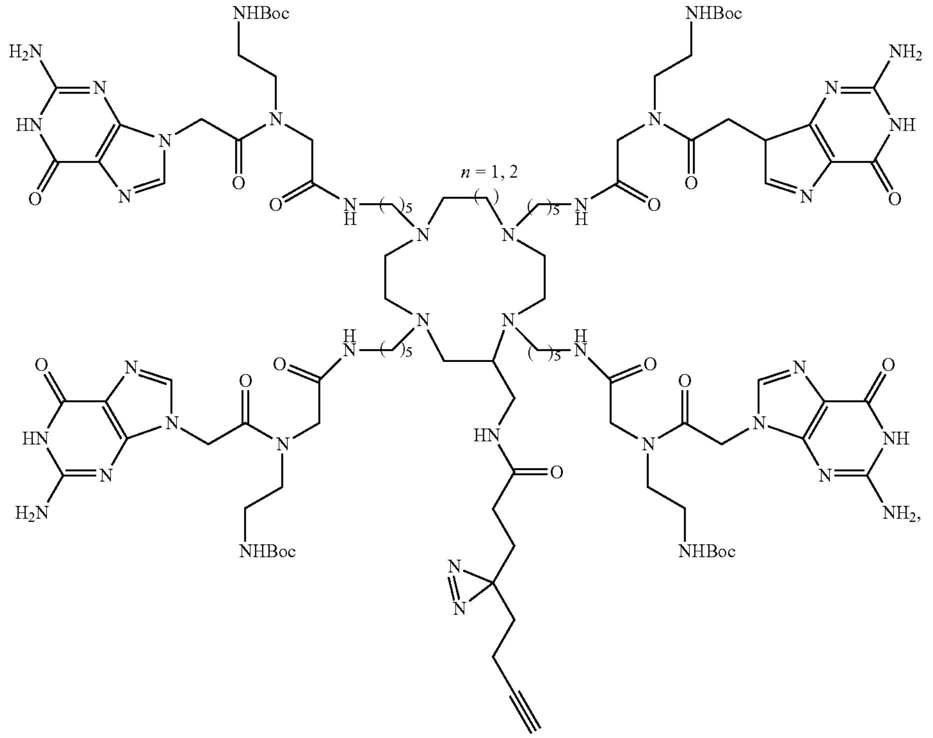
(X)
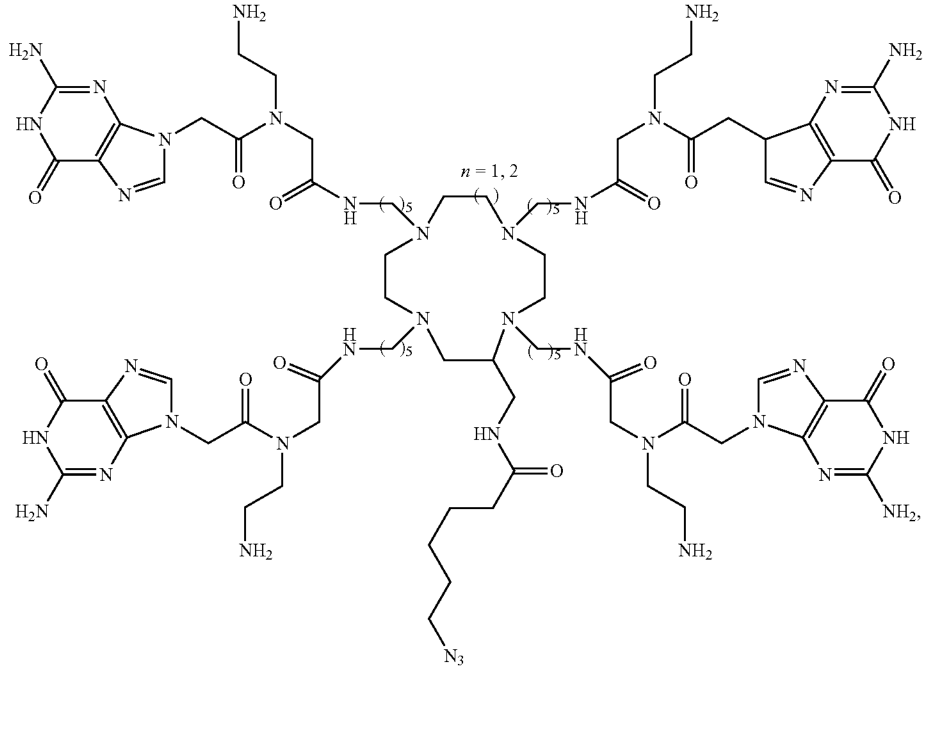

-continued
(XI)
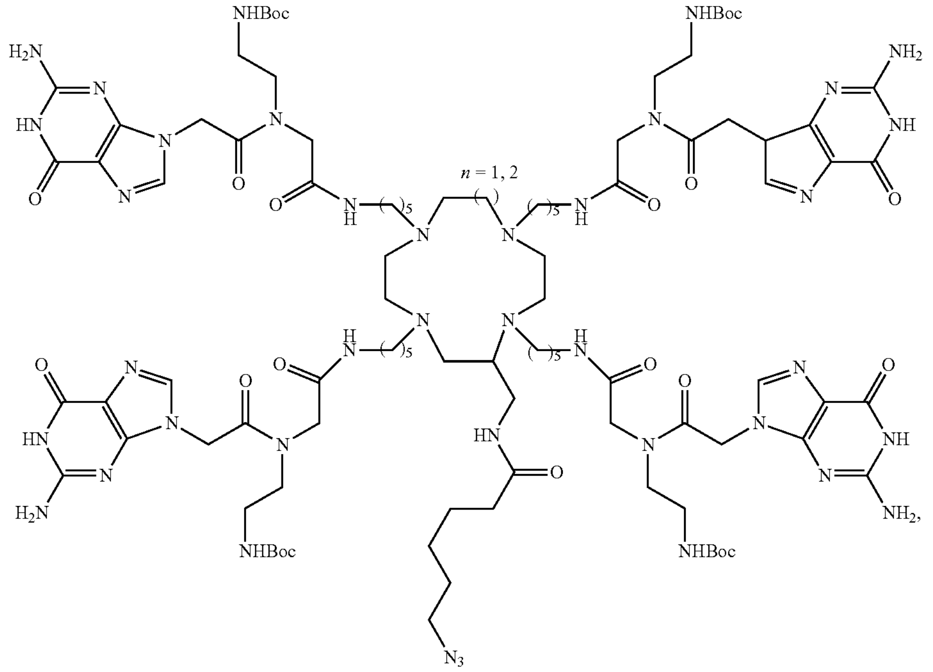
(XII)
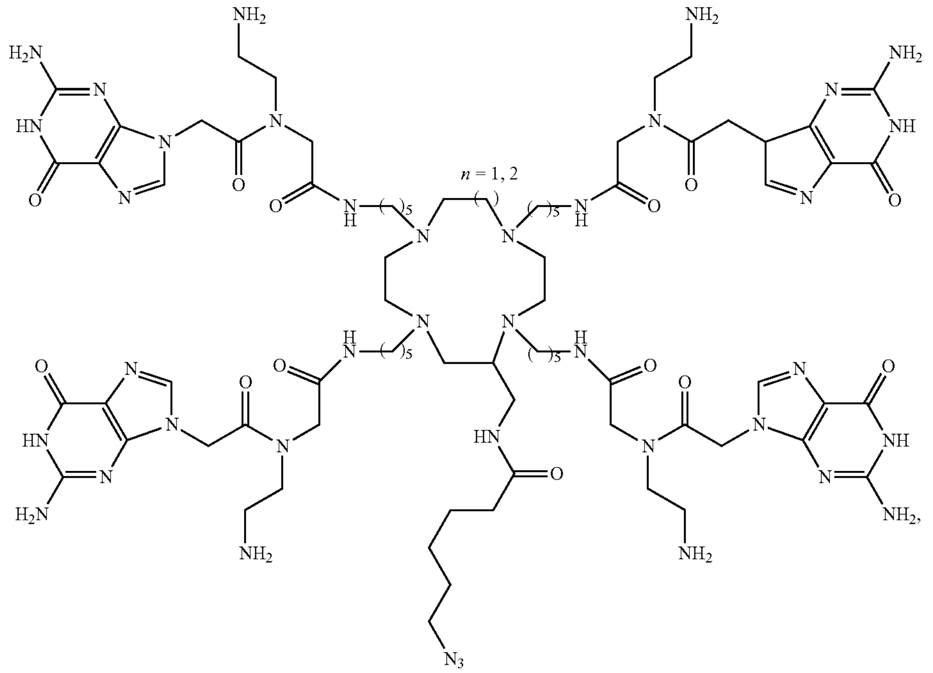

-continued
(XIII)
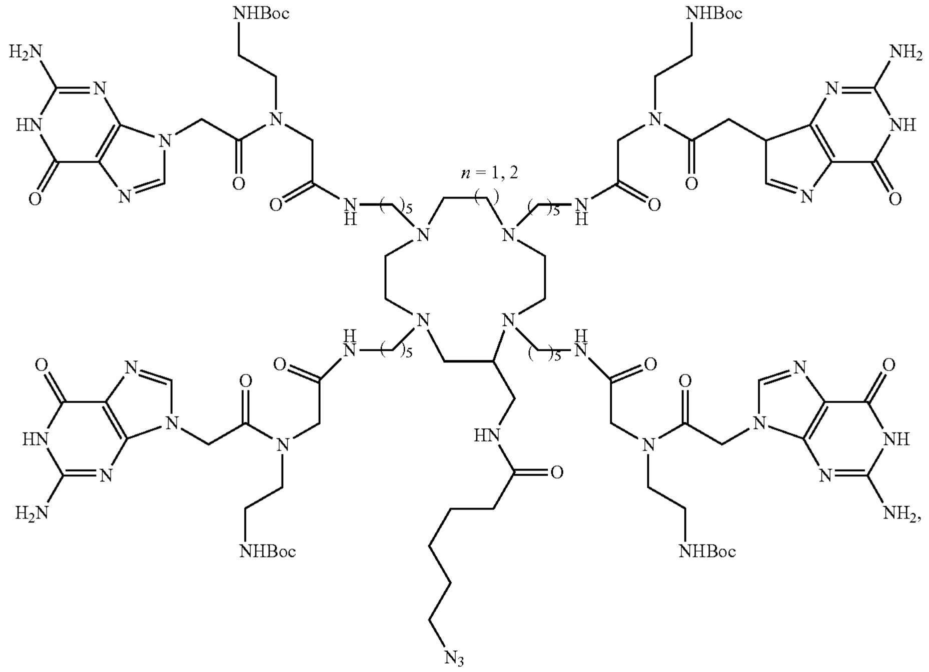
(XIV)
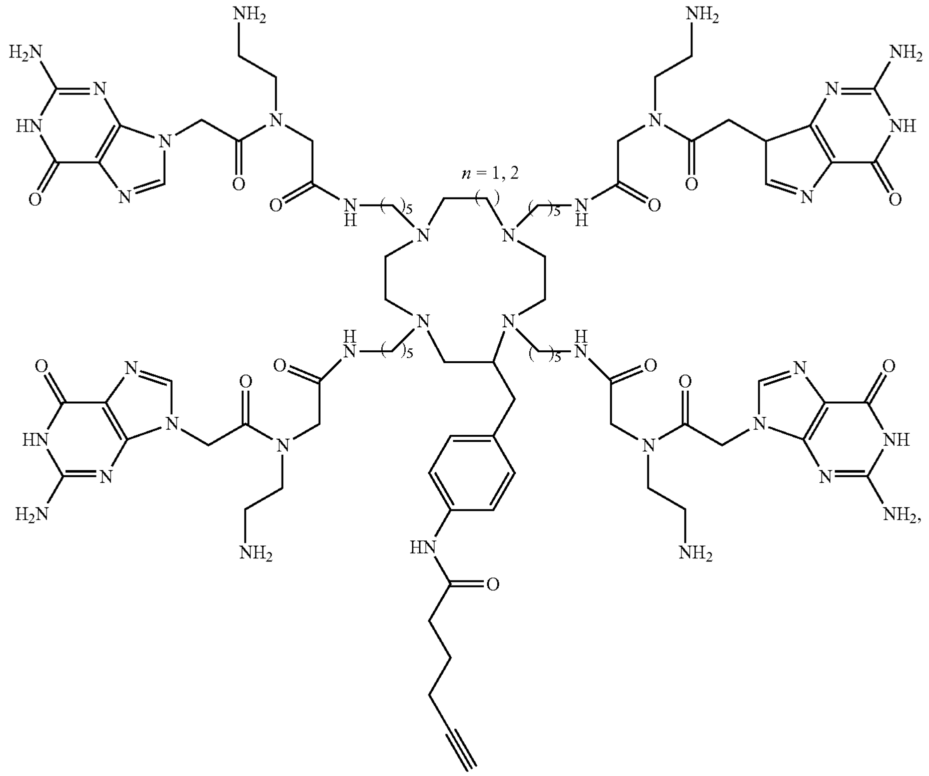

-continued
(XV)
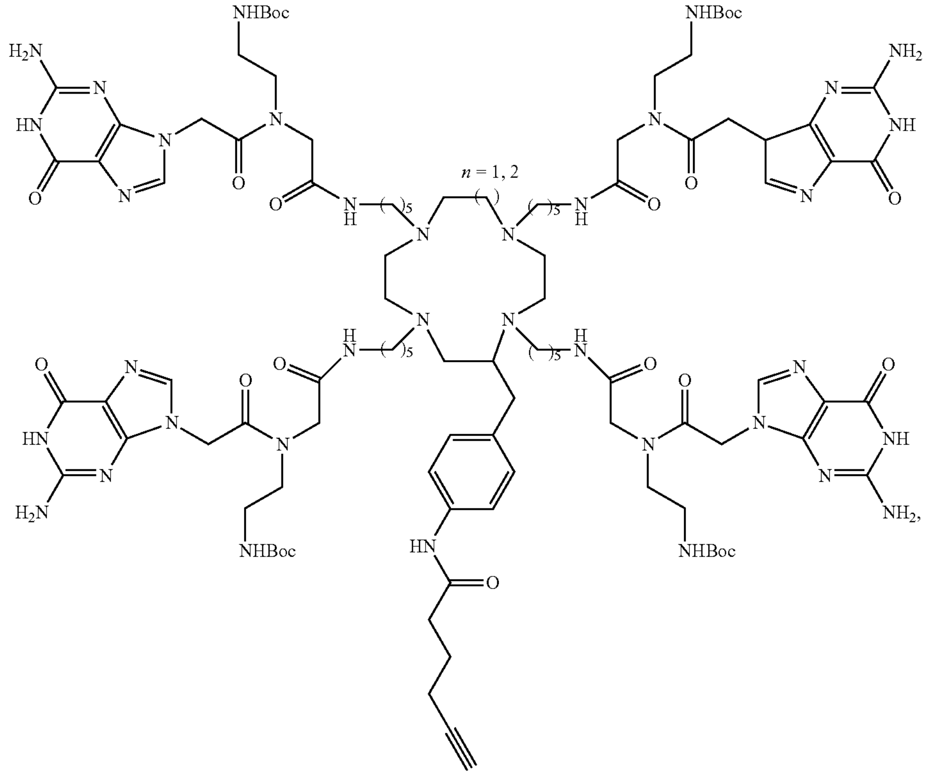
(XVI)
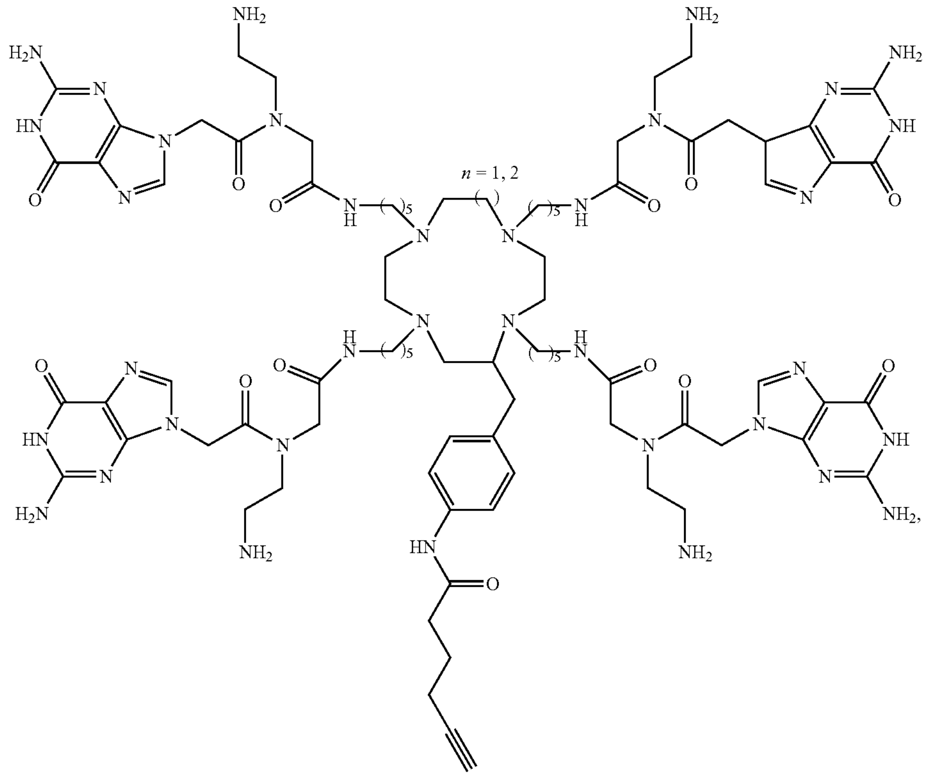
and

-continued
(XVII)
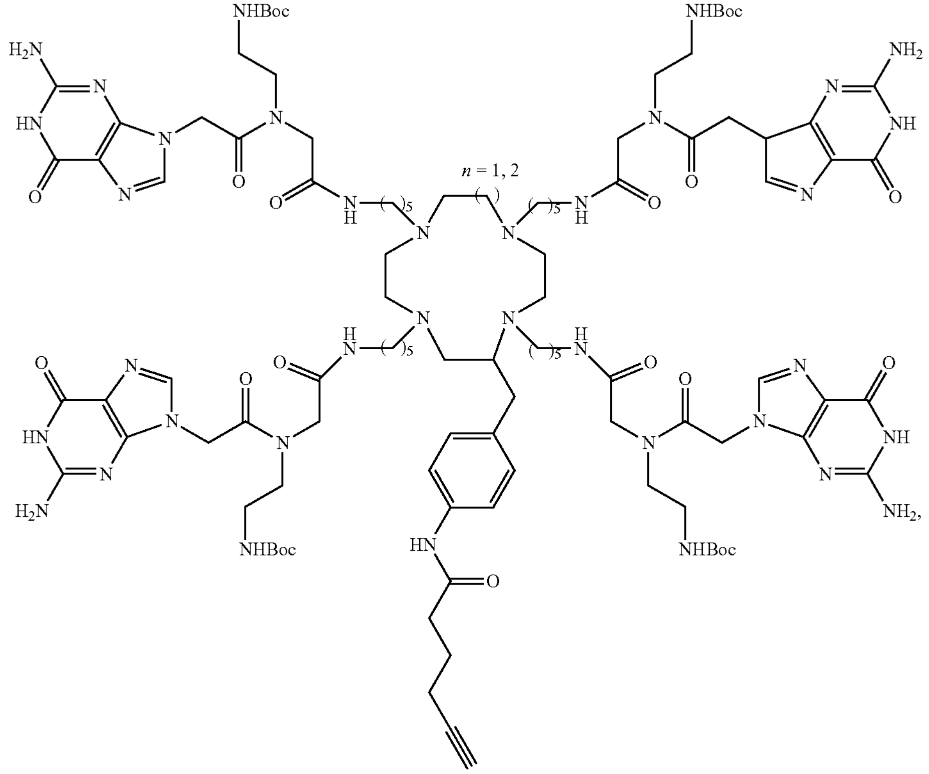
All these compounds are novel, and does not belong to the prior art.
Advantageously, the invention relates to a compound as defined above coupled by click chemistry to
Fluorescent imaging probes, such as cyanine, fluorescein, rhodamine, bodipy derivatives,
a biotin derivative, provided that said compound is not BioTASQ of formula XIX
(XIX)
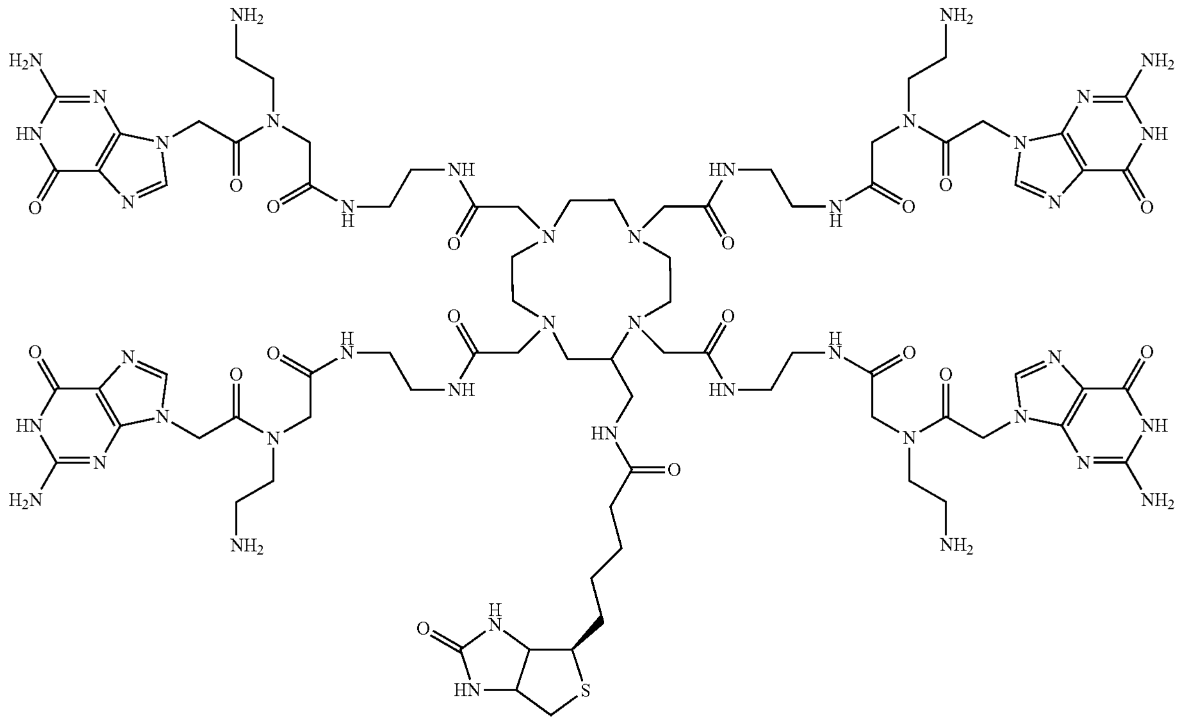

- a biological support such as for example entire antibody type biological molecules, fragments of antibodies, peptides, oligonucleotide, sugar moieties, or
- a solid support such as graphene or biochips.

The compounds defined above are link via the T moiety (or azide or alkyne moiety) to a other molecule, the linking being carried out via click chemistry.

Click chemistry defines in the invention any chemospecific and quantitative reaction that can be carried out in a biological sample, on physiological conditions.

Click chemistry involves the use of a modular approach and has important applications in the field of drug discovery, combinatorial chemistry, target-templated in situ chemistry, and DNA research. Of the reactions comprising the click chemistry scope, the pioneering example is the copper-catalyzed azide-alkyne cycloaddition to form 1,4-disubstituted-1,2,3-triazoles. The copper(I)-catalyzed reaction is mild and very efficient, requiring no protecting groups, and requiring no purification in many cases.

The azide and alkyne functional groups are largely inert towards biological molecules and aqueous environments, which allows the use of the copper-catalyzed azide-alkyne cycloaddition in target-guided synthesis and activity-based protein profiling.

The triazole has similarities to the ubiquitous amide moiety found in nature, but unlike amides, is not susceptible to cleavage. Additionally, they are nearly impossible to oxidize or reduce.

Examples of compounds resulting from the click chemistry by using the compound according to the invention can be, without limitation:

(XX)

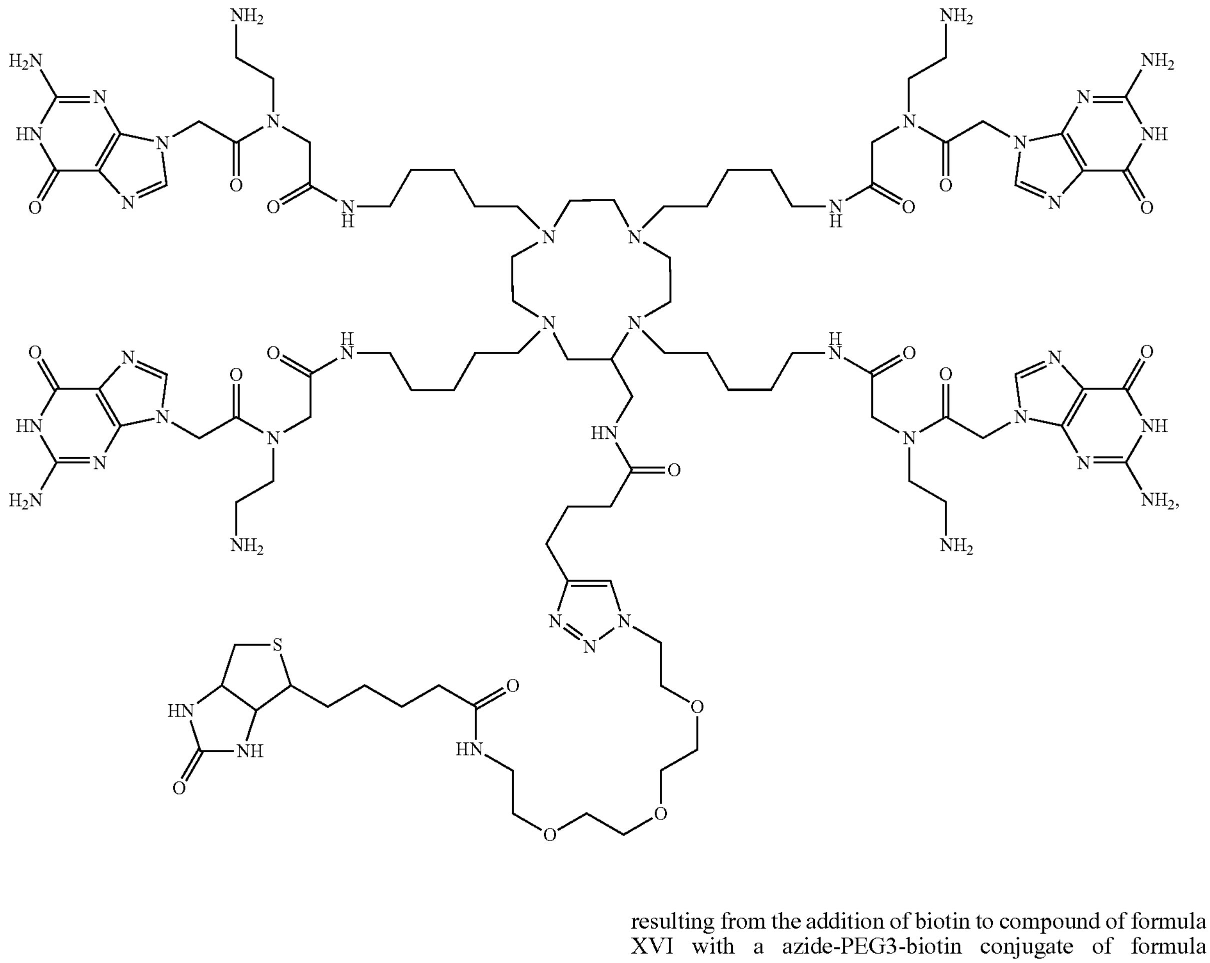

resulting from the addition of biotin to compound of formula XVI with a azide-PEG3-biotin conjugate of formula

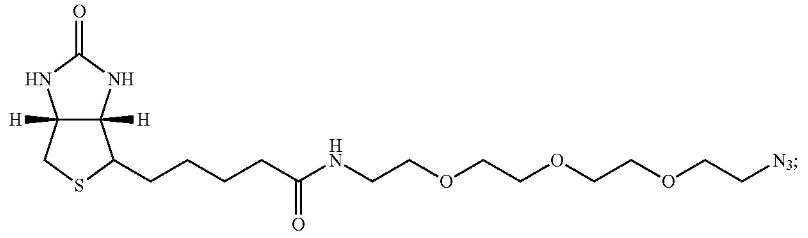;

-continued
(XXI)
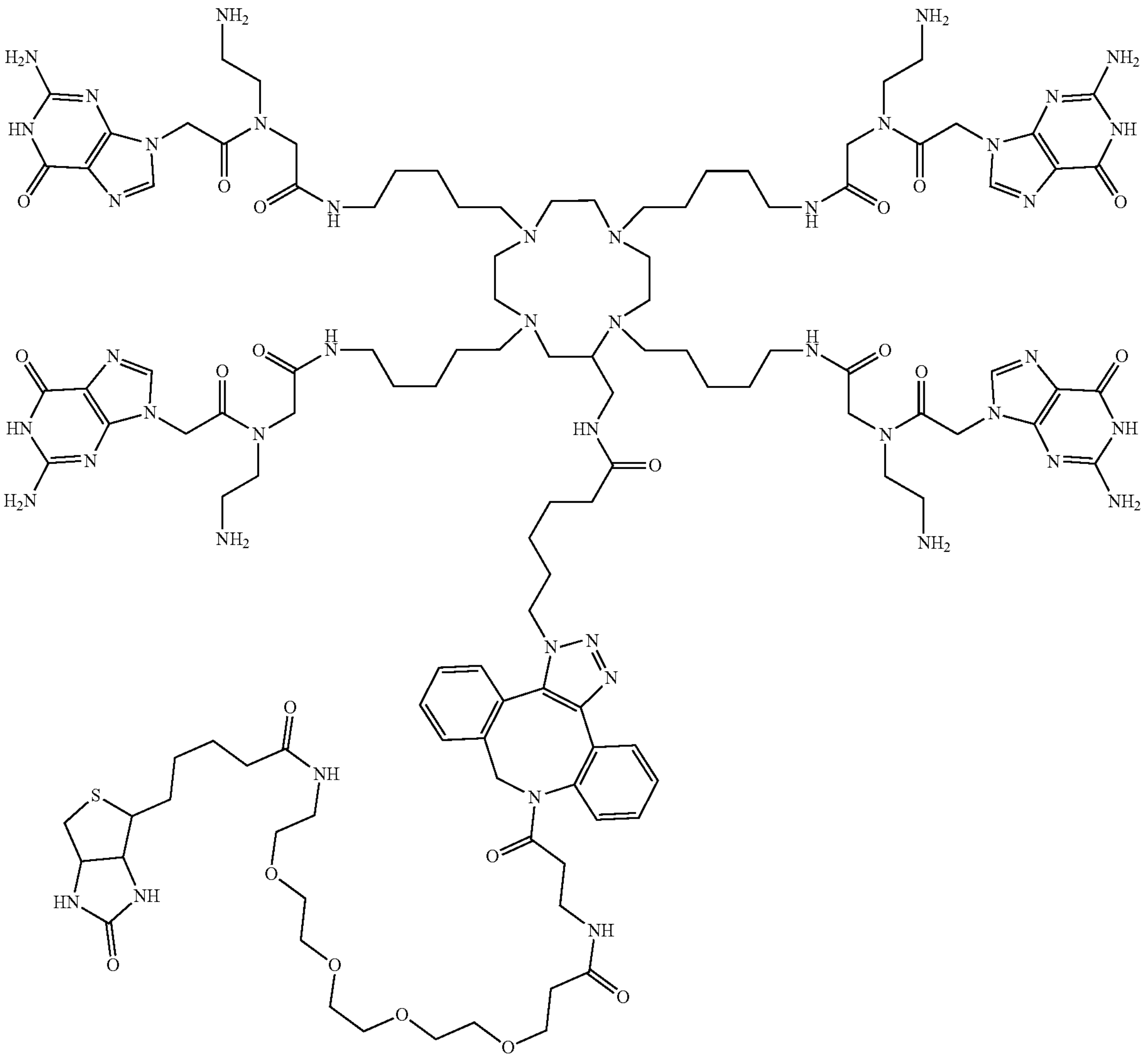

-continued
(XXII)
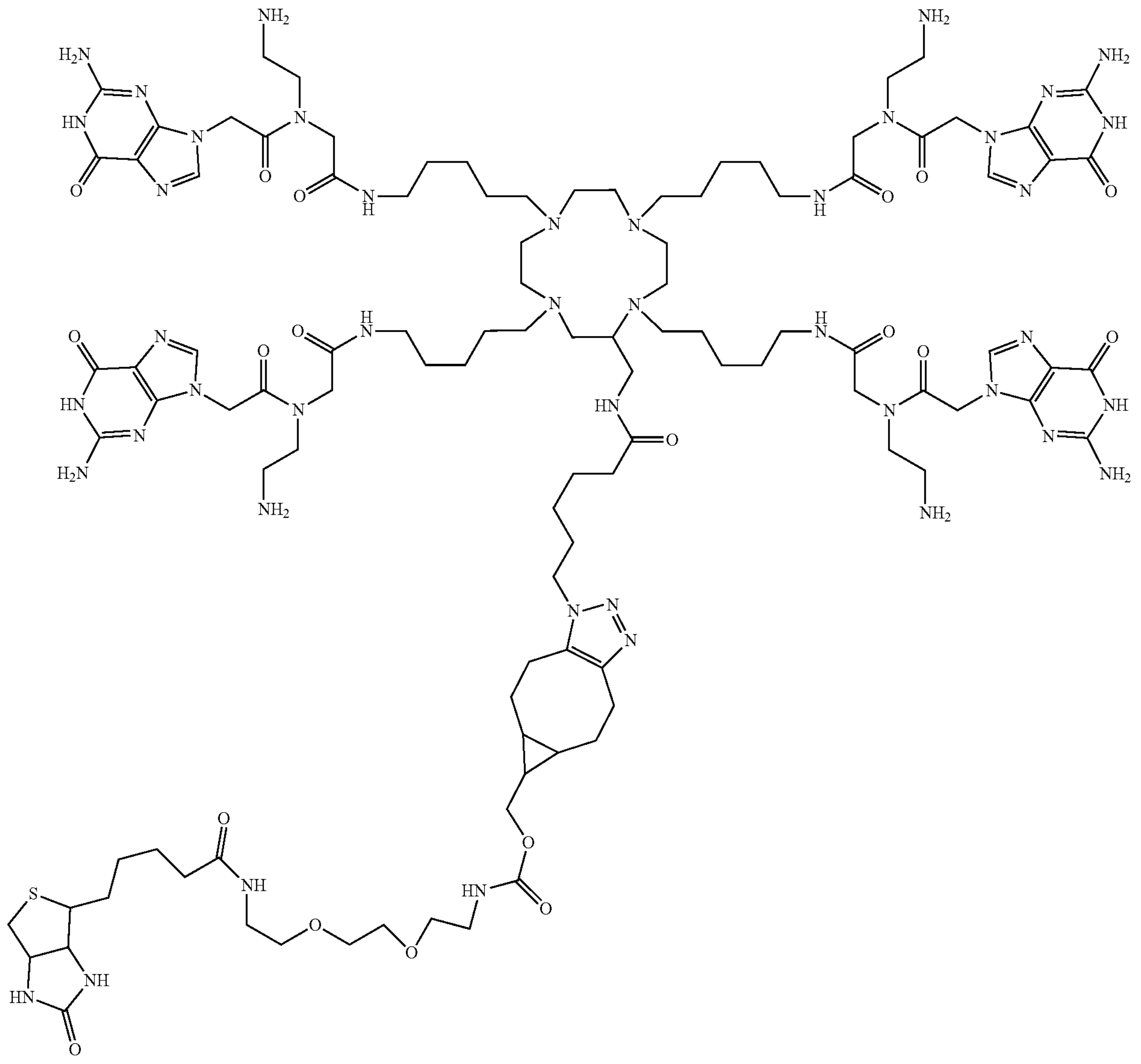

-continued (XXIII)

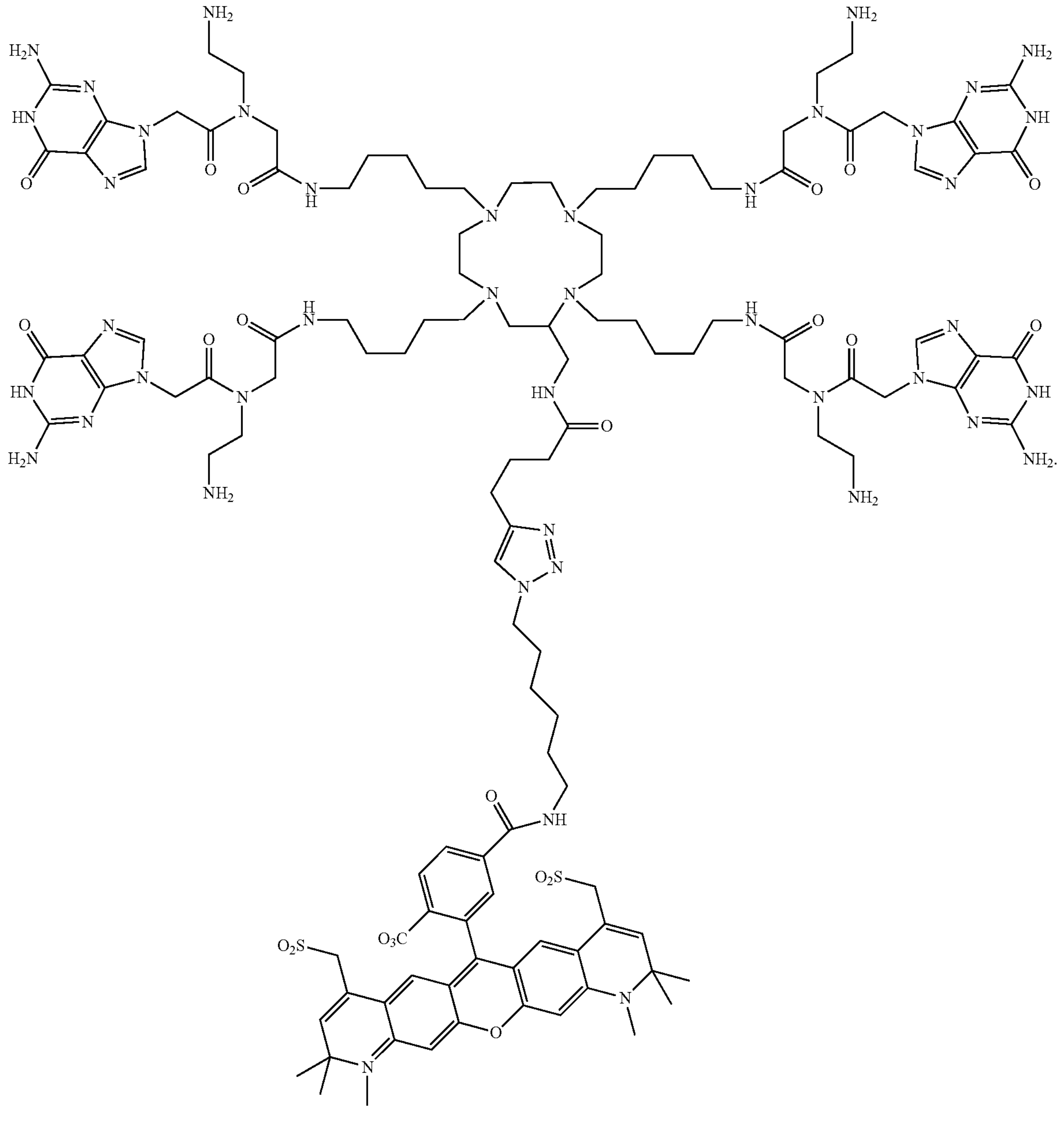

In one aspect, the invention relates to a method for detecting G-quadruplexes via the use of a suited kit combined with classical imaging techniques. In one advantageous embodiment, the invention relates to a kit comprising, consisting essentially of, or consisting of a compound according to the above-mentioned definition in association with partners allowing for performing in situ click chemistry.

The invention relates a kit comprising, consisting essentially of, or consisting of a compound according to the above-mentioned definition (MultiTASQ) in solution, in association with a compatible compound allowing click chemistry also in solution, which include (in a non-exhaustive manner) MultiTASQ plus Biotin-PEG(3)-N3, DBCO-PEG(4)-Biotin or Biotin-PEG(4)-alkyne for instance for purification purposes, and MultiTASQ plus Fluor 488-Alkyne, Cy3-alkyne or Dibenzocyclooctyne-PEG4-Fluor 545 for instance for detection purposes.

The components of the above-mentioned kit can be used simultaneously, separately or sequentially.

In one other aspect, the invention relates to a method for isolating and/or purifying G-quadruplexes, comprising a step of contacting a G-quadruplex structure with a compound as defined above.

As mentioned above, the compounds according to the invention (MultiTASQ) are able to interact with G-quadruplex structures, forming a complex that could be isolated and/or purified.

As the compounds according to the invention contain a moiety allowing to carry out click chemistry, it is possible add a compound according to the invention that allows for isolation or purification, including a biotin or a derivative, proteins such as Glutathione-S-transferase (GST), or protein tags such as Myc tag, VSVG-tag, His-tag, Ha-tag, Flag-tag . . . this list is not limitative and the skilled person could easily determine which molecule would have to be "clicked" to the compound according to the invention in order to allow the purification of the said compound, and therefore the molecule that interact with.

Depending on the mean attached to the compound according to the invention, the skilled person could carry out the steps allowing an isolation and/or a purification.

The invention relates also to the use of a compound as defined above in order to purify, in particular in vitro, a G-quadruplex forming sequence.

The invention also relates to a method for identifying molecules for in vitro, in vivo and/or ex vivo imaging, comprising a G quadruplex structure, said method comprising a first step of contacting a G-quadruplex to be identified/purified with a compound as defined above, and a step of coupling said compound with a fluorophore, a biotin derivative, a solid or biological support.

In situ click-based detection method involving compounds according to the invention, allows for detecting G4 structures in cells. The method is based on live- or post-fixation incubation of cells with the compounds of invention, followed by a click chemistry step according to the invention.

The invention relates also to the use of a compound as defined above for identifying molecules for in vitro, in vivo and/or ex vivo imaging, comprising a G quadruplex structure.

BRIEF DESCRIPTION OF THE DRAWING

FIG. 1 represents FRET-melting curves of experiments performed with the doubly labelled quadruplex F21T (0.2 μM) in Caco.K buffer without (black curves—A) or with 5 molar equivalents of TASQ (gray curves: $^{PNA}$DOTASQ (D): R═—H, X═—CONH—; BioTASQ (C): R═—$CH_2$—NHCO—$(CH_2)_4$—$C_5H_7N_2OS$; X═—CONH; and MultiTASQ (B): R═—$CH_2$—NHCO—$(CH_2)_3$—CC; X═—$CH_2$—$CH_2$—. Thermal stabilization, expressed as $\Delta T_{1/2}$ (in ° C.) are indicated for each TASQ (BioTASQ: 2.2° C., MultiTASQ: 8.9° C. and $^{PNA}$DOTASQ: 9.1° C.). Y-axis: Normalized FAM expression; X-axis: Temperature in ° C. ***: FRET.

FIG. 2 represents optical images of MCF-7 cells untreated (control: 1) or live-incubated with MultiTASQ (100 μM, 2-4: fields 1, 2 and 3; a-d: zooms from fields 1, 2 and 3) after fixation (PFA) and in situ click reactions performed with AlexaFluor488-azide® (1 μM) catalyzed by copper ($CuSO_4$, 4 mM). Nuclei are counterstained with DAPI (light gray); accumulation of MultiTASQ highlighted by arrows in zooms a-d.

FIG. 3 represents a graph showing the normalized FAM emission of a probe FAM-myc-TAMRA (F-myc-T) over the temperature (° C.; X-axis) of the probe (A), Multi TASQ-compound VII (B) and MultiTASQ-compound VIII (C).

FIG. 4 represents a graph showing the normalized FAM emission of a probe FAM-duplex-TAMRA (F-duplex-T) over the temperature (° C.; X-axis) of the probe (A), MultiTASQ-compound VII (B) and MultiTASQ-compound VIII (C).

FIG. 5 represents a graph showing the normalized FAM emission of a probe FAM-VEGF-TAMRA (F-VEGF-T) over the temperature (° C.; X-axis) of the probe (A), MultiTASQ-compound VII (B) and MultiTASQ-compound VIII (C).

FIG. 6 represents three graphs showing the HPLC traces (monitored at 488 nm) of AlexaFluor488-azide® alone (upper panel, retention time=3.86 min), of MultiTASQ-compound VII alone (central panel, no absorbance) and of the mixture of the two compounds in presence of $CuSO_4$ (a new product is formed with a retention time=2.89 min).

DETAILED DESCRIPTION

Examples

Example 1—Synthesis of Compounds According to the Invention

A-MultiTASQ-compound VII
Boc-PNAG-OH

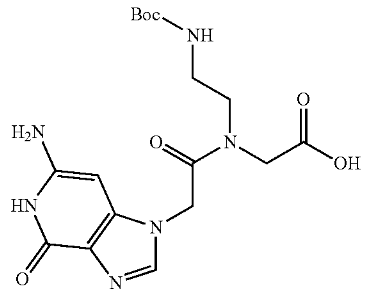 [SMILES: CC(C)(C)OC(=O)NCCN(CC(=O)O)C(=O)Cn1cnc2c(=O)[nH]c(N)cc21]

To a solution of Boc-$^{PNA}$G(Z)—OH (1 g, 1.84 mmol) in methanol (50 mL) was added Pd/C (39.1 mg, 20 mol %). The suspension was stirred overnight at room temperature under $H_2$. The solid was then filtered over dicalite and washed with methanol. The residue was concentrated under reduced pressure to afford Boc-$^{PNA}$G-OH as a white solid (540 mg, 1.31 mmol, 72%).

ESI-LRMS: $[M+H]^+$ m/z=410.82 (calcd. for $C_{16}H_{23}N_7O_6$:410.40). $^1H$ NMR (500 MHz, d6-DMSO): δ 1.37 (s, 9H), 3.20-3.80 (m, 4H), 3.99 (s, 2H), 4.85 (s, 2H), 6.46 (s, 2H), 6.95 (m, 1H), 7.51 (s, 1H), 10.59 (s, 1H).

5-((Tert-Butoxycarbonyl)Amino)Pentyl Methanesulfonate

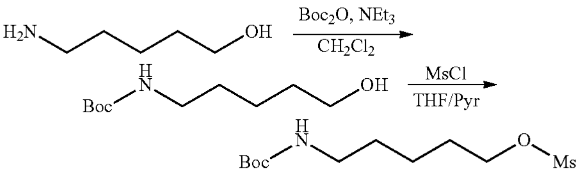

To a solution of 5-aminopentanol (1 g, 9.7 mmol) in $CH_2Cl_2$ (100 mL) was added triethylamine (1.5 mL, 10.7 mmol, 1.1 equiv.) and the solution was cooled down to 0° C. with an ice bath. Di-tert-butyl dicarbonate (2.114 g, 9.7 mmol, 1 equiv.) was added portion-wise and the solution was allowed to warm to RT and stir overnight at RT. The reaction completion was monitored and the reaction was added silica and the solvent was evaporated. The residue was purified by silica gel chromatography ($CH_2Cl_2$/MeOH 4% to 6%) to afford 5-((tert-butoxycarbonyl)amino)pentanol in 93% yield.

5-((tert-butoxycarbonyl)amino)pentanol (1 g, 4.5 mmol) was then dissolved in a mixture of THE (40 mL), pyridine was added (2 mL, 45.2 mmol, 10 equiv.), and MsCl (2 mL, 45.2 mmol, 10 equiv.) was added dropwise. The solution was allowed to stir over 48 h at RT. The THF was evaporated under vacuo, the mixture was then added 30 mL of ethyl acetate and 60 ml of acidified brine (30 mL of aq solution HCl 1M and 30 mL of brine). The aqueous phase was extracted 3 times with ethyl acetate (30 mL each), the organic phases were pooled together, dried over $MgSO_4$, filtered, and dried under vacuo. The residue was purified by silica gel chromatography ($CH_2Cl_2$/MeOH 4% to 6%) to afford 5-((tert-butoxycarbonyl)amino)pentyl methylsulfonate in 57% yield (non optimised).

1H NMR (500 MHz, Chloroform-d) δ 4.16 (t, J=6.4 Hz, 2H), 3.06 (t, J=6.4 Hz, 2H), 2.94 (s, 3H), 1.80-1.60 (m, 2H), 1.49-1.42 (m, 2H), 1.38 (s, 9H).

Aminomethylcyclene Derivative

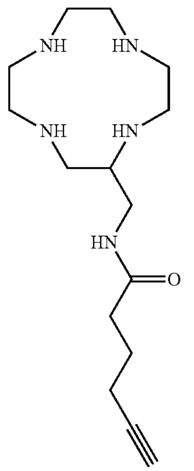 [SMILES: C#CCCCC(=O)NCC1CNCCNCCNCCN1]

To a solution of hexynoic acid (136 mg, 134 μL, 1.2 mmol, 1 equiv.) and DIPEA (315 μL, 2.4 mmol, 2 equiv.) in DMF (4 mL) was added TSTU (404 mg, 1.3 mmol, 1.1 equiv.) and the solution was allowed to stir 1 h until complete conversion of the starting material. To a solution of AMC (aminomethylcyclene) in DMF at 0° C. was added dropwise the latter reaction mixture containing N-hydroxysuccinimide hex-5-ynoate (1 mL/3 hrs). The reaction was carefully monitored by RP-HPLC and quenched by addition of TFA (466 μL, 5 equiv.) as soon as disubstituted AMC appeared in the chromatogram. The solution was then concentrated under vacuum, added water and purified by RP-HPLC in a $H_2O$/MeCN+0.1% TFA mixture (gradient of 1 to 25% over 20 minutes). After evaporation of the solvents, the AMC derivative was obtained (259 mg, 0.876 mmol, 72% yield) (exact amount of TFA not quantified).

$^1H$ NMR (500 MHz, $D_2O$): δ3.26 (d, J=5.6 Hz, 1H), 3.14-2.61 (m, 15H), 2.26 (t, J=7.4 Hz, 2H), 2.21 (t, J=2.7 Hz, 1H), 2.09 (td, J=7.0, 2.7 Hz, 2H), 1.65 (td, J=7.4, 7.0 Hz, 2H). $^{13}C$ NMR (151 MHz, $D_2O$): δ177.04, 162.83, 162.60, 119.09, 117.16, 115.23, 84.58, 69.91, 52.26, 46.42, 44.34, 44.18, 43.89, 42.67, 42.08, 40.51, 39.01, 34.38, 23.75, 17.04. ESI-HRMS: $[M+H]^+$ m/z=296.2434 (calcd. for $C_{15}H_{30}N_5O$: 296.2450).

Compound 19

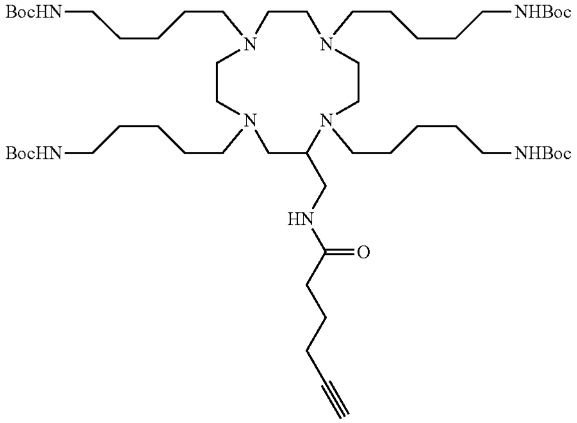 [SMILES: C#CCCCC(=O)NCC1CN(CCCCCNC(=O)OC(C)(C)C)CCN(CCCCCNC(=O)OC(C)(C)C)CCN(CCCCCNC(=O)OC(C)(C)C)CCN1CCCCCNC(=O)OC(C)(C)C]

To a solution of previously prepared AMC derivative (47.2 mg, 0.16 mmol, 1 equiv.) in MeCN (1.16 mL) was added 5-((tert-butoxycarbonyl)amino)pentyl methanesulfonate (360 mg, 1.28 mmol, 8 equiv.) and $K_2CO_3$ (176 mg, 1.28 mmol, 8 equiv.) and the solution was allowed to stir for 48 h until complete conversion of the starting material. The crude mixture was filtered, and concentrated under vacuum, added water, and purified by RP-HPLC in a $H_2O$/MeCN+0.1% TFA mixture (gradient of 1 to 100% over 20 minutes). After evaporation of the solvents, the compound 19 was obtained (75.2 mg, 0.07 mmol, 45% yield) (exact amount of TFA not quantified).

ESI-HRMS: $[M+H]^+$ m/z=1036.8098 (calc. for $C_{55}H_{105}N_9O_9$: 1035.8035).

Protected MultiTASQ—Compound VII

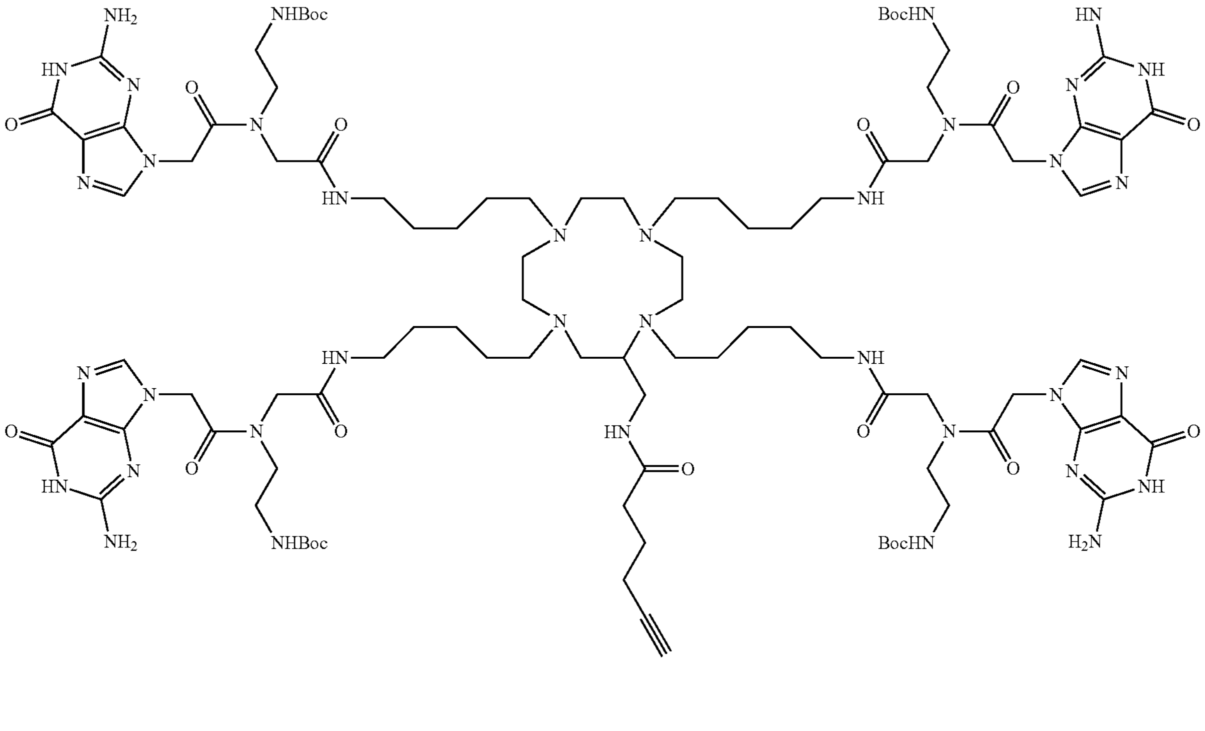 [SMILES: C#CCCCC(=O)NCC1CN(CCCCCNC(=O)CN(CCNC(=O)OC(C)(C)C)C(=O)Cn2cnc3c(=O)[nH]c(N)nc32)CCN(CCCCCNC(=O)CN(CCNC(=O)OC(C)(C)C)C(=O)Cn2cnc3c(=O)[nH]c(N)nc32)CCN(CCCCCNC(=O)CN(CCNC(=O)OC(C)(C)C)C(=O)Cn2cnc3c(=O)[nH]c(N)nc32)CCN1CCCCCNC(=O)CN(CCNC(=O)OC(C)(C)C)C(=O)Cn1cnc2c(=O)[nH]c(N)nc21]

A solution of compound 19 was stirred with 2 ml of TFA during 1 hour. After evaporation of the TFA, the unprotected compound 19 was obtained 78.5 mg, 0.072 mmol, 100% yield) (exact amount of TFA not quantified). HPLC-MS profiles page 33). Boc-$^{PNA}$G-OH (145.55 mg, 0.35 mmol, 4.5 equiv.) and TSTU (107.04 mg, 0.35 mmol, 4.5 equiv.) were dissolved in DMF (1 mL), DIPEA was added (61 µL, 4 equiv.). After 1 hour, a solution of the deprotected AMC derivative (70.2 mg, 0.09 mmol, 1 equiv.) and DIPEA (61 µL, 4 equiv.) in DMF (1 mL) was added to the mixture. The mixture was stirred at RT for 3 days. The solution was then concentrated under vacuum, added water (2 mL), and purified by RP-HPLC in a $H_2O$/MeCN+0.1% TFA mixture (gradient of 1 to 50% over 20 minutes). After evaporation of the solvents, the compound protected MultiTASQ was obtained (14.3 mg, 0.006 mmol, 8% yield) (exact amount of TFA not quantified).

ESI-HRMS: $[M+H]^+$ m/z=2202.2475 (calc. for $C_{99}H_{157}N_{37}O_{21}$: 2201.2427). $^1H$ NMR (500 MHz, DMSO-$d_6$): δ 10.80-10.62 (m, 4H), 8.09 (s, 3H), 7.86 (d, J=19.7 Hz, 2H), 7.59 (s, 3H), 6.48 (s, 8H), 4.95 (s, 3H), 4.79 (d, J=10.1 Hz, 3H), 4.17 (s, 2H), 4.10 (s, 2H), 3.90 (s, 2H), 3.86 (s, 3H), 3.71 (s, 2H), 3.61 (m, 4H), 3.46 (s, 3H), 3.26 (d, J=7.0 Hz, 2H), 3.21 (d, J=7.0 Hz, 5H), 3.13 (m, 7H), 3.03 (d, J=12.3 Hz, 8H), 2.97 (s, 4H), 2.88 (s, 3H), 2.79-2.70 (m, 5H), 2.68 (s, 2H), 2.60-2.51 (m, 9H), 2.17 (d, J=17.0 Hz, 4H), 1.72-0.98 (m, 64H).

MultiTASQ—Compound VII

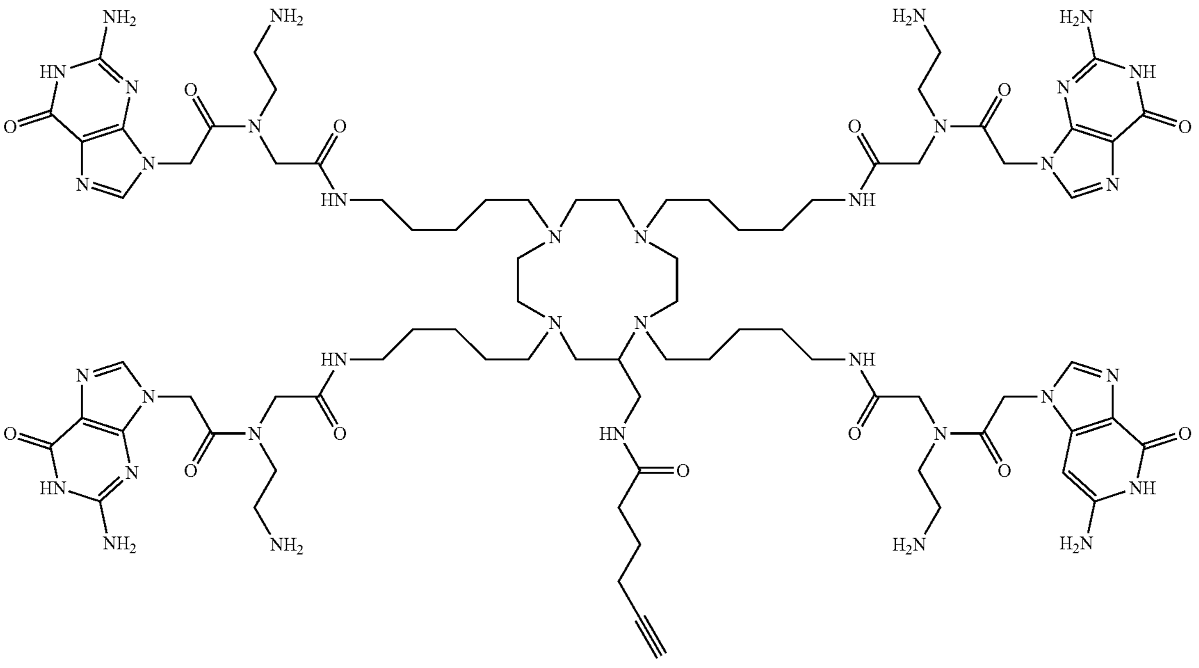 [SMILES: C#CCCCC(=O)NCC1CN(CCCCCNC(=O)CN(CCN)C(=O)Cn2cnc3c(=O)[nH]c(N)nc32)CCN(CCCCCNC(=O)CN(CCN)C(=O)Cn2cnc3c(=O)[nH]c(N)nc32)CCN(CCCCCNC(=O)CN(CCN)C(=O)Cn2cnc3c(=O)[nH]c(N)nc32)CCN1CCCCCNC(=O)CN(CCN)C(=O)Cn1cnc2c(=O)[nH]c(N)cc21]

The protected MutiTASQ was stirred with 2 mL of TFA during 1 hour. After evaporation of the TFA, tituration in diethyl ether and drying under reduced pressure, the desired compound MultiTASQ was obtained 11 mg, 0.0064 mmol, 100% yield (exact amount of TFA not quantified). ESI-HRMS: $[M+2H]^{2+}$ m/z=901.0192 (calc. for $C_{79}H_{125}N_{37}O_{13}$: $[M+2H]^{2+}$=901.0128).

→ Of note, Freshly prepared MultiTASQ aliquots must be prepared just before used. Protected MultiTASQ is the privileged form for being stored.

B-MultiTASQ—Compound VIII

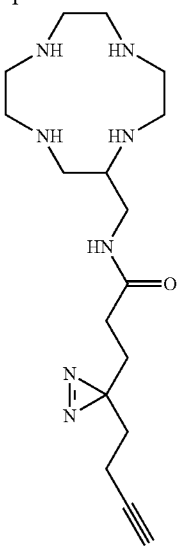

To a solution of 3-(3-But-3-yn-1yl)-3H-Diazirin-3yl) propanoic acid (17.98 mg, 0.11 mmol, 1 equiv.) and DIPEA (40 µL, 0.22 mmol, 2.1 equiv.) in DMF (3 mL) was added TSTU (44 mg, 0.14 mmol, 1.3 equiv.) and the solution was allowed to stir 1 h until complete conversion of the starting material (monitored by HPLC-MS analyses). Then, this solution was added dropwise (3 hrs) to a solution of AMC (29.3 mg, 0.14 mmol, 1.3 equiv.) in DMF (3 mL) at room temperature. Again, the reaction was carefully monitored by HPLC-MS analysis. After completion, the solution was concentrated under vacuum and the crude mixture was purified by semi-preparative HPLC in a $H_2O/CH_3CN$+0.1% TFA mixture (Jupiter Proteo 4 µm 90 Å column, 250×21.2 mm; gradient of 2 to 35% over 35 minutes, retention time: 12.5 min). After evaporation of the solvents and lyophilization, the compound was obtained with 31% yield (27 mg, 0.03 mmol).

MALDI-ToF: $[M+H]^+$ m/z=350.276 (Calcd. For $C_{17}H_{32}N_7O$: 350.266)

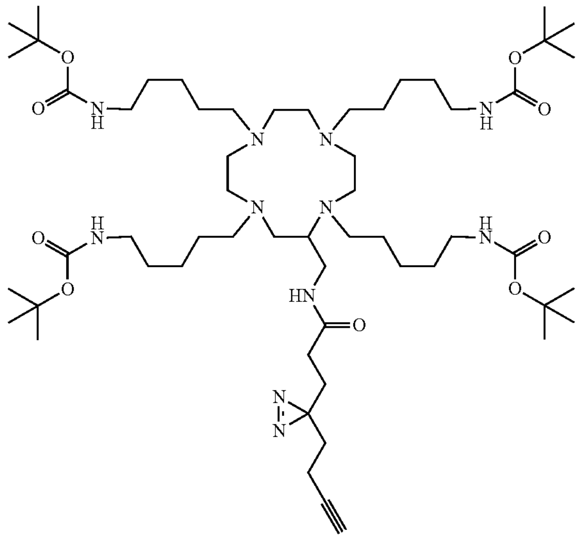 [SMILES: C#CCCC1(CCC(=O)NCC2CN(CCCCCNC(=O)OC(C)(C)C)CCN(CCCCCNC(=O)OC(C)(C)C)CCN(CCCCCNC(=O)OC(C)(C)C)CCN2CCCCCNC(=O)OC(C)(C)C)N=N1]

HPLC-MS characterization (Phenomenex Kinetex C18 column, 2.6 μm, 2.1×50 mm; from 5% to 100% $CH_3CN/H_2O$+0.1% formic acid in 7 min): retention time=0.360 min; purity: >90% at 201 nm; m/z=350.3 $[M+H]^+$.

To a solution of the previously prepared AMC derivative (34.2 mg, 0.04 mmol, 1 equiv.) in MeCN (1 μL) was added 5-((tert-butoxycarbonyl)amino)pentyl methanesulfonate (71.6 mg, 0.26 mmol, 6 equiv.) and $K_2CO_3$ (35.9 mg, 0.26 mmol, 6 equiv.). The solution was heated at 60° C. for 48 h and carefully monitored by serial HPLC-MS analyses. To improve the conversion, two additional equivalents of 5-((tert-butoxycarbonyl)amino)pentyl methanesulfonate were added and the mixture was let to stir for additional 24 h. After completion, the crude mixture was filtered, the resulting solution concentrated under vacuum and the residue purified by semi-preparative HPLC in a $H_2O/CH_3CN$+0.1% TFA mixture (Jupiter Proteo 4 μm 90 Å column, 250×21.2 mm; gradient of 5 to 60% over 50 minutes, retention time: 37 min). After evaporation of the solvents and lyophilization, the compound was obtained with 30% chemical yield (14.2 mg, 0.47 nmol).

ESI-HRMS: $[M+H]^+$ m/z=1090.83405 (calcd. for $C_{57}H_{105}N_{11}O_8$: 1090.83260).

HPLC-MS characterization (Phenomenex Kinetex C18 column, 2.6 μm, 2.1×50 mm; from 5% to 100% $CH_3CN/H_2O$+0.1% formic acid in 7 min): retention time=4.243 min; purity: >92% at 201 nm; m/z=1091.1 $[M+H]^+$.

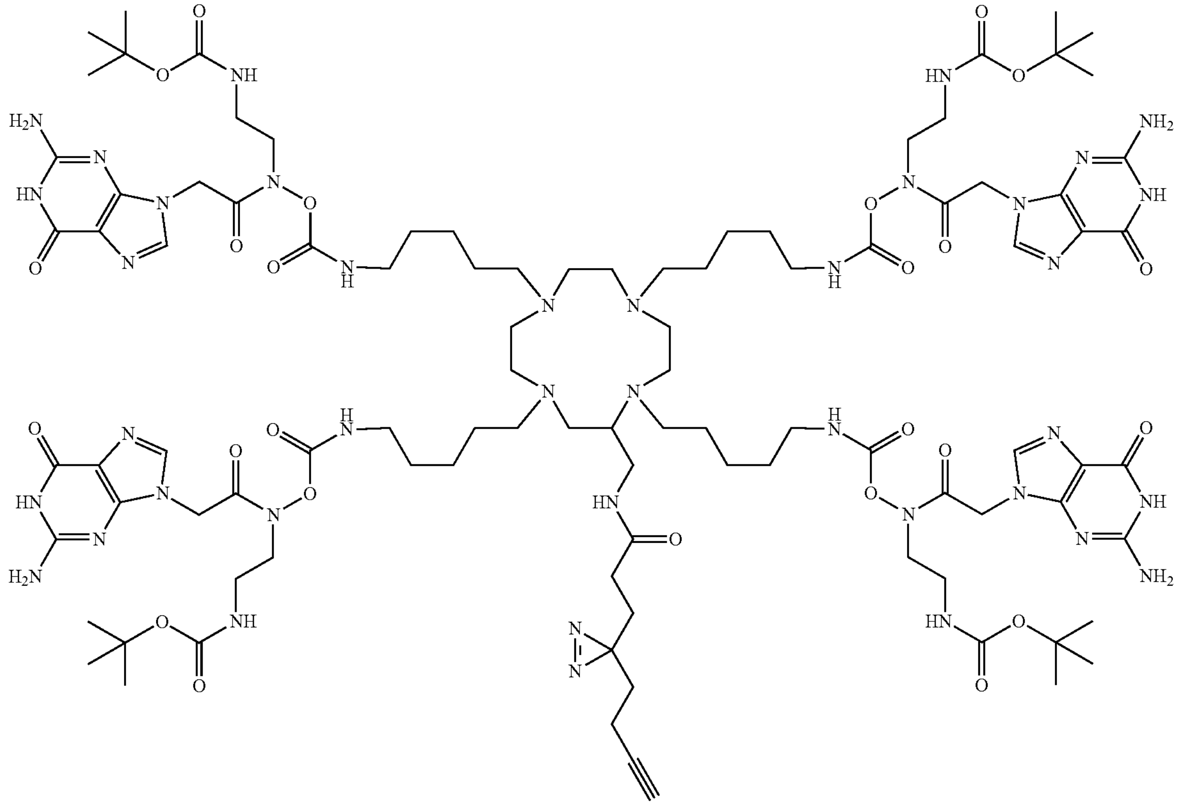 [SMILES: C#CCCC1(CCC(=O)NCC2CN(CCCCCNC(=O)ON(CCNC(=O)OC(C)(C)C)C(=O)Cn3cnc4c(=O)[nH]c(N)nc43)CCN(CCCCCNC(=O)ON(CCNC(=O)OC(C)(C)C)C(=O)Cn3cnc4c(=O)[nH]c(N)nc43)CCN(CCCCCNC(=O)ON(CCNC(=O)OC(C)(C)C)C(=O)Cn3cnc4c(=O)[nH]c(N)nc43)CCN2CCCCCNC(=O)ON(CCNC(=O)OC(C)(C)C)C(=O)Cn2cnc3c(=O)[nH]c(N)nc32)N=N1]

Protected MultiTASQ—Compound VIII

A solution of the previously prepared compound (15.1 mg, 0.014 mmol, 1 equiv.) was stirred in 500 μL TFA for 1 hour to deprotect the amines. After evaporation, the complete deprotection of the starting material was checked by HPLC-MS. The deprotected compound (9.66 mg, 0.014 mmol, 100% yield) was used without further purification. In the meantime Boc-$^{PNA}$G-OH (22.5 mg, 0.55 mmol, 4 equiv.), TSTU (19.2 mg, 0.062 mmol, 4.4 equiv.) were dissolved in DMF (1 mL) and DIPEA was added (10 μL, 4 equiv.). After 1 hour, the complete activation of the acid was assessed by HPLC-MS and the mixture was added to the solution containing the previously prepared deprotected compound (9.66 mg, 0.014 mmol, 1 equiv.) followed by the addition of DIPEA (10 μL, 4 equiv.) in DMF (1 mL). The mixture was stirred at RT for 3 days. The solution was then concentrated under vacuum, solubilized in a mixture of water and $CH_3CN$ (50/50, 2 mL), and purified by semi-preparative HPLC in a $H_2O/CH_3CN$+0.1% TFA mixture (Jupiter Proteo 4 μm 90 Å column, 250×21.2 mm; gradient of 5 to 15% over 5 min, then from 15 to 65% over 50 min, retention time: 29 min). After evaporation of the solvents, the protected MultiTASQ* was obtained in 4% chemical yield (1.36 mg, 0.56 nmol) (exact amount of TFA not quantified).

ESI-HRMS: $[M+H+Na]^{2+}$ m/z=1139.12403 (calcd. for $C_{101}H_{160}N_{39}NaO_{21}$: 1139.12689).

HPLC-MS characterization (Phenomenex Kinetex C18 column, 2.6 μm, 2.1×50 mm; from 5% to 100% $CH_3CN$/$H_2O$+0.1% formic acid in 7 min): retention time=3.680 min; purity: >99% at 280 nm; m/z=1128.7 $[M+2H]^{2+}$.

MultiTASQ—Compound VIII

The protected MultiTASQ-compound VIII (1.95 mg, 0.9 nmol) was dissolved in TFA (200 μL) and the complete deprotection was assessed via HPLC-MS analyses. After completion, the mixture was diluted in water and the compound was lyophilized to offer MultiTASQ compound VIII as a white powder (2.0 mg, 0.9 nmol, 100%).

ESI-HRMS: $[M+2H]^{2+}$ m/z=928.03214 (calcd. for $C_{81}H_{128}N_{39}O_{13}$: 928.03105).

HPLC-MS characterization (Phenomenex Kinetex C18 column, 2.6 μm, 2.1×50 mm; from 5% to 100% $CH_3CN$/$H_2O$+0.1% formic acid in 7 min): retention time=0.627 min; purity: >98% at 280 nm.

Example 2—Fret Melting Assay

Material and Methods

The lyophilized DNA strands (purchased from Eurogentec, Seraing, Belgium) were firstly diluted at 500 μM in deionized water (18.2 MΩ·cm resistivity). The DNA batch was prepared in a Caco.K buffer, comprised of 10 mM lithium cacodylate buffer (pH 7.2) plus 10 mM KCl/90 mM LiCl.

The quadruplex structure was prepared by mixing 40 μL of the constitutive strand (500 μM) with 8 μL of a lithium cacodylate buffer solution (100 mM, pH 7.2), plus 8 μL of a KCl/LiCl solution (100 mM/900 mM) and 24 μL of water. The final DNA concentration was theoretically 250 μM. The actual concentration of the DNA was determined through a dilution to 1 μM theoretical concentration through UV

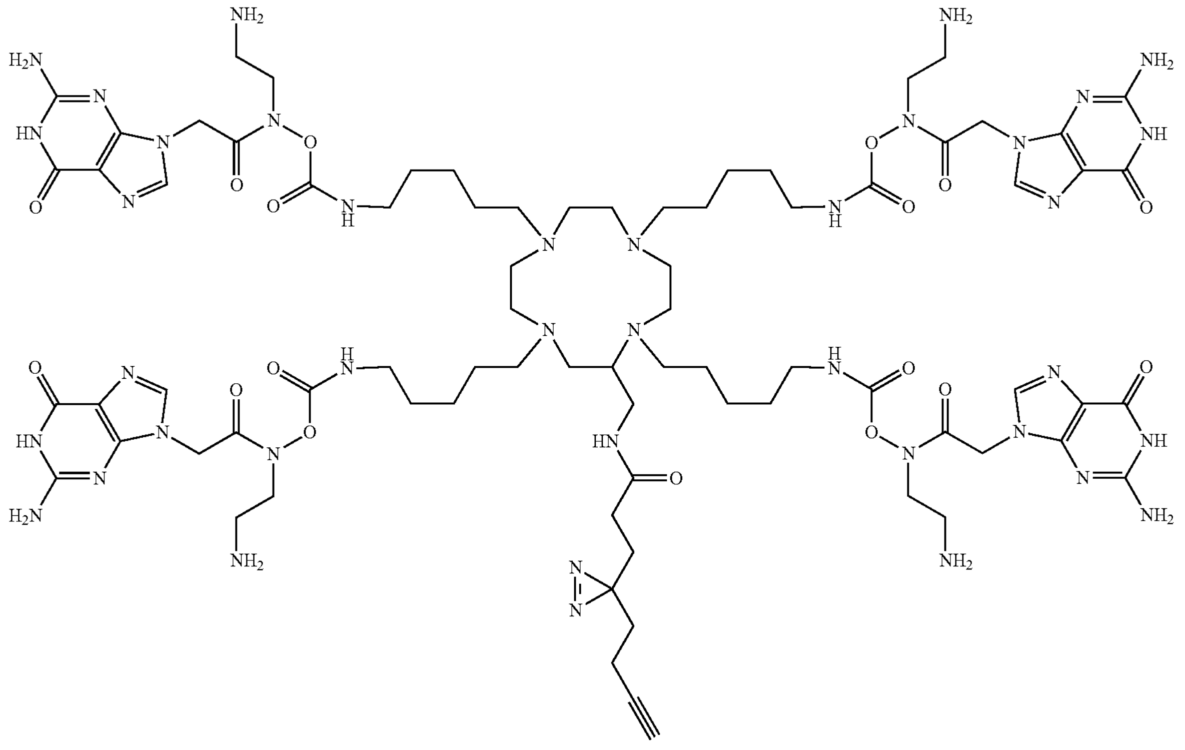 [SMILES: C#CCCC1(CCC(=O)NCC2CN(CCCCCNC(=O)ON(CCN)C(=O)Cn3cnc4c(=O)[nH]c(N)nc43)CCN(CCCCCNC(=O)ON(CCN)C(=O)Cn3cnc4c(=O)[nH]c(N)nc43)CCN(CCCCCNC(=O)ON(CCN)C(=O)Cn3cnc4c(=O)[nH]c(N)nc43)CCN2CCCCCNC(=O)ON(CCN)C(=O)Cn2cnc3c(=O)[nH]c(N)nc32)N=N1]

spectral analysis at 260 nm (after 5 min at 90° C.) with the following molar extinction coefficient values: 268300 $M^{-1}\cdot cm^{-1}$ (F21 T). The higher-order DNA structure was folded as follows: solutions were heated (90° C., 5 min), cooled on ice (7 h) and then stored at least overnight (4° C.). FRET-melting experiments were performed in a 96-well format using a Mx3005P qPCR machine (Agilent) equipped with FAM filters ($\lambda_{ex}$=492 nm; $\lambda_{em}$=516 nm) in 100 µL (final volume) of Caco.K buffer with 0.2 µM of labeled oligonucleotide and 1 µM of TASQ ($^{PNA}$DOTASQ, BioTASQ and MultiTASQ). After a first equilibration step (25° C., 30 s), a stepwise increase of 1° C. every 30 s for 65 cycles to reach 90° C. was performed, and measurements were made after each cycle. Final data were analyzed with Excel (Microsoft Corp.) and OriginPro® 9.1 (OriginLab Corp.). The emission of FAM was normalized (0 to 1), and $T_{1/2}$ was defined as the temperature for which the normalized emission is 0.5; $\Delta T_{1/2}$ values are means of 3 experiments (FIG. 1).

Results

The apparent affinity of each G4-ligands is quantified via fluorescence resonance energy transfer (FRET)-melting experiments.

$^{PNA}$DOTASQ, BioTASQ and MultiTASQ were thus assayed against the dual-labeled F-21-T FAM-d[seq]-TAMRA, wherein [seq] is $^{5'}$GGGTTAGGGTTAGGGTTAGGG$^{3'}$ (SEQ ID NO: 1), in a dose-response manner (experiments were performed with 1 and 5 µM ligand versus 0.2 µM DNA, i.e. 5 and 25 mol. equiv. ligand). Results seen in FIG. 1 show that the quadruplex-stabilizing capacity (or apparent G-quadruplex affinity) of MultiTASQ (compound according to the invention) is restored as compared to BioTASQ ($\Delta T_{1/2}$=8.9 versus 2.2° C. for MultiTASQ and BioTASQ, respectively), in a manner that is comparable to the results obtained with the parent compound $^{PNA}$DOTASQ.

Additionally, MultiTASQ-compound VII and MultiTASQ-Compound VIII (MultiTASQ*) were assayed against the dual-labeled F-Myc-T FAM-d[seq]-TAMRA, wherein [seq] is $^{5'}$GAGGGTGGGGAGGGTGGGGAAG$^{3'}$ (SEQ ID NO: 2), F-duplex-T FAM-d[seq]-TAMRA, wherein [seq] is $^{5'}$TATAGCTATATTTTTTATAGCTATA$^{3'}$ (SEQ ID NO: 3) and F-VEGF-T FAM-r[seq]-TAMRA, wherein [seq] is $^{5'}$GGAGGAGGGGAGGAGGA$^{3'}$ (SEQ ID NO: 4) at 5 µM concentration versus 0.2 µM DNA (i.e. 5 mol. equiv. ligand).

Results seen in FIGS. 3-5 show i—that the quadruplex-stabilizing capacity (or apparent G-quadruplex affinity) of both MultiTASQ and MultiTASQ* (two compounds according to the invention) are fully comparable ($\Delta T_{1/2}$=8.0 and 9.1° C. for MultiTASQ and MultiTASQ* with G-quadruplex-DNA; respectively; $\Delta T_{1/2}$=14.6 and 16.8° C. for MultiTASQ and MultiTASQ* with G-quadruplex-RNA, respectively); and ii—that both compounds are highly selective for G-quadruplex versus duplex ($\Delta T_{1/2}$ between 0 and 0.2° C.).

Example 3—Coupling MultiTASQ-Compound VII to a Fluorophore Via Click Chemistry

A 1:1 mixture (100 µM final concentration, in water) of AF488 azide (or Alexa Fluor™ 488 5-Carboxamido-(6-Azidohexanyl) bistriethylammonium salt) and MultiTASQ was stirred in presence of an excess of sodium ascorbate and $CuSO_4*5H_2O$ for 1 h at RT. The complete conversion was assessed via HPLC analyses (Phenomenex Kinetex C18 column, 2.6 µm, 2.1×50 mm; from 5% to 100% $CH_3CN/H_2O$+0.1% formic acid in 7 min): retention time of the starting material=3.857 min; of the conjugate=2.713; conversion: >99% at 488 nm.

Results seen in FIG. 6 show that AF488 azide is fully converted into a higher polarity conjugate when mixed for 1 h at room temperature with MultiTASQ-CompoundVII in presence of copper catalyst ($CuSO_4$) and sodium ascorbate, likely through an azide-alkyne Huisgen cycloaddition between the azide moiety of AlexaFluor488-azide® and the alkyne appendage of MultiTASQ-compound VII.

Example 4—In Situ Localization of G-Quadruplex Containing Structures

By using the compounds according to the invention, the inventors intended to detect, by fluorescent imaging, in situ localization of G-quadruplex containing molecules.

Material and Methods

Cell Culture and Fluorescence Microscopy

MCF7 cell line were obtained from the American Type Culture Collection (ATCC). Cells were cultured in 75 $cm^2$ flasks (Corning) in DMEM (Life Technologies) supplemented with 5% synthetic feta bovine serum (FetalClone III, GE LifeSciences) and 100 U penicillin-streptomycin mixture (1.0 $U\cdot mL^{-1}$ Pen/1.0 $mg\cdot mL^{-1}$ Strep) at 37° C. in a humidified, 5% $CO_2$ atmosphere-controlled incubator (HERAcell). The standard protocols were used for subculturing the cells: aspiration of medium, PBS (Gibco) wash, trypsinization in Trypsin-EDTA (0.25%) and reseeding in appropriate density. All cell counting was performed using the Coulter Counter (Beckman Coulter).

Click Imaging with MultiTASQ

MCF-7 cells were seeded on chambered coverglass (24 well-plate) and allowed to recover for 24 h. Cells were incubated with 100 µM MultiTASQ at 37° C. After 4 h, cells were fixed and permeabilized with paraformaldehyde (2% solubilized in 0.1% Triton X-100/PBS) for 5 min at room temperature. Treated cells were incubated during 30 min at room temperature with 1 µM alexafluor488-azide*+Igepal*0.05% in PBS+4 mM $CuSO_4$+10 mM Sodium ascorbate and rinsed with PBS 1×(thrice 5 min). Nuclei are counterstained with DAPI (1 µg/mL, 5 min). Cells were washed with PBS and mounted with Fluoromount-G (Southern Biotech). Confocal microscopy was performed either on a Zeiss LSM700 or on a Leica DMi8 microscope with the appropriate filters using the 63× objective. Foci quantification is done using Leica software.

G4RP Protocol with MultiTASQ

MCF7 cells were seeded at $3.5\times10^5$ cells per 10-cm dish for 72 h. Cells were then crosslinked using 1% formaldehyde/PBS for 5 min at 25° C. and the crosslinking was then quenched with 0.125 M glycine for 5 min. Cells were scraped and resuspended in G4RP buffer (150 mM KCl, 25 mM Tris pH7.4, 5 mM EDTA, 0.5 mM DTT, 0.5% NP40, RNase inhibitor (Roche), homebrew protease inhibitor cocktail). Cells were then sonicated using Covaris m220 Ultra-sonicator using default settings at 10% duty for 2 min. The sonicated fractions were then incubated with pre-clicked biotin conjugated beads (150 μM Biotin azide (Sigma), 5 mM E301 (Sigma), 4 mM CuSO4, 25 μM MultiTASQ (or 25 μM biotin for negative control)) overnight at 4° C. 10 μg of streptavidin-magnetic beads (Promega) was added and the extract was incubated for 2 h at 4° C. Magnetic beads were then washed 4 times in G4RP buffer for 5 min. The beads were then incubated at 70° C. for 1 h to reverse crosslink. TRIZOL was then used to extract the RNA from the beads using manufacturer's instructions.

RESULTS AND CONCLUSIONS

The in situ click images seen in FIG. 2 shown that MultiTASQ enters cells (live incubation) and accumulates in perinuclear regions (arrows) in a manner that was already described with the intrinsically fluorescent N-TASQ probe. More precisely, MultiTASQ interacts with accessible RNA G-quadruplexes within the cytoplasmic compartment, thereby altering their functionalities. As a consequence, ineffective RNA bound to TASQ accumulates in cytoplasmic granules known as processing bodies (or P-bodies), in which they will be either processed or degraded. This events thus triggers the accumulation of RNA/TASQ in clearly defined cytoplasmic foci, making them readily detectable via in situ click imaging after copper-catalyzed cycloaddition of alexafluor488-azide.

The invention claimed is:

1. A compound of formula I:

(I)

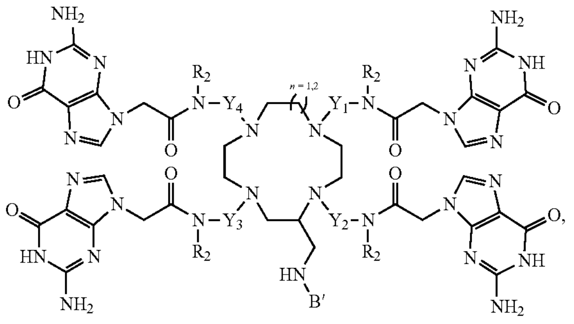

wherein

A is $Eu^{3+}$, $Tb^{3+}$, $Dy^{3+}$, or $Yb^{3+}$;

X1, X2 and X4 are, independently from each other a C1-C3 linear alkyl;

X3 is a C2-C3 alkyl, substituted by R1;

Y1, Y2, Y3 and Y4 are independently from each other a C1-C10 alkyl, saturated or not, substituted or not by an acid group, possibly with a substitution of at least one carbon atom by N, P, a phenyl, a C═O group, phosphonate group, or a triazole group;

Z1, Z2, Z3 and Z4 are independently from each other a C1-C5 linear alkyl;

R1 is $(CH_2)_p$-L-T, wherein p varies from 0 to 5; and

L is a linear or branched, saturated or not, C1-C12 alkyl, possibly with a substitution of at least one carbon by: a C═O group or an heteroatom, an aryl group possibly substituted, a triazole group, or a diazirin group;

T is a group allowing to carry out bioorthogonal reactions, in particular the following groups: azide, tetrazine substituted or not, alkyne, constrained alkyne, constrained cycloalkenes, and R2 is $(CH_2)_m$-NHRx, wherein m varies from 1 to 4 and Rx is H or a protecting group, or a guanidinium group, or a salt or a solvate thereof.

2. The compound according to claim 1, wherein Y1, Y2, Y3 and Y4 are independently from each other a C5-C10 alkyl, saturated or not, substituted or not by an acid group, possibly with a substitution of at least one carbon atom by N, P, a phenyl, a C═O group, phosphonate group, or a triazole group, and wherein A, X1, X2, X3, X4, Z1, Z2, Z3, Z4, R1 and R2 are as defined in claim 1.

3. The compound according to claim 1, said compound being of formula II:

(II)

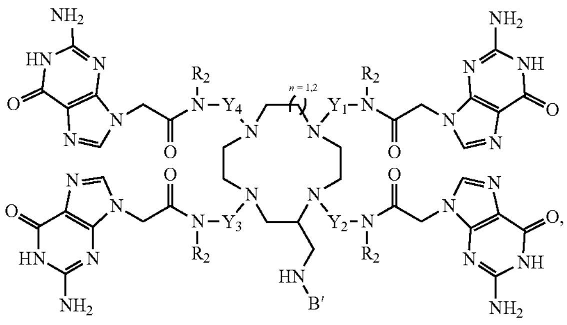

wherein B' is —(CO)—(CH2)m-T, m varying from 1 to 6, and Y1, Y2, Y3, Y4, T and R2 are as defined above.

4. The compound according to claim 1, said compound being of formula III:

(III)

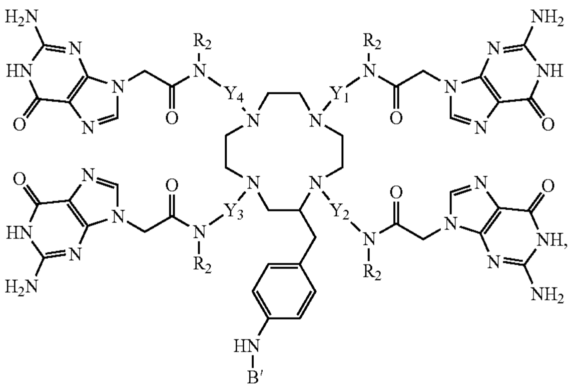

wherein:

B' is —W—(CH2)m-T, m varying from 1 to 6,

W═CO, C(═O)—NH, C(═S)—NH, or a group squaraine preferably CO, and

Y1, Y2, Y3, Y4, T and R2 are as defined above.

5. The compound according to claim 1, of formula IV:
(IV)
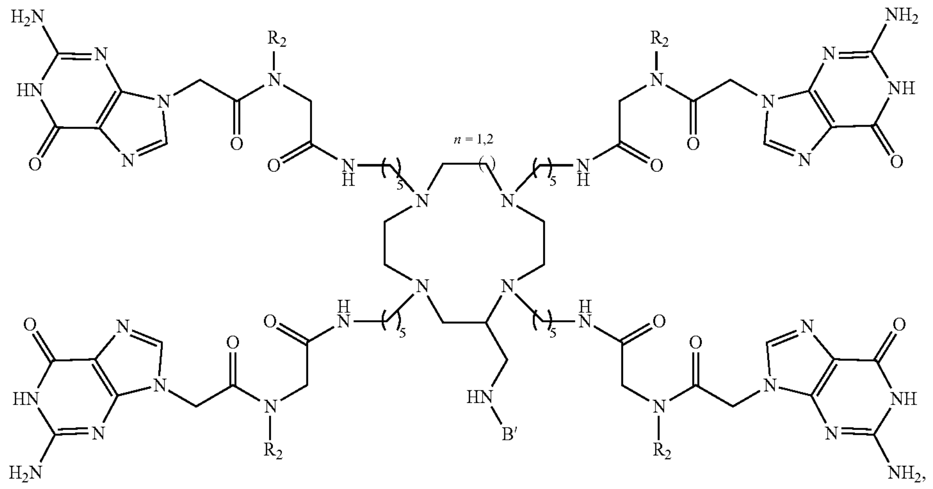
wherein B' is —(CO)—(CH2)m-T, m varying from 1 to 6, and
R2 are as defined above,
in particular the compound of formula IVa:
(IVb)
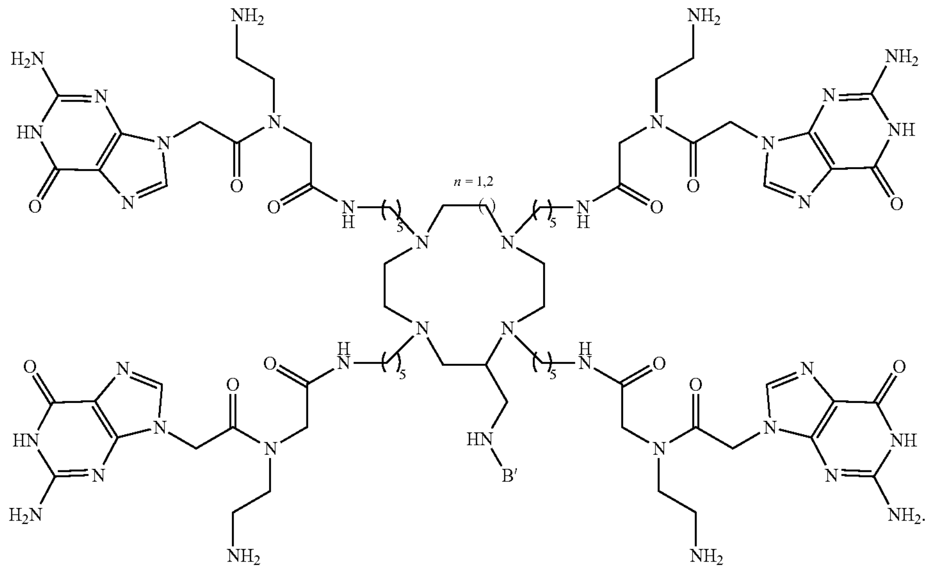

6. The compound according to claim 1, of formula V:
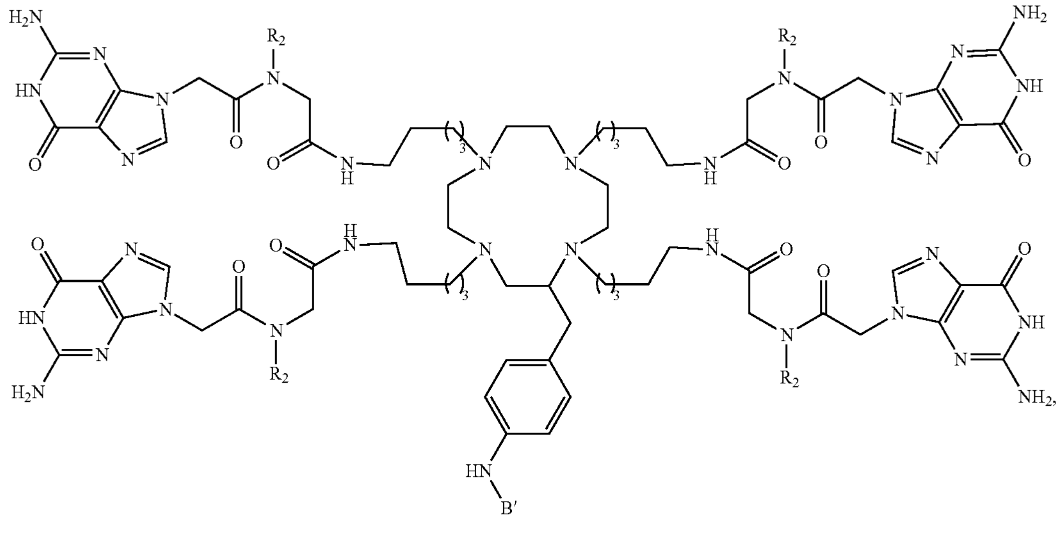
(V)
wherein B' is —(CO)—(CH2)m-T, m varying from 1 to 6, and
R2 are as defined above,
in particular the compound of formula Va:
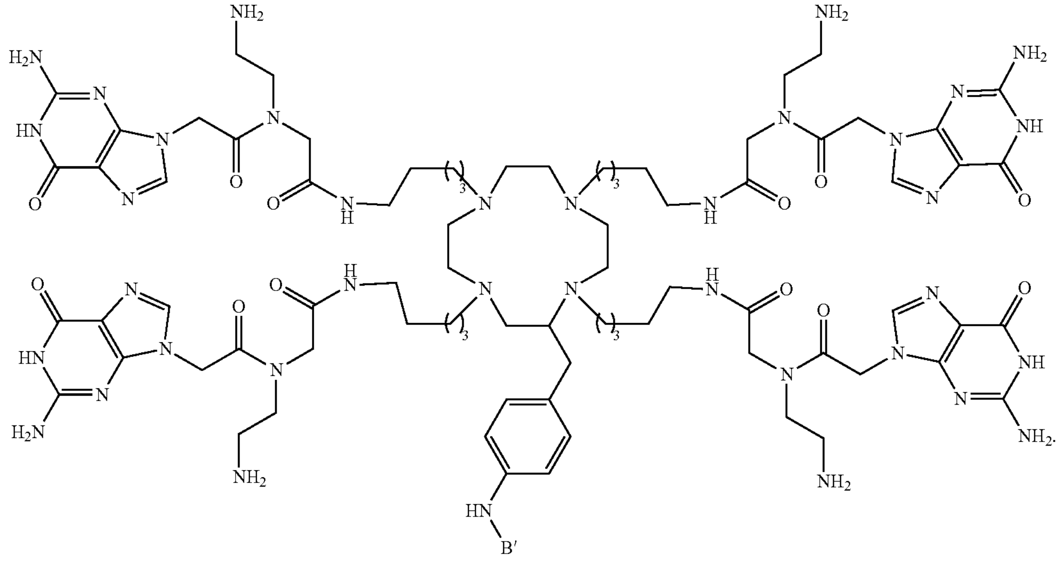
(Va)

7. The compound according to claim 1, said compound having one of the following formula:
(VI)
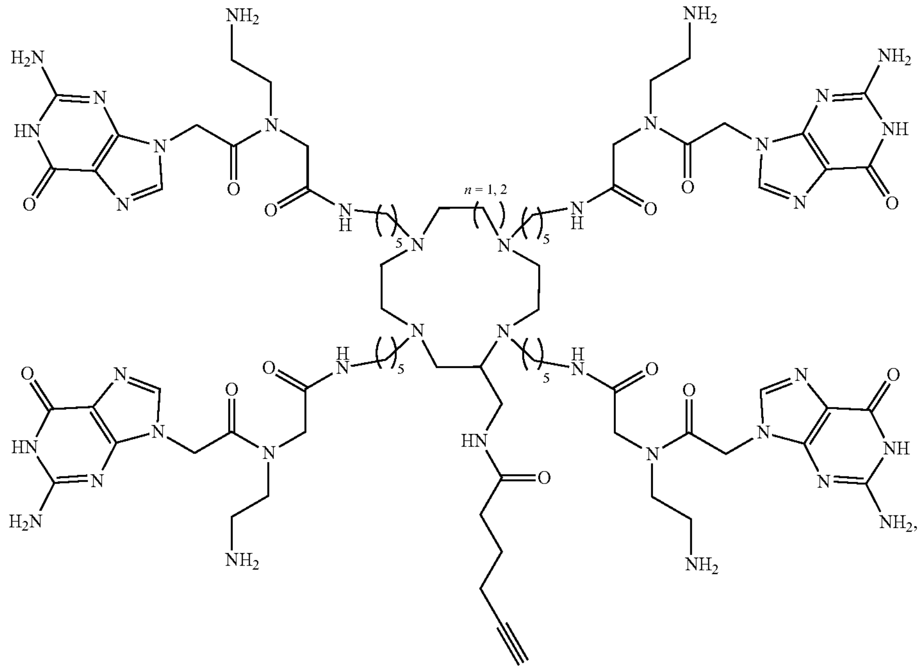
(VII)
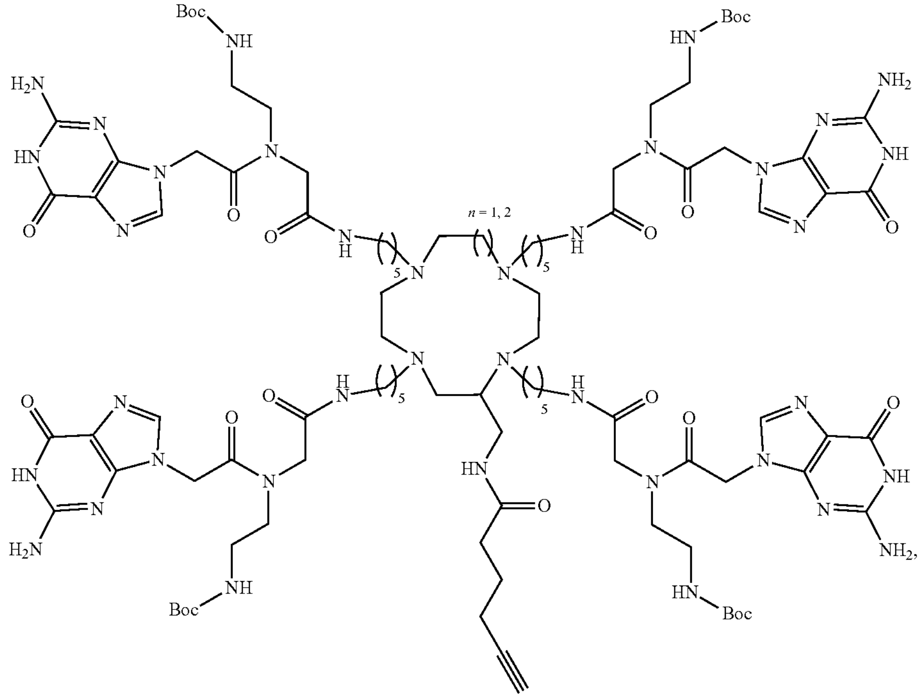

-continued
(VIII)
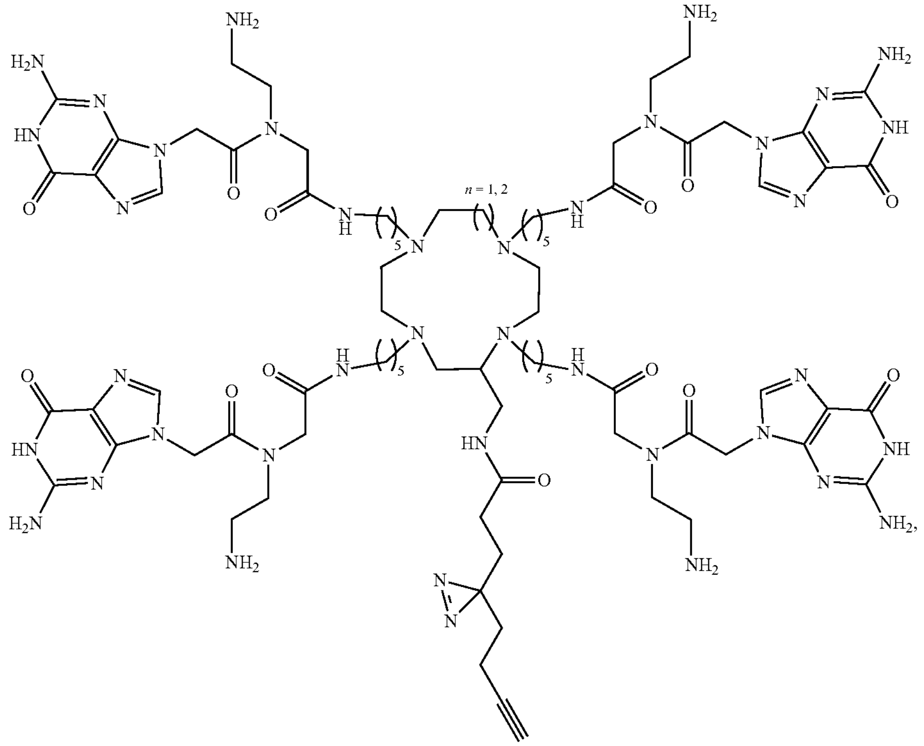
(IX)
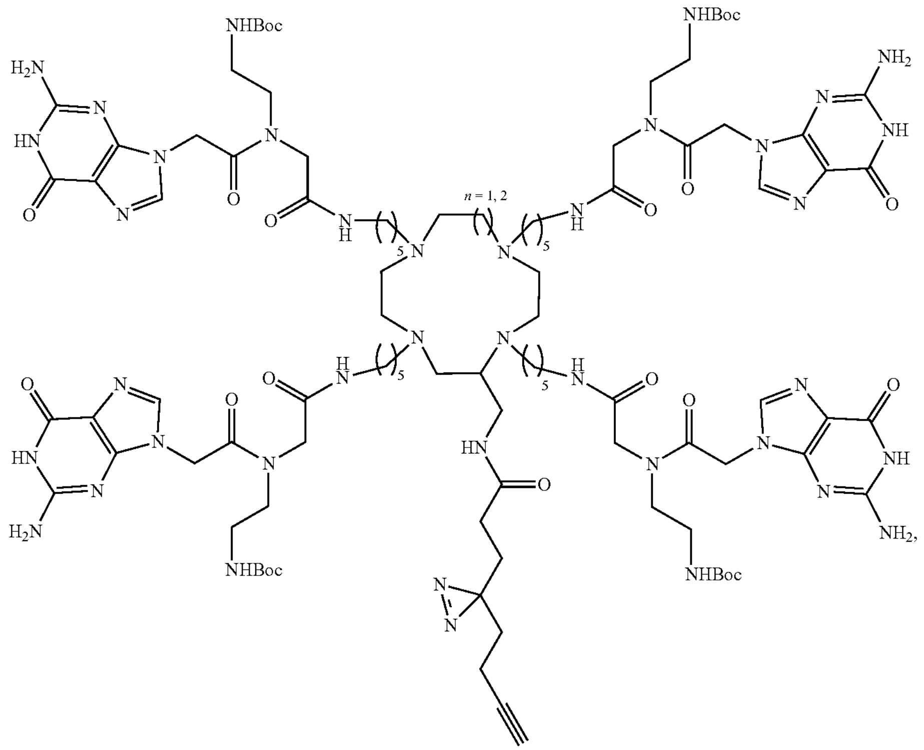

-continued
(X)
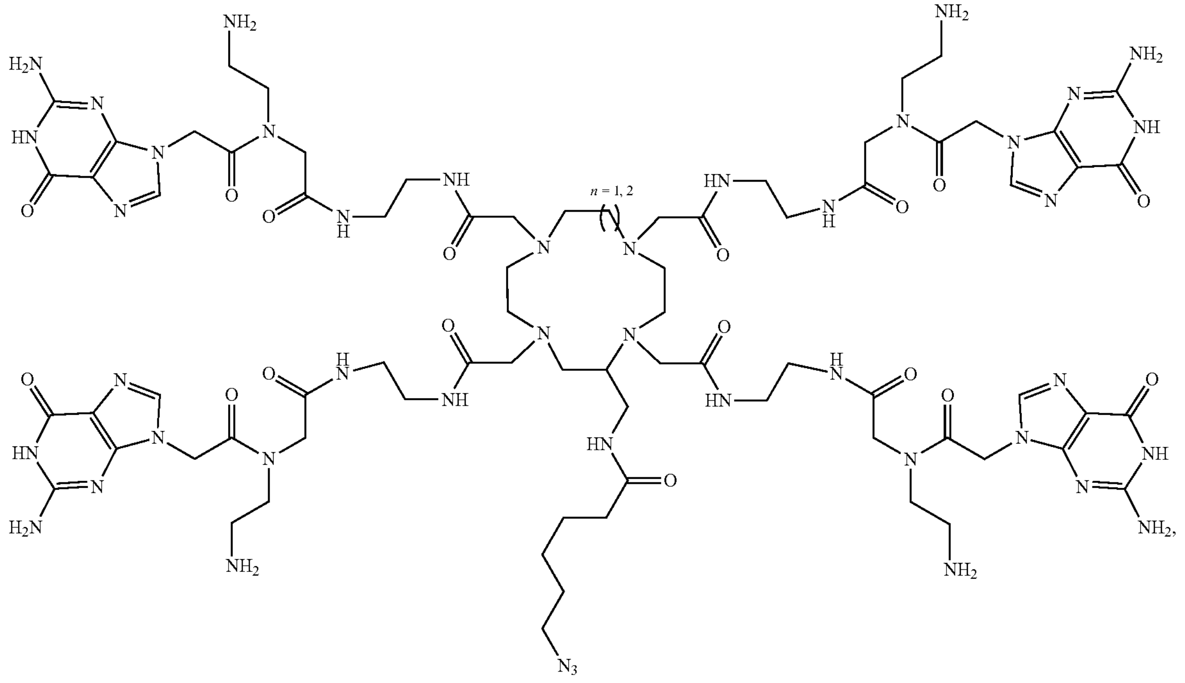
(XI)
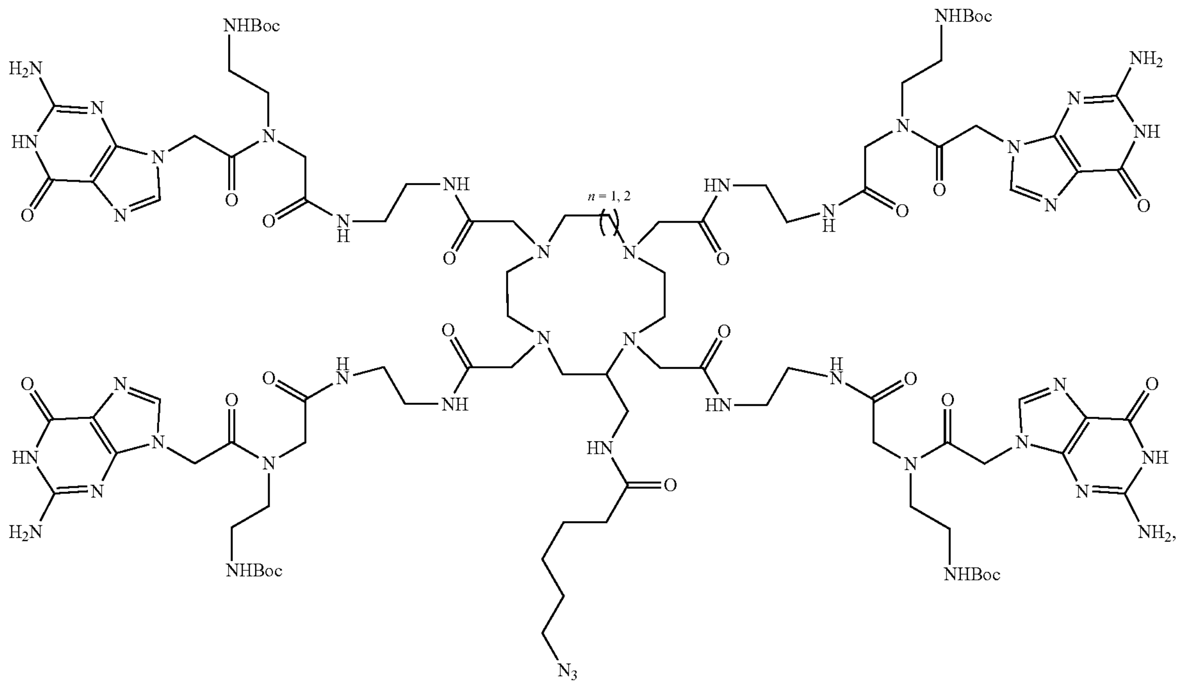

-continued
(XII)
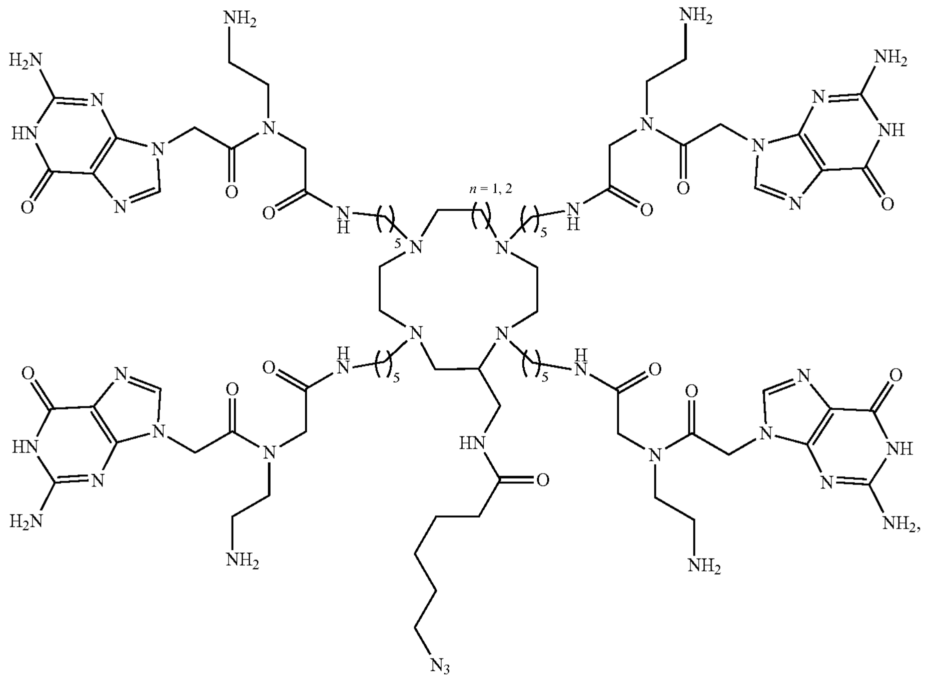
(XIII)
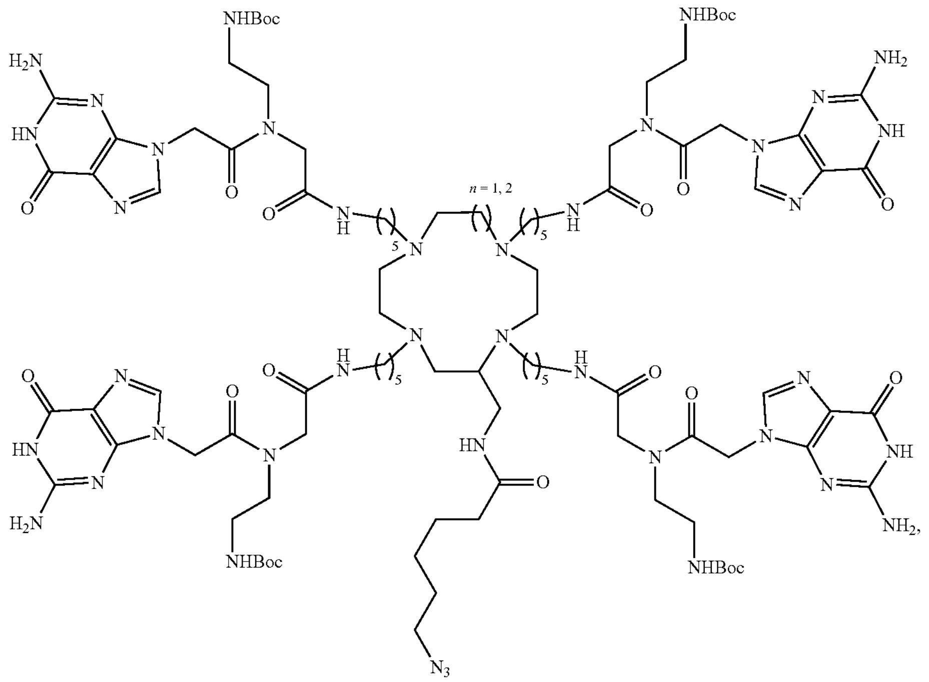

-continued
(XIV)
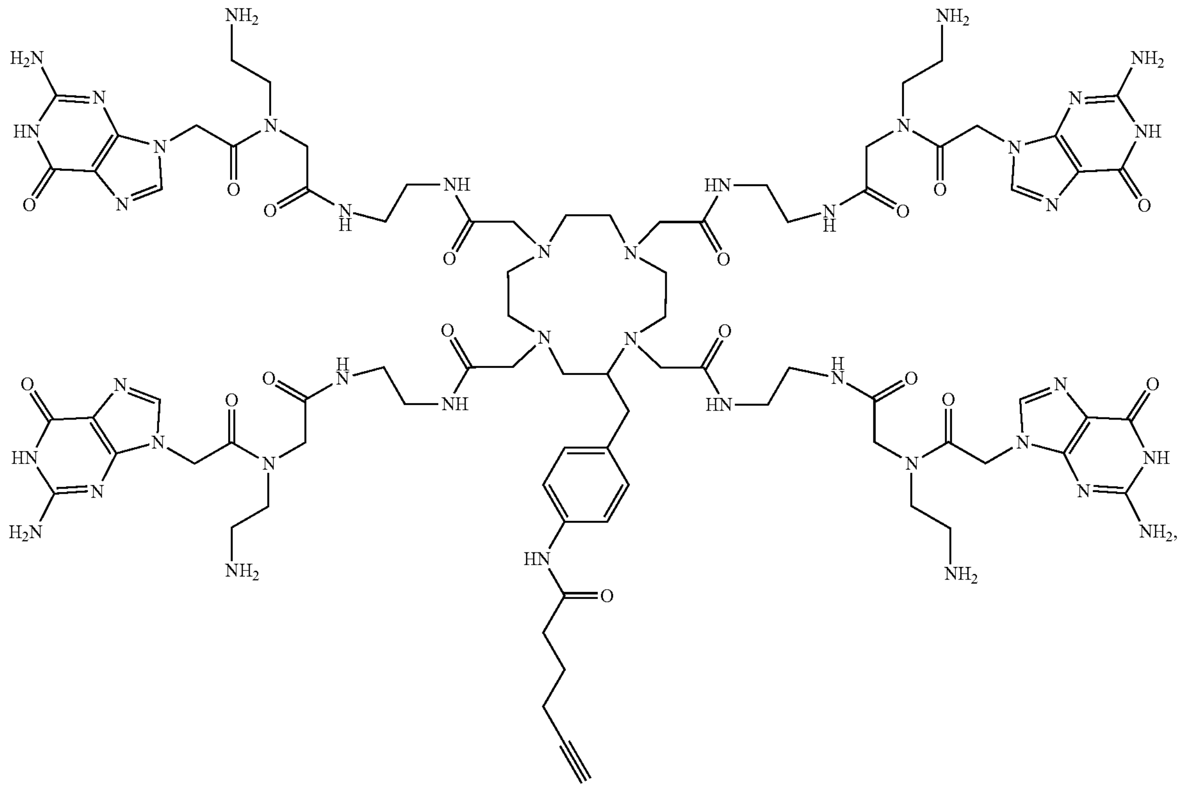
(XV)
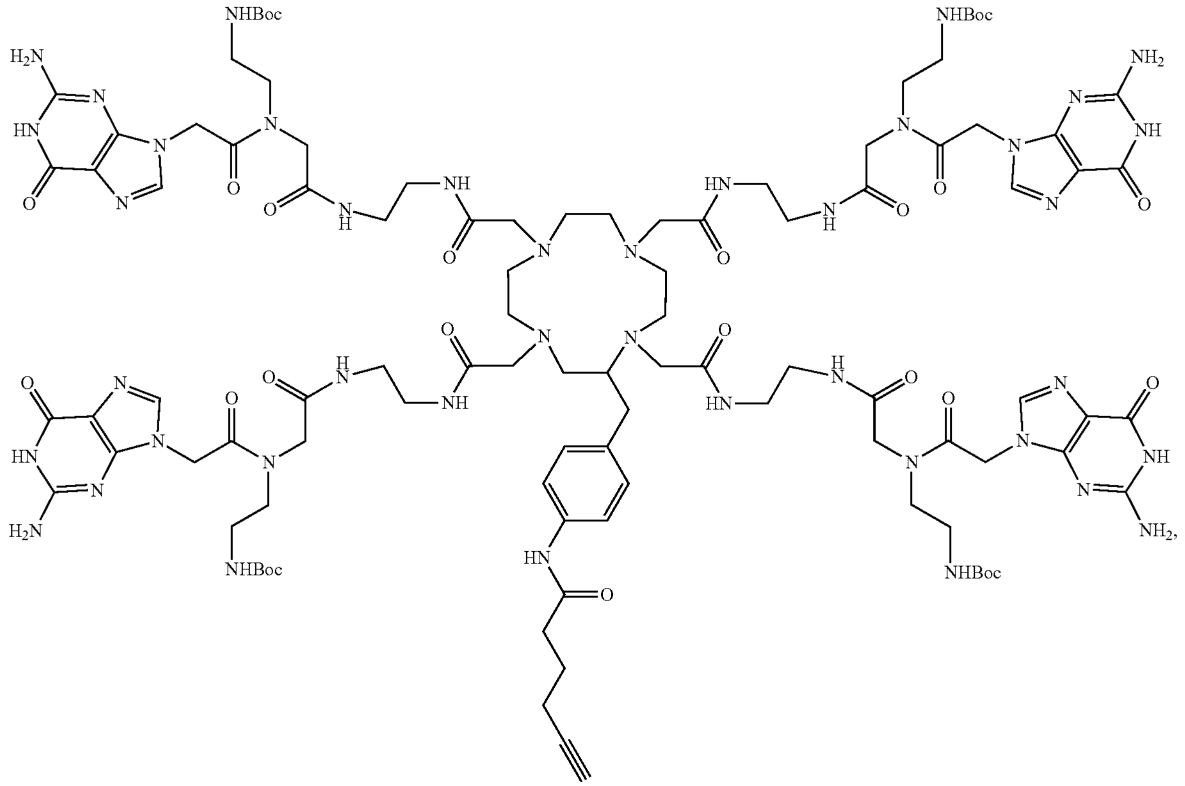

-continued
(XVI)
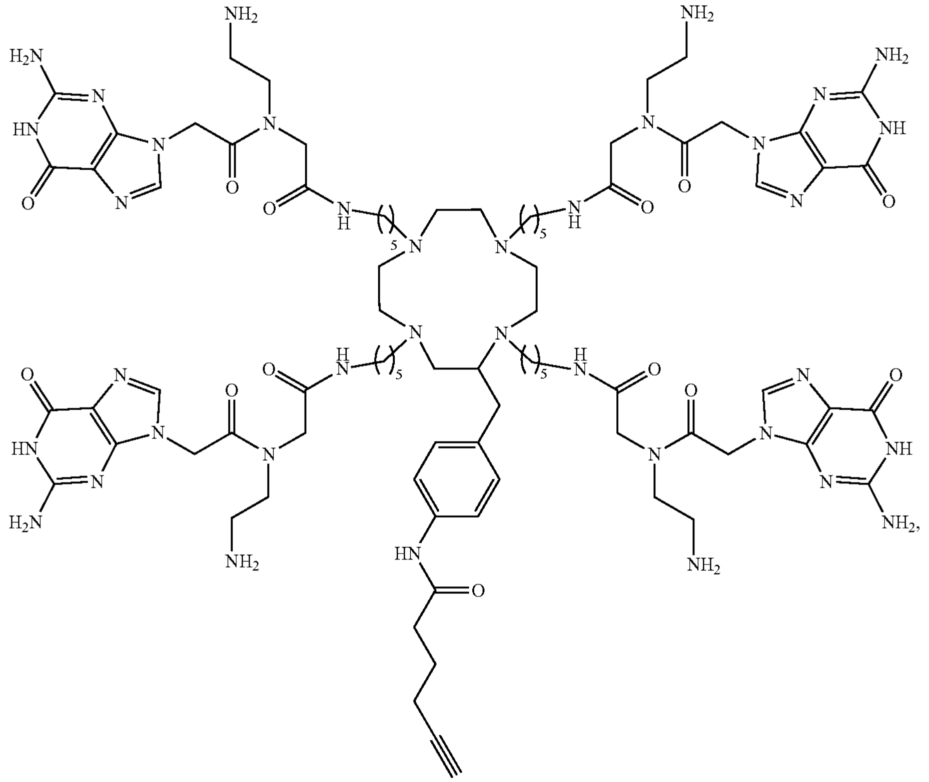
and
(XVII)
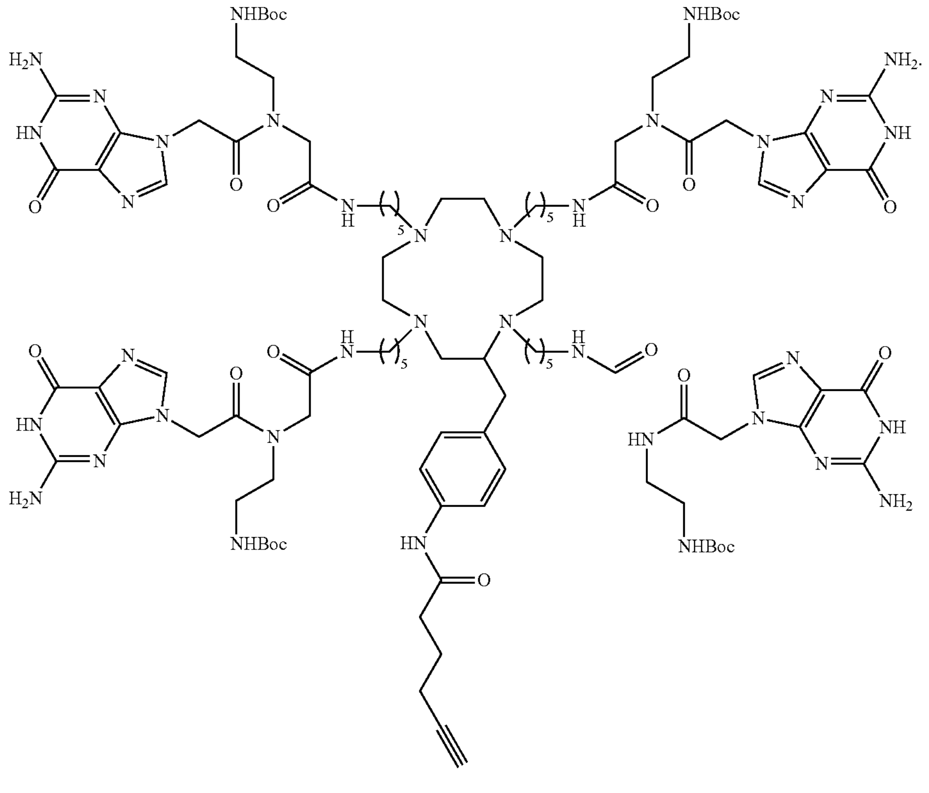

8. The compound according to claim 1, wherein the constrained alkyne is selected from cyclooctyne or cyclononyne, and in particular dibenzocyclooctyne and bicyclononyne.

9. The compound according to claim 1, wherein the constrained cycloalkenes is selected from trans-cyclooctene, norbornene and cycloproprene.

10. The compound according to claim 1, wherein the protecting group is selected from Boc, Fmoc and Carboxybenzyl.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: G-quadruplex containing probe

<400> SEQUENCE: 1

gggttagggt tagggttagg g                                                21


<210> SEQ ID NO 2
<211> LENGTH: 22
<212> TYPE: DNA
<213> ORGANISM: Artificial Sequence
<220> FEATURE:
<223> OTHER INFORMATION: G-quadruplex containing probe

<400> SEQUENCE: 2

gagggtgggg agggtgggga ag                                               22


<210> SEQ ID NO 3
<211> LENGTH: 26
<212> TYPE: DNA
<213> ORGANISM: Artificial Sequence
<220> FEATURE:
<223> OTHER INFORMATION: No G-quadruplex containing probe

<400> SEQUENCE: 3

tatagctata tttttttata gctata                                           26


<210> SEQ ID NO 4
<211> LENGTH: 17
<212> TYPE: DNA
<213> ORGANISM: Artificial Sequence
<220> FEATURE:
<223> OTHER INFORMATION: G-quadruplex containing probe

<400> SEQUENCE: 4

ggaggagggg aggagga                                                     17
```